US010421984B2

(12) United States Patent
Laird et al.

(10) Patent No.: US 10,421,984 B2
(45) Date of Patent: Sep. 24, 2019

(54) METHODS FOR REDUCING NORLEUCINE MISINCORPORATION INTO PROTEINS USING A MICROORGANISM COMPRISING A MUTANT METE ALLELE

(71) Applicant: Genentech, Inc., South San Francisco, CA (US)

(72) Inventors: Michael W. Laird, San Ramon, CA (US); Karthik Veeravalli, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/951,895

(22) Filed: Apr. 12, 2018

(65) Prior Publication Data

US 2018/0230506 A1 Aug. 16, 2018

Related U.S. Application Data

(60) Division of application No. 15/816,305, filed on Nov. 17, 2017, now Pat. No. 10,179,925, which is a division of application No. 15/067,646, filed on Mar. 11, 2016, now Pat. No. 9,850,514, which is a continuation of application No. 14/031,463, filed on Sep. 19, 2013, now abandoned.

(60) Provisional application No. 61/777,700, filed on Mar. 12, 2013, provisional application No. 61/703,142, filed on Sep. 19, 2012.

(51) Int. Cl.
| C12P 21/00 | (2006.01) |
| C12P 21/02 | (2006.01) |
| C12N 15/70 | (2006.01) |
| C12N 9/10 | (2006.01) |
| C07K 16/18 | (2006.01) |
| C07K 16/22 | (2006.01) |
| C07K 16/40 | (2006.01) |
| C07K 16/28 | (2006.01) |
| C07K 16/32 | (2006.01) |

(52) U.S. Cl.
CPC ............ *C12P 21/00* (2013.01); *C07K 16/18* (2013.01); *C07K 16/22* (2013.01); *C07K 16/2863* (2013.01); *C07K 16/32* (2013.01); *C07K 16/40* (2013.01); *C12N 9/1029* (2013.01); *C12N 9/1085* (2013.01); *C12N 15/70* (2013.01); *C12P 21/02* (2013.01); *C12Y 203/01046* (2013.01); *C12Y 205/01006* (2013.01); *C07K 2317/14* (2013.01)

(58) Field of Classification Search
None
See application file for complete search history.

(56) References Cited

U.S. PATENT DOCUMENTS

| 5,599,690 | A | 2/1997 | Fenton et al. |
| 5,698,418 | A | 12/1997 | Brunner et al. |
| 7,195,897 | B2 | 3/2007 | Leonhartsberger et al. |
| 7,371,551 | B1 | 5/2008 | Leonhartsberger et al. |
| 7,611,873 | B1 | 11/2009 | Usuda et al. |
| 9,850,514 | B2 * | 12/2017 | Laird ................. C07K 16/2863 |
| 2007/0009995 | A1 | 1/2007 | Bogosian et al. |
| 2009/0269338 | A1 | 10/2009 | Huang et al. |
| 2009/0298135 | A1 | 12/2009 | Maier et al. |
| 2010/0322931 | A1 | 12/2010 | Harding et al. |
| 2014/0081003 | A1 | 3/2014 | Laird et al. |
| 2016/0186227 | A1 | 6/2016 | Laird et al. |
| 2018/0080056 | A1 | 3/2018 | Laird et al. |

FOREIGN PATENT DOCUMENTS

| CN | 1703517 A | 11/2015 |
| EP | 0 737 752 A2 | 10/1996 |
| JP | 2006-503568 A | 2/2006 |
| WO | WO-1989/07651 A2 | 8/1989 |
| WO | WO-1989/07651 A3 | 8/1989 |
| WO | WO-1998/45331 A2 | 10/1998 |
| WO | WO-1998/45331 A3 | 10/1998 |
| WO | WO-2002/40697 A2 | 5/2002 |
| WO | WO-2002/40697 A3 | 5/2002 |
| WO | WO-2004/035617 A2 | 4/2004 |
| WO | WO-2004/035617 A3 | 4/2004 |
| WO | WO-2005/038017 A2 | 4/2005 |
| WO | WO-2005/038017 A3 | 4/2005 |
| WO | WO-2005/108561 A2 | 11/2005 |
| WO | WO-2005/108561 A3 | 11/2005 |
| WO | WO-2005/111202 A1 | 11/2005 |
| WO | WO-2007/103521 A2 | 9/2007 |
| WO | WO-2007/103521 A3 | 9/2007 |
| WO | WO-2008/055206 A2 | 5/2008 |
| WO | WO-2008/055206 A3 | 5/2008 |

(Continued)

OTHER PUBLICATIONS

Barker, D.G. et al., "The Fate of Norleucine as a Replacement for Methionine in Protein Synthesis," *J. Mol. Biol.* 133(2):217-231, (Sep. 15, 1979).
Bogosian, G. et al., "Biosynthesis and Incorporation into Protein of Norleucine by *Escherichia coli*," *The Journal of Biological Chemistry* 264(1):531-539, (1989).
Born, T.L. et al., "Enzyme-Catalyzed Acylation of Homoserine: Mechanistic Characterization of the *Escherichia coli* metA-Encoded Homoserine Transsuccinylase" *Biochemistry* 38(43):14416-14423, (Sep. 30, 1999).

(Continued)

*Primary Examiner* — Christian L Fronda
(74) *Attorney, Agent, or Firm* — Morrison and Foerster LLP

(57) ABSTRACT

The present invention relates to methods and compositions for preventing incorporation of norleucine into proteins during recombinant protein production in bacteria. The present invention also provides microorganism host cells and nucleic acid molecules for use with the methods and compositions provided herein.

29 Claims, 25 Drawing Sheets

Specification includes a Sequence Listing.

(56) References Cited

FOREIGN PATENT DOCUMENTS

| WO | WO-2009/134711 A1 | 11/2009 |
|---|---|---|
| WO | WO-2009/134711 A8 | 11/2009 |
| WO | WO-2011/143665 A1 | 11/2011 |

OTHER PUBLICATIONS

Brown, J.L. "The Modification of the Amino Terminal Region of *Escherichia coli* Proteins After Initiation With Methionine Analogues," *Biochimica et Biophysica Acta* 294(3):527-529, (Feb. 4, 1973).

Chattopadhyay, M.K. et al. "Control of Methionine Biosynthesis in *Escherichia coli* K12: A Closer Study With Analogue-Resistant Mutants," *J. Gen. Microbio.* 137:685-691, (1991).

Chen, Y. et al. "Selection and Analysis of an Optimized Anti-VEGF Antibody: Crystal Structure of an Affinity-Matured Fabin Complex With Antigen," *J. Mol. Biol.* 293:865-881, (1999).

Chica, R.A. et al. "Semi-Rational Approaches to Engineering Enzyme Activity: Combining the Benefits of Directed Evolution and Rational Design," *Curr. Opin. Biotechnol.* 16(4):378-384, (Aug. 2005).

Cohen, G.N. et al., "Effets Des Analogues Structuraux D'aminoacides Sur La Croissance, La Synthese De Proteines Et La Synthese D'enzymes Chez *Escherichia coli*," *Biochimica Et Biophysica Acta* 31(2):347-356, (Feb. 1959).

Cowie, D.B. et al., "Amino Acid Analog Incorporation Into Bacterial Proteins," *Biochimica Et Biophysica Acta* 34:39-46, (1959).

Fersht, A.R. et al. "An Editing Mechanism for the Methionyl-tRNA Synthetase in the Selection of Amino Acids in Protein Synthesis," *Biochemistry* 18(7):1250-1256, (Apr. 1979).

Marincs, F. et al., "Transcript Analysis Reveals an Extended Regulon and the Importance of Protein-Protein Co-Operativity for the *Escherichia coli* Methionine Repressor," *Biochem. J.* 396:227-234, (2006).

Markham, G.D. et al., "S-Adenosylmethionine Synthetase From *Escherichia coli*," *Journal of Biological Chemistry* 255(19):9082-9092, (Oct. 10, 1980).

Munier, R. et al., "Incorporation d'analogues structuraux d'aminoacides dans les proteins bacterennes," *Biochimica Et Biophysica Acta* 21:592-593, (1956.).

Munier, R. et al. "Incorporation D'Analogues Structuraux D'AminoAcides Dans Les Proteins Bacteriennes Au Cours De Leur Synthese in Vivo," *Biochimica et Biophysica Acta* 31:378-391, (1959).

Nakamori, S. et al., "Mechanism of L-Methionine Overproduction by *Escherichia coli*: The Replacement of Ser-54 by Asn in the MetJ Protein Causes the Derepression of l-Methionine Biosynthetic Enzymes," *Appl. Microbiol. Biotechnol.* 52(2):179-185, (Aug. 1999).

Randhawa et al. "Incorporation of Norleucine at Methionine Positions in Recombinant Human Macrophage Colony Stimulation Factor (M-CSF, 4-153) Expressed in *Escherichia coli*: Structural Analysis," *Biochemistry* 33:4342-4362 (1994).

Schulze et al. "Evidence for the Extent of Insertion of the Active Site Loop of Intact $\alpha_1$ Proteinase Inhibitor in $\beta$-Sheet A," *Biochemistry* 31(33):7560-7565, (Aug. 1992).

Sen, S. et al. "Developments in Directed Evolution for Improving Enzyme Functions," *Appl. Biochem. Biotechnol.* 143(3):212-223, (Dec. 2007, e-pub. Aug. 18, 2007).

Trupin, J. et al. "Formylation of Amino Acid Analogues of Methionine sRNA," *Biochemical and Biophysical Research Communications* 24(1):50-55, (Jul. 1996).

Tsai, L.B. et al. "Control of Misincorporation of De Novo Synthesized Norleucine Into Recombinant Interleukin-ln *E. coli*," *Biochemical and Biophysical Research Communications* 156(2):733-739, (Oct. 1998).

Usuda, Y. et al. "Effects of Deregulation of Methionine Biosynthesis on Methionine Excretion in *Escherichia coli*," *Applied and Environmental Microbiology* 71(6):3228-3234, (Jun. 2005).

Van Hest et al. "Efficient Incorporation of Unsaturated Methionine Analogues Into Proteins In Vivo," *J. Am. Chem. Soc.* 122:1282-1288, (2000, e-pub. Feb. 3, 2000).

International Preliminary Report on Patentability dated Mar. 24, 2015 for PCT Application No. PCT/US2013/060653, filed Sep. 19, 2013, 8 pages.

International Search Report dated Nov. 27, 2013 for PCT Application No. PCT/US2013/060653, filed Sep. 19, 2013, 6 pages.

Written Opinion of the International Searching Authority dated Nov. 27, 2013 for PCT Application No. PCT/US2013/060653, filed Sep. 19, 2013, 7 pages.

Sychev, E.V. et al. (2007) "Study of Over Synthesis of Non-Canonical Amino Acids *Escherichia coli*," *Microbiology* 76(6):805-812, with English Abstract Translation.

\* cited by examiner

ATGCCGATTCGTGTGCCGGACGAGCTACCCGCCGTCAATTTCTTGCGTGAAGAAAAC
GTCTTTGTGATGACAACTTCTTGTGCGTCTGGTCAGGAAATTCGTCCACTTAAGGTT
CTGATCCTTAACCTGATGCCGAAGAAGATTGAAACTGAAAATCAGTTTCTGCGCCTG
CTTTCAAACTCACCTTTGCAGGTCGATATTCAGCTGTTGCGCATCGATTCCCGTGAA
TCGCGCAACACGCCCGCAGAGCATCTGAACAACTTCTACTGTAACTTTGAAGATATT
CAGGATCAGAACTTTGACGGTTTGATTGTAACTGGTGCGCCGCTGGGCCTGGTGGAG
TTTAATGATGTCGCTTACTGGCCGCAGATCAAACAGGTGCTGGAGTGGTCGAAAGAT
CACGTCACCTCGACGCTGTTTGTCTGCTGGGCGGTACAGGCCGCGCTCAATATCCTC
TACGGCATTCCTAAGCAAACTCGCACCGAAAAACTCTCTGGCGTTTACGAGCATCAT
ATTCTCCATCCTCATGCGCTTCTGACGCGTGGCTTTGATGATTCATTCCTGGCACCG
CATTCGCGCTATGCTGACTTTCCGGCAGCGTTGATTCGTGATTACACCGATCTGGAA
ATTCTGGCAGAGACGGAAGAAGGGGATGCATATCTGTTTGCCAGTAAAGATAAGCGC
ATTGCCTTTGTGACGGGCCATCCCGAATATGATGCGCAAACGCTGGCGCAGGAATTT
TTCCGCGATGTGGAAGCCGGACTAGACCCGGATGTACCGTATAACTATTTCCCGCAC
AATGATCCGCAAAATACACCGCGAGCGAGCTGGCGTAGTCACGGTAATTTACTGTTT
ACCAACTGGCTCAACTATTACGTCTACCAGATCACGCCATACGATCTACGGCACATG
AATCCAACGCTGGATTAA

*FIG. 1*

ATGCCGATTCGTGTGCCGGACGAGCTACCCGCCGTCAATTTCTTGCGTGAAGAAAAC
GTCTTTGTGATGACAACTTCTCGTGCGTCTGGTCAGGAAATTCGTCCACTTAAGGTT
CTGATCCTTAACCTGATGCCGAAGAAGATTGAAACTGAAAATCAGTTTCTGCGCCTG
CTTTCAAACTCACCTTTGCAGGTCGATATTCAGCTGTTGCGCATCGATTCCCGTGAA
TCGCGCAACACGCCCGCAGAGCATCTGAACAACTTCTACTGTAACTTTGAAGATATT
CAGGATCAGAACTTTGACGGTTTGATTGTAACTGGTGCGCCGCTGGGCCTGGTGGAG
TTTAATGATGTCGCTTACTGGCCGCAGATCAAACAGGTGCTGGAGTGGTCGAAAGAT
CACGTCACCTCGACGCTGTTTGTCTGCTGGGCGGTACAGGCCGCGCTCAATATCCTC
TACGGCATTCCTAAGCAAACTCGCACCGAAAAACTCTCTGGCGTTTACGAGCATCAT
ATTCTCCATCCTCATGCGCTTCTGACGCGTGGCTTTGATGATTCATTCCTGGCACCG
CATTCGCGCTATGCTGACTTTCCGGCAGCGTTGATTCGTGATTACACCGATCTGGAA
ATTCTGGCAGAGACGGAAGAAGGGGATGCATATCTGTTTGCCAGTAAAGATAAGCGC
ATTGCCTTTGTGACGGGCCATCCCGAATATGATGCGCAAACGCTGGCGCAGGAATTT
TTCCGCGATGTGGAAGCCGGACTAGACCCGGATGTACCGTATAACTATTTCCCGCAC
AATGATCCGCAAAATACACCGCGAGCGAGCTGGCGTAGTCACGGTAATTTACTGTTT
ACCAACTGGCTCAACTATTACGTCTGCCAGATCACGCCATACGATCTACGGCACATG
AATCCAACGCTGGATTAA

*FIG. 2*

ATGCCGATTCGTGTGCCGGACGAGCTACCCGCCGTCAATTTCTTGCGTGAAGAAAAC
GTCTTTGTGATGACAACTTCTCGTGCGTCTGGTCAGGAAATTCGTCCACTTAAGGTT
CTGATCCTTAACCTGATGCCGAAGAAGATTGAAACTGAAAATCAGTTTCTGCGCCTG
CTTTCAAACTCACCTTTGCAGGTCGATATTCAGCTGTTGCGCATCGATTCCCGTGAA
TCGCGCAACACGCCCGCAGAGCATCTGAACAACTTCTACTGTAACTTTGAAGATATT
CAGGATCAGAACTTTGACGGTTTGATTGTAACTGGTGCGCCGCTGGGCCTGGTGGAG
TTTAATGATGTCGCTTACTGGCCGCAGATCAAACAGGTGCTGGAGTGGTCGAAAGAT
CACGTCACCTCGACGCTGTTTGTCTGCTGGGCGGTACAGGCCGCGCTCAATATCCTC
TACGGCATTCCTAAGCAAACTCGCACCGAAAAACTCTCTGGCGTTTACGAGCATCAT
ATTCTCCATCCTCATGCGCTTCTGACGCGTGGCTTTGATGATTCATTCCTGGCACCG
CATTCGCGCTATGCTGACTTTCCGGCAGCGTTGATTCGTGATTACACCGATCTGGAA
ATTCTGGCAGAGACGGAAGAAGGGGATGCATATCTGTTTGCCAGTAAAGATAAGCGC
ATTGCCTTTGTGACGGGCCATCCCGAATATGATGCGCAAACGCTGGCGCAGGAATTT
TTCCGCGATGTGGAAGCCGGACTAGACCCGGATGTACCGTATAACTATTTCCCGCAC
AATGATCCGCAAAATACACCGCGAGCGAGCTGGCGTAGTCACGGTAATTTACTGTTT
ACCAACTGGCTCAACTATTACGTCTACCAGAGCACGCTATACGATCTACGGCACATG
AATCCAACGCTGGATTAA

*FIG. 3*

ATGCCGATTCGTGTGCCGGACGAGCTACCCGCCGTCAATTTCTTGCGTGAAGAAAAC
GTCTTTGTGATGACAACTTCTCGTGCGTCTGGTCAGGAAATTCGTCCACTTAAGGTT
CTGATCCTTAACCTGATGCCGAAGAAGATTGAAACTGAAAATCAGTTTCTGCGCCTG
CTTTCAAACTCACCTTTGGAGGTCGATATTCAGCTGTTGCGCATCGATTCCCGTGAA
TCGCGCAACACGCCCGCAGAGCATCTGAACAACTTCTACTGTAACTTTGAAGATATT
CAGGATCAGAACTTTGACGGTTTGATTGTAACTGGTGCGCCGCTGGGCCTGGTGGAG
TTTAATGATGTCGCTTACTGGCCGCAGATCAAACAGGTGCTGGAGTGGTCGAAAGAT
CACGTCACCTCGACGCTGTTTGTCTGCTGGGCGGTACAGGCCGCGCTCAATATCCTC
TACGGCATTCCTAAGCAAACTCGCACCGAAAAACTCTCTGGCGTTTACGAGCATCAT
ATTCTCCATCCTCATGCGCTTCTGACGCGTGGCTTTGATGATTCATTCCTGGCACCG
CATTCGCGCTATGCTGACTTTCCGGCAGCGTTGATTCGTGATTACACCGATCTGGAA
ATTCTGGCAGAGACGGAAGAAGGGGATGCATATCTGTTTGCCAGTAAAGATAAGCGC
ATTGCCTTTGTGACGGGCCATCCCGAATATGATGCGCAAACGCTGGCGCAGGAATTT
TTCCGCGATGTGGAAGCCGGACTAGACCCGGATGTACCGTATAACTATTTCCCGCAC
AATGATCCGCAAAATACACCGCGAGCGAGCTGGCGTAGTCACGGTAATTTACTGTTT
ACCAACTGGCTCAACTATTACGTCTACCAGATCACGCCATACGATCTACGGCACATG
AATCCAACGCTGGATTAA

*FIG. 4*

ATGGCAAAACACCTTTTTACGTCCGAGTCCGTCTCTGAAGGGCATCCTGACAAAATT
GCTGACCAAATTTCTGATGCCGTTTTAGACGCGATCCTCGAACAGGATCCGAAAGCA
CGCGTTGCTTGCGAAACCTACGTAAAAACCGGCATGGTTTTAGTTGGCGGCGAAATC
ACCACCAGCGCCTGGGTAGACATCGAAGAGATCACCCGTAACACCGTTCGCGAAATT
GGCTATGTGCATTCCGACATGGGCTTTGACGCTAACTCCTGTGCGGTTCTGAGCGCT
ATCGGCAAACAGTCTCCTGACATCAACCAGGGCGTTGACCGTGCCGATCCGCTGGAA
CAGGGCGCGGGTGACCAGGGTCTGATGTTTGGCTACGCAACTAATGAAACCGACGTG
CTGATGCCAGCACCTATCACCTATGCACACCGTCTGGTACAGCGTCAGGCTGAAGTG
CGTAAAAACGGCACTCTGCCGTGGCTGCGCCCGGACGCGAAAAGCCAGGTGACTTTT
CAGTATGACGACGGCAAAATCGTTGGTATCGATGCTGTCAGCTTTCCACTCAGCAC
TCTGAAGAGATCGACCAGAAATCGCTGCAAGAAGCGGTAATGGAAGAGATCATCAAG
CCAATTCTGCCCGCTGAATGGCTGACTTCTGCCACCAAATTCTTCATCAACCCGACC
GGTCGTTTCGTTATCGGTGGCCCAATGGGTGACTGCGGTCTGACTGGTCGTAAAATT
ATCGTTGATACCTACGGCGGCATGGCGCGTCACGGTGGCGGTGCATTCTCTGGTAAA
GATCCATCAAAAGTGGACCGTTCCGCAGCCTACGCAGCACGTTATGTCGCGAAAAAC
ATCGTTGCTGCTGGCCTGGCCGATCGTTGTGAAATTCAGGTTTCCTACGCAATCGGC
GTGGCTGAACCGACCTCCATCATGGTAGAAACTTTCGGTACTGAGAAAGTGCCTTCT
GAACAACTGACCCTGCTGGTACGTGAGTTCTTCGACCTGCGCCCATACGGTCTGATT
CAGATGCTGGATCTGCTGCACCCGATCTACAAAGAAACCGCAGCATACGGTCACTTT
GGTCGTGAACATTTCCCGTGGGAAAAAACCGACAAAGCGCAGCTGCTGCGCGATGCT
GCCGGTCTGAAGTAA

*FIG. 5*

ATGGCAAAACACCTTTTTACGTCCGAGTCCGTCTCTGAAGGGCATCCTGACAAAATT
GCTGACCAAATTTCTGATGCCGTTTTAGACGCGATCCTCGAACAGGATCCGAAAGCA
CGCGTTGCTTGCGAAACCTACGTAAAAACCGGCATGGTTTTAGTTGGCGGCGAAATC
ACCACCAGCGCCTGGGTAGACATCGAAGAGATCACCCGTAACACCGTTCGCGAAATT
GGCTATGTGCATTCCGACATGGGCTTTGACGCTAACTCCTGTGCGGTTCTGAGCGCT
ATCGGCAAACAGTCTCCTGACATCAACCAGGGCGTTGACCGTGCCGATCCGCTGGAA
CAGGGCGCGGGTGACCAGGGTCTGATGTTTGGCTACGCAACTAATGAAACCGACGTG
CTGATGCCAGCACCTATCACCTATGCACACCGTCTGGTACAGCGTCAGGCTGAAGTG
CGTAAAAACGGCACTCTGCCGTGGCTGCGCCCGGACGCGAAAAGCCAGGTGACTTTT
CAGTATGACGACGGCAAAATCGTTGGTATCGATGCTGTCGTGCTTTCCACTCAGCAC
TCTGAAGAGATCGACCAGAAATCGCTGCAAGAAGCGGTAATGGAAGAGATCATCAAG
CCAATTCTGCCCGCTGAATGGCTGACTTCTGCCACCAAATTCTTCATCAACCCGACC
GGTCGTTTCGTTATCGGTGGCCCAATGGGTGACTGCGGTCTGACTGGTCGTAAAATT
ATCGTTGATACCTACGGCGGCATGGCGCGTCACGGTGGCGGTGCATTCTCTGGTAAA
GATCCATCAAAAGTGGACCGTTCCGCAGCCTACGCAGCACGTTATGTCGCGAAAAAC
ATCGTTGCTGCTGGCCTGGCCGATCGTTGTGAAATTCAGGTTTCCTACGCAATCGGC
GTGGCTGAACCGACCTCCATCATGGTAGAAACTTTCGGTACTGAGAAAGTGCCTTCT
GAACAACTGACCCTGCTGGTACGTGAGTTCTTCGACCTGCGCCCATACGGTCTGATT
CAGATGCTGGATCTGCTGCACCCGATCTACAAAGAAACCGCAGCATACGGTCACTTT
GGTCGTGAACATTTCCCGTGGGAAAAAACCGACAAAGCGCAGCTGCTGGCGATGCTG
CCGGTCTGAAGTAA

*FIG. 6*

MPIRVPDELPAVNFLREENVFVMTTSRASGQEIRPLKVLILNLMPKKIETENQFLRL
LSNSPLQVDIQLLRIDSRESRNTPAEHLNNFYCNFEDIQDQNFDGLIVTGAPLGLVE
FNDVAYWPQIKQVLEWSKDHVTSTLFVCWAVQAALNILYGIPKQTRTEKLSGVYEHH
ILHPHALLTRGFDDSFLAHSRYADFPAALIRDYTDLEILAETEEGDAYLFASKDKRI
AFVTGHPEYDAQTLAQEFFRDVEAGLDPDVPYNYFPHNDPQNTPRASWRSHGNLLFT
NWLNYYVYQITPYDLRHMNPTLD

*FIG. 7A*

ATGCCGATTCGTGTGCCGGACGAGCTACCCGCCGTCAATTTCTTGCGTGAAGAAAAC
GTCTTTGTGATGACAACTTCTTGTGCGTCTGGTCAGGAAATTCGTCCACTTAAGGTT
CTGATCCTTAACCTGATGCCGAAGAAGATTGAAACTGAAAATCAGTTTCTGCGCCTG
CTTTCAAACTCACCTTTGCAGGTCGATATTCAGCTGTTGCGCATCGATTCCCGTGAA
TCGCGCAACACGCCCGCAGAGCATCTGAACAACTTCTACTGTAACTTTGAAGATATT
CAGGATCAGAACTTTGACGGTTTGATTGTAACTGGTGCGCCGCTGGGCCTGGTGGAG
TTTAATGATGTCGCTTACTGGCCGCAGATCAAACAGGTGCTGGAGTGGTCGAAAGAT
CACGTCACCTCGACGCTGTTTGTCTGCTGGGCGGTACAGGCCGCGCTCAATATCCTC
TACGGCATTCCTAAGCAAACTCGCACCGAAAAACTCTCTGGCGTTTACGAGCATCAT
ATTCTCCATCCTCATGCGCTTCTGACGCGTGGCTTTGATGATTCATTCCTGGCACCG
CATTCGCGCTATGCTGACTTTCCGGCAGCGTTGATTCGTGATTACACCGATCTGGAA
ATTCTGGCAGAGACGGAAGAAGGGGATGCATATCTGTTTGCCAGTAAAGATAAGCGC
ATTGCCTTTGTGACGGGCCATCCCGAATATGATGCGCAAACGCTGGCGCAGGAATTT
TTCCGCGATGTGGAAGCCGGACTAGACCCGGATGTACCGTATAACTATTTCCCGCAC
AATGATCCGCAAAATACACCGCGAGCGAGCTGGCGTAGTCACGGTAATTTACTGTTT
ACCAACTGGCTCAACTATTACGTCTACCAGATCACGCCATACGATCTACGGCACATG
AATCCAACGCTGGATTAA

*FIG. 7B*

MAKHLFTSESVSEGHPDKIADQISDAVLDAILEQDPKARVACETYVKTGMVLVGGEI
TTSAWVDIEEITRNTVREIGYVHSDMGFDANSCAVLSAIGKQSPDINQGVDRADPLE
QGAGDQGLMFGYATNETDVLMPAPITYAHRLVQRQAEVRKNGTLPWLRPDAKSQVTF
QYDDGKIVGIDAVVLSTQHSEEIDQKSLQEAVMEEIIKPILPAEWLTSATKFFINPT
GRFVIGGPMGDCGLTGRKIIVDTYGGMARHGGGAFSGKDPSKVDRSAAYAARYVAKN
IVAAGLADRCEIQVSYAIGVAEPTSIMVETFGTEKVPSEQLTLLVREFFDLRPYGLI
QMLDLLHPIYKETAAYGHFGREHFPWEKTDKAQLLRDAAGLK

*FIG. 8A*

ATGGCAAAACACCTTTTTACGTCCGAGTCCGTCTCTGAAGGGCATCCTGACAAAATT
GCTGACCAAATTTCTGATGCCGTTTTAGACGCGATCCTCGAACAGGATCCGAAAGCA
CGCGTTGCTTGCGAAACCTACGTAAAAACCGGCATGGTTTTAGTTGGCGGCGAAATC
ACCACCAGCGCCTGGGTAGACATCGAAGAGATCACCCGTAACACCGTTCGCGAAATT
GGCTATGTGCATTCCGACATGGGCTTTGACGCTAACTCCTGTGCGGTTCTGAGCGCT
ATCGGCAAACAGTCTCCTGACATCAACCAGGGCGTTGACCGTGCCGATCCGCTGGAA
CAGGGCGCGGGTGACCAGGGTCTGATGTTTGGCTACGCAACTAATGAAACCGACGTG
CTGATGCCAGCACCTATCACCTATGCACACCGTCTGGTACAGCGTCAGGCTGAAGTG
CGTAAAAACGGCACTCTGCCGTGGCTGCGCCCGGACGCGAAAAGCCAGGTGACTTTT
CAGTATGACGACGGCAAAATCGTTGGTATCGATGCTGTCGTGCTTTCCACTCAGCAC
TCTGAAGAGATCGACCAGAAATCGCTGCAAGAAGCGGTAATGGAAGAGATCATCAAG
CCAATTCTGCCCGCTGAATGGCTGACTTCTGCCACCAAATTCTTCATCAACCCGACC
GGTCGTTTCGTTATCGGTGGCCCAATGGGTGACTGCGGTCTGACTGGTCGTAAAATT
ATCGTTGATACCTACGGCGGCATGGCGCGTCACGGTGGCGGTGCATTCTCTGGTAAA
GATCCATCAAAAGTGGACCGTTCCGCAGCCTACGCAGCACGTTATGTCGCGAAAAAC
ATCGTTGCTGCTGGCCTGGCCGATCGTTGTGAAATTCAGGTTTCCTACGCAATCGGC
GTGGCTGAACCGACCTCCATCATGGTAGAAACTTTCGGTACTGAGAAAGTGCCTTCT
GAACAACTGACCCTGCTGGTACGTGAGTTCTTCGACCTGCGCCCATACGGTCTGATT
CAGATGCTGGATCTGCTGCACCCGATCTACAAAGAAACCGCAGCATACGGTCACTTT
GGTCGTGAACATTTCCCGTGGGAAAAAACCGACAAAGCGCAGCTGCTGCGCGATGCT
GCCGGTCTGAAGTAA

*FIG. 8B*

```
GATATCCAGTTGACCCAGTCCC
CGAGCTCCCTGTCCGCCTCTGTGGGCGATAGGGTCACCATCACCTGCAGCGCAAGTCAGG
ATATTAGCAACTATTTAAACTGGTATCAACAGAAACCAGGAAAAGCTCCGAAAGTACTGA
TTTACTTCACCTCCTCTCTCCACTCTGGAGTCCCTTCTCGCTTCTCTGGATCCGGTTCTG
GGACGGATTTCACTCTGACCATCAGCAGTCTGCAGCCAGAAGACTTCGCAACTTATTACT
GTCAACAGTATAGCACCGTGCCGTGGACGTTTGGACAGGGTACCAAGGTGGAGATCAAAC
GAACTGTGGCTGCACCATCTGTCTTCATCTTCCCGCCATCTGATGAGCAGTTGAAATCTG
GAACTGCTTCTGTTGTGTGCCTGCTGAATAACTTCTATCCCAGAGAGGCCAAAGTACAGT
GGAAGGTGGATAACGCCCTCCAATCGGGTAACTCCCAGGAGAGTGTCACAGAGCAGGACA
GCAAGGACAGCACCTACAGCCTCAGCAGCACCCTGACGCTGAGCAAAGCAGACTACGAGA
AACACAAAGTCTACGCCTGCGAAGTCACCCATCAGGGCCTGAGCTCGCCCGTCACAAAGA
GCTTCAACAGGGGAGAGTGT
```

FIG. 18A

```
GAGGTTC
AGCTGGTGGAGTCTGGCGGTGGCCTGGTGCAGCCAGGGGGCTCACTCCGTTTGTCCTGTG
CAGCTTCTGGCTACGACTTCACGCACTACGGTATGAACTGGGTCCGTCAGGCCCCGGGTA
AGGGCCTGGAATGGGTTGGATGGATTAACACCTATACCGGTGAACCGACCTATGCTGCGG
ATTTCAAACGTCGTTTCACTTTTTCTTTAGACACCTCCAAAAGCACAGCATACCTGCAGA
TGAACAGCCTGCGCGCTGAGGACACTGCCGTCTATTACTGTGCAAAGTACCCGTACTATT
ATGGGACGAGCCACTGGTATTTCGACGTCTGGGGTCAAGGAACCCTGGTCACCGTCTCCT
CGGCCTCCACCAAGGGCCCATCGGTCTTCCCCCTGGCACCCTCCTCCAAGAGCACCTCTG
GGGGCACAGCGGCCCTGGGCTGCCTGGTCAAGGACTACTTCCCCGAACCGGTGACGGTGT
CGTGGAACTCAGGCGCCCTGACCAGCGGCGTGCACACCTTCCCGGCTGTCCTACAGTCCT
CAGGACTCTACTCCCTCAGCAGCGTGGTGACCGTGCCCTCCAGCAGCTTGGGCACCCAGA
CCTACATCTGCAACGTGAATCACAAGCCCAGCAACACCAAGGTCGACAAGAAAGTTGAGC
CCAAATCTTGTGACAAAACTCACCTC
```

FIG. 18B

DIQLTQSPSSLSASVGDRVTITCSASQDISNYLNWYQQKPGKAPKVLIYFTSSLHSGVPS
RFSGSGSGTDFTLTISSLQPEDFATYYCQQYSTVPWTFGQGTKVEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC

*FIG. 21A*

EVQLVESGGGLVQPGGSLRLSCAASGYDFTHYGMNWVRQAPGKGLEWVGWINTYTGEPTY
AADFKRRFTFSLDTSKSTAYLQMNSLRAEDTAVYYCAKYPYYGTSHWYFDVWGQGTLVT
VSSASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHL

*FIG. 21B*

DIQVTQSPSSLSASVGDRVTITCITSTDIDDDMNWYQQKPGKVPKLLISGGNTLRPGVPS
RFSGSGSGTDFTLTISSLQPEDVATYYCLQSDSLPYTFGQGTKVEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC

*FIG. 22A*

EVQLVQSGPELKKPGASVKVSCKASGYTFTNYGMNWVRQAPGQGLEWMGWINTYTGETTY
ADDFKGRFVFSLDTSVSTAYLQISSLKAEDTAVYYCEREGGVNNWGQGTLVTVSSASTKG
PSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHT

*FIG. 22B*

DIQMTQSPSSLSASVGDRVTITCKSSQSLLYTSSQKNYLAWYQQKPGKAPKLLIYWASTR
ESGVPSRFSGSGSGTDFTLTISSLQPEDFATYYCQQYYAYPWTFGQGTKVEIKRTVAAPS
VFIFPPSDEQLKSGTASVVCLLNNFYPREAKVQWKVDNALQSGNSQESVTEQDSKDSTYS
LSSTLTLSKADYEKHKVYACEVTHQGLSSPVTKSFNRGEC

*FIG. 23A*

EVQLVESGGGLVQPGGSLRLSCAASGYTFTSYWLHWVRQAPGKGLEWVGMIDPSNSDTRF
NPNFKDRFTISADTSKNTAYLQMNSLRAEDTAVYYCATYRSYVTPLDYWGQGTLVTVSSA
STKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGP
SVFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSREEM
TKNQVSLSCAVKGFYPSDIAVEWESNGQPENNYKTTPPVLDSDGSFFLVSKLTVDKSRWQ
QGNVFSCSVMHEALHNHYTQKSLSLSPGK

*FIG. 23B*

DKTHTCPPCPAPELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTISKAK
GQPREPQVYTLPPSREEMTKNQVSLWCLVKGFYPSDIAVEWESNGQPENNYKTTPPVLDS
DGSFFLYSKLTVDKSRWQQGNVFSCSVMHEALHNHYTQKSLSLSPGK

*FIG. 23C*

METHODS FOR REDUCING NORLEUCINE MISINCORPORATION INTO PROTEINS USING A MICROORGANISM COMPRISING A MUTANT META ALLELE

RELATED APPLICATIONS

This application is a divisional of U.S. patent application Ser. No. 15/816,305, filed on 17 Nov. 2017, now U.S. Pat. No. 10,179,925, which is a divisional of U.S. patent application Ser. No. 15/067,646, filed on 11 Mar. 2016, now U.S. Pat. No. 9,850,514, which is a continuation of U.S. patent application Ser. No. 14/031,463, filed on 19 Sep. 2013, abandoned, which claims the benefit of U.S. Provisional Application No. 61/777,700, filed on 12 Mar. 2013, expired, and U.S. Provisional Application No. 61/703,142, filed on 19 Sep. 2012, expired, each of which is incorporated by reference herein in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392043110seqlist.txt, date recorded: Apr. 11, 2018, size: 45 KB).

FIELD OF THE INVENTION

The present invention relates to methods and compositions for preventing misincorporation of norleucine into proteins during recombinant protein production in bacteria. The present invention also provides microorganism host cells and nucleic acid molecules for use with the methods and compositions provided herein.

BACKGROUND

Norleucine, an analog of the amino acid methionine, can be misincorporated into proteins in place of methionine residues. When expressed in *Escherichia coli* (*E. coli*), many heterologous proteins have norleucine mistakenly incorporated in places where methionine residues should appear. The misincorporation of norleucine in proteins, in particular in heterologous proteins produced by recombinant means, is generally considered undesirable due, in part, to the resulting production of altered proteins having undesirable characteristics.

Misincorporation of norleucine at methionine positions during recombinant protein production in *E. coli* has been observed for over 50 years. (See, e.g., Munier and Cohen (1959) Biochim Biophys Acta 31:378-391; Cohen and Munier (1956) Biochim Biophys Acta 21:592-593; Cohen and Munier (1959) Biochim Biophys Acta 31:347-356; and Cowie et al., (1959) Biochim Biophys Acta 34:39-46.) For example, approximately 14% of methionine residues in methionyl bovine somatotropin (MBS) exhibited norleucine misincorporation during recombinant production of this protein in *E coli*, and approximately 6% of the methionine residues in native *E. coli* proteins were also substituted with norleucine. (See Bogosian et al., (1989) J Biol Chem 264: 531-9.) In another example, production of interleukin-2 in a minimal medium *E. coli* fermentation resulted in approximately 19% of the methionine residues in the recombinant protein were substituted with norleucine. (See Tsai et al., (1988) Biochem Biophys Res Commun 156:733-739.) Other studies showed that norleucine residue misincorporation into protein can occur both at internal methionine residues and at the amino terminal methionine residue. (See Brown (1973) Biochim Biophys Acta 294:527-529; and Barker and Bruton (1979) J Mol Biol 133:217-231.)

Norleucine competes with methionine for incorporation into proteins due to the promiscuous nature of the enzyme methionyl tRNA synthetase (MetG). (See Trupin et al., (1966) Biochem Biophys Res Commun 24:50-55; and Fersht and Dingwall (1979) Biochemistry 18:1250-1256.) Kinetic studies with *E. coli* MetG enzyme showed that acylation of MetG is approximately 4-fold higher with methionine compared to that with norleucine. (See van Hest et al., (2000) Am Chem Soc 122:1282-1288.) Due to the relaxed substrate specificity of MetG, norleucine can substitute for methionine in the acylation reaction, resulting in misincorporation of norleucine into proteins in place of methionine.

Misincorporation of norleucine residues for methionine residues in recombinant protein production is generally considered undesirable. Recombinant proteins or polypeptides containing misincorporated norleucine residues may exhibit altered structural and functional features, such as, for example, altered sensitivity to proteolysis, diminished biological activity, or increased immunogenicity.

Various strategies have been developed to reduce or prevent norleucine misincorporation during recombinant protein production. For example, supplementing cell culture medium with methionine during the fermentation process (by continuous or bolus feed/addition of methionine) has been used to ensure that excess methionine is available to the cells, thus reducing the probability of an incorrect charging of the methionyl tRNA with norleucine. (See, e.g., U.S. Pat. No. 5,599,690.) While continuous or bolus feed/addition of methionine reduced the extent of norleucine misincorporation in recombinant proteins, the operational complexity and cost of the fermentation process may increase. Furthermore, continuous or bolus feed/addition of methionine during fermentation may lead to undesirable dilution of the fermentor contents, resulting in lower cell densities and lower product yields.

Deleting genes involved in the norleucine biosynthetic pathway such as, for example, deleting genes of the leucine operon (leuA, leuB, leuC and leuD) or deleting transaminase encoding genes such as ilvE or tyrB, has also been used to reduce norleucine misincorporation in proteins (See Bogosian et al., (1989) J Biol Chem 264:531-539; Tsai et al., (1989) Biochem Biophys Res Commun 156:733-739; and Randhawa et al., (1994) Biochemistry 33:4352-4362.) The deletion of biosynthetic pathway genes to prevent norleucine misincorporation, however, may require addition of other amino acids (such as leucine or isoleucine) to the culture medium during fermentation as many genes involved in norleucine biosynthesis are also involved in biosynthesis of branched chain amino acids. (See Bogosian et al., (1989) J Biol Chem 264:531-539, see FIG. 8 of the instant specification.)

Another strategy used to prevent norleucine misincorporation involved co-expression of enzymes which degrade norleucine, including, for example, amino acid dehydrogenases and amino acid oxidases. This approach, however, required overexpression of these enzymes, which may not be desirable during recombinant protein production, and may lead to lower recombinant protein yields. (See e.g., United States Patent Application Publication No. US2007/0009995.) In addition, over expression of these enzymes may result in degradation of other analogous amino acids during the fermentation process. Altering the primary amino acid sequence of the polypeptide to be expressed by substituting methionine codons with other codons was also performed to prevent norleucine misincorporation. (See e.g., U.S. Pat. No. 5,698,418.) Such substitutions, however, may lead to diminished activity or structural changes in the resulting protein, a highly undesirable outcome for recombinant protein production in the biotechnology industry.

As noted above, current methods used to prevent norleucine misincorporation during recombinant protein production in microorganisms are associated with various disadvantages; therefore, a need exists for novel methods useful for preventing or reducing norleucine misincorporation in to proteins, in particular during recombinant protein production in microorganisms, such as E. coli.

The present invention meets this need by providing engineered microorganism host cells effective at preventing norleucine misincorporation during recombinant protein production in microorganisms, such as, for example, bacteria. The present invention provides, inter alia, E. coli host cells comprising mutated metA and metK alleles (i.e., altered metA and metK nucleic acid sequences) which result in methionine production by the microorganism to a degree or extent sufficient to reduce or prevent norleucine misincorporation into proteins and polypeptides. Analysis of recombinant proteins produced utilizing such host cells showed that misincorporation of norleucine residues in place of methionine residues was eliminated. The present invention further demonstrates that fermentation process performance using such E. coli host cells, including growth of the host cells and recombinant protein product titers utilizing such E. coli host cells, was comparable to that observed in control host cells.

SUMMARY OF THE INVENTION

The present invention provides, in part, methods and compositions for preventing or reducing norleucine misincorporation into proteins and polypeptides. The methods and compositions of the present invention are useful for preventing or reducing norleucine misincorporation in heterologous (e.g., recombinant) proteins and polypeptides expressed by a microorganism, such as, for example, bacteria (e.g., E. coli).

In some embodiments, the present invention provides methods for preventing or reducing norleucine misincorporation into a protein or polypeptide expressed by a microorganism, wherein the microorganism produces methionine to a degree or extent sufficient to prevent or reduce norleucine misincorporation into the protein or polypeptide. In some embodiments, the microorganism is a feedback-resistant or feedback-insensitive homoserine succinyltransferase microorganism. In other embodiments, the microorganism is a microorganism comprising a mutant metA allele, a mutant metK allele, or a mutant metA allele and a mutant metK allele.

In some embodiments, the present invention provides methods for reducing or preventing norleucine misincorporation in a protein or polypeptide, the method comprising expressing the protein or polypeptide in a microorganism, wherein the microorganism comprises a mutant metA allele, wherein the mutant metA allele comprises a nucleic acid sequence encoding an amino acid substitution in MetA selected from the group consisting of an arginine to cysteine substitution at amino acid position 27, a glutamine to glutamic acid substitution at amino acid position 64, a tyrosine to cysteine substitution at amino acid position 294, an isoleucine to serine substitution at amino acid position 296, and a proline to leucine substitution at amino acid position 298. In some embodiments, the mutant metA allele comprises a nucleic acid sequence encoding amino acid substitutions in MetA comprising an isoleucine to serine substitution at amino acid position 296 and a proline to leucine substitution at amino acid position 298. MetA amino acid positions described herein in the instant specification are in reference to wild-type MetA amino acid sequence as shown in FIG. 7A and SEQ ID NO:29.

In other embodiments, the present invention provides methods for reducing or preventing norleucine misincorporation in a protein or polypeptide, the method comprising expressing the protein or polypeptide in a microorganism, wherein the microorganism comprises a mutant metA allele, wherein the mutant metA allele comprises a nucleic acid sequence selected from the group consisting of SEQ ID NO:23, SEQ ID NO:24, SEQ ID NO:25, and SEQ ID NO:26.

As stated above, the present invention provides methods for preventing or reducing norleucine misincorporation into a protein or polypeptide expressed by a microorganism, wherein the microorganism produces methionine to a degree or extent sufficient to prevent or reduce norleucine misincorporation into the protein or polypeptide. In other embodiments, the present invention provides methods for reducing or preventing norleucine misincorporation in a protein or polypeptide expressed by a microorganism, the method comprising expressing the protein or polypeptide in the microorganism, wherein the microorganism is a microorganism de-repressed for methionine production. In some embodiments, the microorganism is de-repressed for methionine production due to partial loss-of-function of S-adenosylmethionine synthase. In other embodiments, the present invention provides methods for reducing or preventing norleucine misincorporation in a protein or polypeptide expressed by a microorganism, the method comprising expressing the protein or polypeptide in the microorganism, wherein the microorganism comprises a mutant metK allele. In some embodiments, the mutant metK allele results in a partial loss-of-function of MetK.

In some embodiments, the present invention provides methods for reducing or preventing norleucine misincorporation in a protein or polypeptide, the method comprising expressing the protein or polypeptide in a microorganism, wherein the microorganism comprises a mutant metK allele, wherein the mutant metK allele comprises a nucleic acid sequence encoding an amino acid substitution in MetK comprising a valine to glutamic acid substitution at amino acid position 185. In other embodiments, the present invention provides methods for reducing or preventing norleucine misincorporation in a protein or polypeptide, the method comprising expressing the protein or polypeptide in a microorganism, wherein the microorganism comprises a mutant metK allele, wherein the mutant metK allele comprises a nucleic acid sequence comprising a deletion of the cytosine base at nucleic acid residue position 1132 of the metK allele. MetK amino acid positions described herein in the instant specification are in reference to wild-type MetK amino acid sequence as shown in FIG. 8A and SEQ ID NO:30. metK nucleic acid positions described herein in the instant specification are in reference to wild-type metK nucleic acid sequence as shown in FIG. 8B and SEQ ID NO:32.

In some embodiments, the present invention provides methods for reducing or preventing norleucine misincorporation in a protein or polypeptide, the method comprising expressing the protein or polypeptide in a microorganism, wherein the microorganism comprises a mutant metK allele, wherein the mutant metK allele comprises a nucleic acid sequence selected from the group consisting of SEQ ID NO:27 and SEQ ID NO:28.

In other embodiments, the present invention provides methods for reducing or preventing norleucine misincorporation in a protein or polypeptide, the method comprising expressing the protein or polypeptide in a microorganism, wherein the microorganism comprises a mutant metA allele and a metK allele. In some embodiments, the mutant metA allele comprises a nucleic acid sequence encoding a tyrosine to cysteine substitution at amino acid position 294 of MetA and the mutant metK allele comprises a nucleic acid sequence encoding a valine to glutamic acid substitution at amino acid position 185 of MetK. In other embodiments, the present invention provides methods for reducing or preventing norleucine misincorporation in a protein or polypeptide, the method comprising expressing the protein or polypeptide in a microorganism, wherein the microorganism comprises a mutant metA allele and a metK allele, wherein the mutant metA allele comprises a nucleic acid sequence encoding a tyrosine to cysteine substitution at amino acid position 294 of MetA, and wherein the mutant metK allele comprises a nucleic acid sequence comprising a deletion of the cytosine base at nucleic acid residue position 1132 of the metK allele.

In other embodiments, the present invention provides methods for reducing or preventing norleucine misincorporation in a protein or polypeptide, the method comprising expressing the protein or polypeptide in a microorganism, wherein the microorganism comprises a mutant metA allele and a mutant metK allele, and wherein the mutant metA allele comprises the nucleic acid sequence of SEQ ID NO:24, and the mutant metK allele comprises the nucleic acid sequence of SEQ ID NO:27. In yet other embodiments, the present invention provides methods for reducing or preventing norleucine misincorporation in a protein or polypeptide, the method comprising expressing the protein or polypeptide in a microorganism, wherein the microorganism comprises a mutant metA allele and a mutant metK allele, wherein the mutant metA allele comprises the nucleic acid sequence of SEQ ID NO:24, and the mutant metK allele comprises the nucleic acid sequence of SEQ ID NO:28.

The present invention further provides microorganism host cells useful for preventing or reducing norleucine misincorporation into proteins and polypeptides expressed by a microorganism host cell. The present invention also provides microorganism host cells for use in the expression of proteins or polypeptides by the microorganism host cell, wherein the expressed proteins or polypeptides are free of norleucine misincorporation. In some embodiments, the microorganism host cell is a bacterium. In other embodiments, the microorganism host cell is E. coli.

The present invention provides a microorganism (e.g., a microorganism host cell), wherein the microorganism produces methionine to a degree or extent sufficient to prevent or reduce norleucine misincorporation into proteins or polypeptides expressed by the microorganism. In some embodiments, the present invention provides a microorganism, wherein the microorganism is a feedback-insensitive homoserine succinyltransferase microorganism. In other embodiments, the present invention provides a microorganism comprising a mutant metA allele. In some embodiments, the present invention provides a microorganism comprising a mutant metA allele, wherein the mutant metA allele comprises a nucleic acid sequence encoding an amino acid substitution in MetA selected from the group consisting of an arginine to cysteine substitution at amino acid position 27, a glutamine to glutamic acid substitution at amino acid position 64, a tyrosine to cysteine substitution at amino acid position 294, an isoleucine to serine substitution at amino acid position 296, and a proline to leucine substitution at amino acid position 298. In some embodiments, the microorganism host cell is a bacterium. In other embodiments, the microorganism host cell is E. coli.

In some embodiments, the present invention provides a microorganism comprising a mutant metA allele, wherein the mutant metA allele comprises a nucleic acid sequence encoding more than one amino acid substitution in MetA. In some embodiments, the mutant metA allele comprises a nucleic acid sequence encoding an isoleucine to serine substitution at amino acid position 296 in MetA and a proline to leucine substitution at amino acid position 298 in MetA. In some embodiments, the microorganism host cell is a bacterium. In other embodiments, the microorganism host cell is E. coli.

In some embodiments, the present invention provides a microorganism, wherein the microorganism comprises a mutant metA allele, wherein the mutant metA allele comprises a nucleic acid sequence selected from the group consisting of SEQ ID NO:23, SEQ ID NO:24, SEQ ID NO:25, and SEQ ID NO:26. In some embodiments, the microorganism host cell is a bacterium. In other embodiments, the microorganism host cell is E. coli.

The present invention provides a microorganism (e.g., a microorganism host cell), wherein the microorganism produces methionine to a degree or extent sufficient to prevent or reduce norleucine misincorporation into proteins or polypeptides expressed by the microorganism. In some embodiments, the present invention provides a microorganism, wherein the microorganism is a microorganism de-repressed for methionine production. In some aspects, the microorganism de-repressed for methionine production results from a partial loss-of-function of S-adenosylmethionine synthase. In other embodiments, the present invention provides a microorganism comprising a mutant metK allele. In some embodiments, the present invention provides a microorganism comprising a mutant metK allele, wherein the mutant metK allele comprises a nucleic acid sequence encoding an amino acid substitution in MetK comprising a valine to glutamic acid substitution at amino acid position 185. In other embodiments, the present invention provides a microorganism comprising a mutant metK allele, wherein the mutant metK allele comprises a nucleic acid sequence comprising a deletion of the cytosine base at nucleic acid residue position 1132 in the metK allele. In some embodiments, the microorganism host cell is a bacterium. In other embodiments, the microorganism host cell is E. coli.

In some embodiments, the present invention provides a microorganism, wherein the microorganism comprises a mutant metK allele, wherein the mutant metK allele comprises a nucleic acid sequence selected from the group consisting of SEQ ID NO:27 and SEQ ID NO:28. In some embodiments, the microorganism host cell is a bacterium. In other embodiments, the microorganism host cell is E. coli.

The present invention also provides microorganism host cells comprising various combinations of mutant metA alleles and a mutant metK alleles. In some embodiments, the present invention provides a microorganism comprising a mutant metA allele and a mutant metK allele, wherein the mutant metA allele comprises a nucleic acid sequence encoding an amino acid substitution in MetA comprising a tyrosine to cysteine substitution at amino acid position 294, and wherein the mutant metK allele comprises a nucleic acid sequence encoding an amino acid substitution in MetK comprising a valine to glutamic acid substitution at amino acid position 185. In other embodiments, the present invention provides a microorganism comprising a mutant metA allele and a mutant metK allele, wherein the mutant metA allele comprises a nucleic acid sequence encoding an amino acid substitution in MetA comprising a tyrosine to cysteine substitution at amino acid position 294, and wherein the mutant metK allele comprises a deletion of the nucleic acid cytosine at nucleic acid residue 1132 of the metK allele. In some embodiments, the present invention provides a microorganism, wherein the microorganism comprises a mutant metA allele and a mutant metK allele, wherein the mutant metA allele comprises the nucleic acid sequence of SEQ ID NO:24, and wherein the mutant metK allele comprises the nucleic acid sequence of SEQ ID NO 27. In other embodiments, the present invention provides a microorganism, wherein the microorganism comprises a mutant metA allele and a mutant metK allele, wherein the mutant metA allele comprises the nucleic acid sequence of SEQ ID NO:24, and wherein the mutant metK allele comprises the nucleic acid sequence of SEQ ID NO:28. In some embodiments, the microorganism host cell is a bacterium. In other embodiments, the microorganism host cell is *E. coli*.

The present invention also provides isolated nucleic acid molecules for use in the present methods. In some aspects, the present invention provides isolated metA nucleic acid molecules (i.e., isolated nucleic acid molecules encoding MetA). In some embodiments, the present invention provides an isolated metA nucleic acid molecule, wherein the metA nucleic acid molecule comprises a nucleic acid sequence encoding an amino acid substitution in MetA selected from the group consisting of an arginine to cysteine substitution in at amino acid position 27, a glutamine to glutamic acid substitution at amino acid position 64, a tyrosine to cysteine substitution at amino acid position 294, an isoleucine to serine substitution at amino acid position 296, and a proline to leucine substitution at amino acid position 298. In other embodiments, an isolated metA nucleic acid molecule provided by the present invention comprises a nucleic acid sequence selected from the group consisting of SEQ ID NO:23, SEQ ID NO:24, SEQ ID NO:25, and SEQ ID NO:26. The use of these isolated metA nucleic acid molecules and sequences thereof for the production of microorganisms for use in preventing or reducing norleucine misincorporation in proteins or polypeptides is specifically provided herein by the present invention.

The present invention also provides isolated metK nucleic acid molecules (i.e., isolated nucleic acid molecules encoding MetK). In some embodiments, the present invention provides a metK nucleic acid molecule, wherein the metK nucleic acid molecule comprises a nucleic acid sequence encoding an amino acid substitution in MetK comprising a valine to glutamic acid substitution at amino acid position 185. In other embodiments, the present invention provides a metK nucleic acid molecule, wherein the metK nucleic acid molecule comprises a deletion of the nucleic acid cytosine at nucleic acid residue 1132 of the metK allele. In other embodiments, a metK nucleic acid molecule provided by the present invention comprises a nucleic acid sequence selected from the group consisting of SEQ ID NO:27 and SEQ ID NO:28. The use of these isolated metK nucleic acid molecules and sequences thereof for the production of microorganisms for use in preventing or reducing norleucine misincorporation in proteins or polypeptides is specifically provided herein by the present invention.

The present invention provides a microorganism comprising a nucleic acid comprising a mutant metA allele, wherein the microorganism further comprises nucleic acid encoding an anti-VEGF antibody or an anti-VEGF antibody fragment. In some embodiments, the present invention provides a microorganism comprising a nucleic acid comprising a mutant metA allele, wherein the microorganism further comprises a nucleic acid encoding the amino acid sequence of SEQ ID NO: 46 and a nucleic acid encoding the amino acid sequence of SEQ ID NO. 47. In some embodiments, the nucleic acid encoding the amino acid sequence of SEQ ID NO:46 is the nucleic acid sequence of SEQ ID NO:33. In some embodiments, the nucleic acid sequence encoding the amino acid sequence of SEQ ID NO:47 is the nucleic acid sequence of SEQ ID NO:34. In some embodiments, the present invention provides a microorganism comprising a nucleic acid comprising a mutant metA allele, wherein the microorganism further comprises a nucleic acid having the nucleic acid sequence corresponding to SEQ ID NO:33 and a nucleic acid having the nucleic acid sequence corresponding to SEQ ID NO:34. In some embodiments, the mutant metA allele comprises a nucleic acid sequence selected from the group consisting of SEQ ID NO:23, SEQ ID NO:24, SEQ ID NO:25, and SEQ ID NO:26. In some aspects, the microorganism is a bacteria, e.g., *E. coli*.

The present invention provides a microorganism comprising a nucleic acid comprising a mutant metK allele, wherein the microorganism further comprises nucleic acid encoding an anti-VEGF antibody or an anti-VEGF antibody fragment. In some embodiments, the present invention provides a microorganism comprising a nucleic acid comprising a mutant metK allele, wherein the microorganism further comprises a nucleic acid encoding the amino acid sequence of SEQ ID NO: 46 and a nucleic acid encoding the amino acid sequence of SEQ ID NO: 47. In some embodiments, the nucleic acid encoding the amino acid sequence of SEQ ID NO:46 is the nucleic acid sequence of SEQ ID NO:33. In some embodiments, the nucleic acid sequence encoding the amino acid sequence of SEQ ID NO:47 is the nucleic acid sequence of SEQ ID NO:34. In some embodiments, the present invention provides a microorganism comprising a nucleic acid comprising a mutant metK allele, wherein the microorganism further comprises a nucleic acid having the nucleic acid sequence corresponding to SEQ ID NO:33 and a nucleic acid having the nucleic acid sequence corresponding to SEQ ID NO:34. In some embodiments, the mutant metK allele comprises a nucleic acid sequence selected from the group consisting of SEQ ID NO:27 and SEQ ID NO:28. In some aspects, the microorganism is a bacteria, e.g., *E. coli*.

The present invention provides a microorganism comprising a nucleic acid comprising a mutant metA allele and a mutant metK allele, wherein the microorganism further comprises nucleic acid encoding an anti-VEGF antibody or an anti-VEGF antibody fragment. In some embodiments, the present invention provides a microorganism comprising a nucleic acid comprising a mutant metA allele and a mutant metK allele, wherein the microorganism further comprises a nucleic acid encoding the amino acid sequence of SEQ ID NO: 46 and a nucleic acid encoding the amino acid sequence of SEQ ID NO: 47. In some embodiments, the nucleic acid encoding the amino acid sequence of SEQ ID NO:46 is the nucleic acid sequence of SEQ ID NO:33. In some embodiments, the nucleic acid sequence encoding the amino acid sequence of SEQ ID NO:47 is the nucleic acid sequence of SEQ ID NO:34. In some embodiments, the present invention provides a microorganism comprising a nucleic acid comprising a mutant metA allele and a mutant metK allele, wherein the microorganism further comprises a nucleic acid having the nucleic acid sequence corresponding to SEQ ID NO:33 and a nucleic acid having the nucleic acid sequence corresponding to SEQ ID NO:34. In some embodiments, the mutant metA allele comprises a nucleic acid sequence selected from the group consisting of SEQ ID NO:23, SEQ ID NO:24, SEQ ID NO:25, and SEQ ID NO:26, and the mutant metK allele comprises a nucleic acid sequence selected from the group consisting of SEQ ID NO:27 and SEQ ID NO:28. In some aspects, the microorganism is a bacteria, e.g., *E. coli*.

The present invention provides a microorganism comprising a nucleic acid comprising a mutant metA allele, wherein the microorganism further comprises nucleic acid encoding an anti-Factor D antibody or an anti-Factor D antibody fragment. In some embodiments, the present invention provides a microorganism comprising a nucleic acid comprising a mutant meld allele, wherein the microorganism further comprises a nucleic acid encoding the amino acid sequence of SEQ ID NO: 48 and a nucleic acid encoding the amino acid sequence of SEQ ID NO: 49. In some embodiments, the mutant metA allele comprises a nucleic acid sequence selected from the group consisting of SEQ ID NO:23, SEQ ID NO:24, SEQ ID NO:25, and SEQ ID NO:26. In some aspects, the microorganism is a bacteria, e.g., *E. coli*.

The present invention provides a microorganism comprising a nucleic acid comprising a mutant metK allele, wherein the microorganism further comprises nucleic acid encoding an anti-Factor D antibody or an anti-Factor D antibody fragment. In some embodiments, the present invention provides a microorganism comprising a nucleic acid comprising a mutant metK allele, wherein the microorganism further comprises a nucleic acid encoding the amino acid sequence of SEQ ID NO: 48 and a nucleic acid encoding the amino acid sequence of SEQ ID NO: 49. In some embodiments, the mutant metK allele comprises a nucleic acid sequence selected from the group consisting of SEQ ID NO:27 and SEQ ID NO:28. In some aspects, the microorganism is a bacteria, e.g., *E. coli*.

The present invention provides a microorganism comprising a nucleic acid comprising a mutant metA allele and a mutant metK allele, wherein the microorganism further comprises nucleic acid encoding an anti-Factor D antibody or an anti-Factor D antibody fragment. In some embodiments, the present invention provides a microorganism comprising a nucleic acid comprising a mutant metA allele and a mutant metK allele, wherein the microorganism further comprises a nucleic acid encoding the amino acid sequence of SEQ ID NO: 48 and a nucleic acid encoding the amino acid sequence of SEQ ID NO: 49. In some embodiments, the mutant metA allele comprises a nucleic acid sequence selected from the group consisting of SEQ ID NO:23, SEQ ID NO:24, SEQ ID NO:25, and SEQ ID NO:26, and the mutant metK allele comprises a nucleic acid sequence selected from the group consisting of SEQ ID NO:27 and SEQ ID NO:28. In some aspects, the microorganism is a bacteria, e.g., *E. coli*.

The present invention provides a microorganism comprising a nucleic acid comprising a mutant metA allele, wherein the microorganism further comprises nucleic acid encoding an anti-MET antibody or an anti-MET antibody fragment. In some embodiments, the present invention provides a microorganism comprising a nucleic acid comprising a mutant metA allele, wherein the microorganism further comprises a nucleic acid encoding the amino acid sequence of SEQ ID NO: 50, a nucleic acid encoding the amino acid sequence of SEQ ID NO: 51, and a nucleic acid encoding the amino acid sequence of SEQ ID NO:52. In some embodiments, the mutant metA allele comprises a nucleic acid sequence selected from the group consisting of SEQ ID NO:23, SEQ ID NO:24, SEQ ID NO:25, and SEQ ID NO:26. In some aspects, the microorganism is a bacteria, e.g., *E. coli*.

The present invention provides a microorganism comprising a nucleic acid comprising a mutant metK allele, wherein the microorganism further comprises nucleic acid encoding an anti-MET antibody or an anti-MET antibody fragment. In some embodiments, the present invention provides a microorganism comprising a nucleic acid comprising a mutant metK allele, wherein the microorganism further comprises a nucleic acid encoding the amino acid sequence of SEQ ID NO: 50, a nucleic acid encoding the amino acid sequence of SEQ ID NO: 51, and a nucleic acid encoding the amino acid sequence of SEQ ID NO:52. In some embodiments, the mutant metK allele comprises a nucleic acid sequence selected from the group consisting of SEQ ID NO:27 and SEQ ID NO:28. In some aspects, the microorganism is a bacteria, e.g., *E. coli*.

The present invention provides a microorganism comprising a nucleic acid comprising a mutant metA allele and a mutant metK allele, wherein the microorganism further comprises nucleic acid encoding an anti-MET antibody or an anti-MET antibody fragment. In some embodiments, the present invention provides a microorganism comprising a nucleic acid comprising a mutant metA allele and a mutant metK allele, wherein the microorganism further comprises a nucleic acid encoding the amino acid sequence of SEQ ID NO: 50, a nucleic acid encoding the amino acid sequence of SEQ ID NO: 51, and a nucleic acid encoding the amino acid sequence of SEQ ID NO:52. In some embodiments, the mutant metA allele comprises a nucleic acid sequence selected from the group consisting of SEQ ID NO:23, SEQ ID NO:24, SEQ ID NO:25, and SEQ ID NO:26, and the mutant metK allele comprises a nucleic acid sequence selected from the group consisting of SEQ ID NO:27 and SEQ ID NO:28. In some aspects, the microorganism is a bacteria, e.g., *E. coli*.

The present invention further provides a method for producing in a bacteria host cell a protein or a polypeptide free of norleucine misincorporation, the method comprising expressing in the bacteria host cell a nucleic acid encoding the protein or the polypeptide, wherein the bacteria host cell comprises a mutant metA allele, a mutant metK allele, or a mutant metA allele and a mutant metK allele, thereby producing a protein or polypeptide free of norleucine misincorporation. In some embodiments, the mutant metA allele comprises a nucleic acid sequence selected from the group consisting of SEQ ID NO:23, SEQ ID NO:24, SEQ ID NO:25, and SEQ ID NO:26, and the mutant metK allele comprises a nucleic acid sequence selected from the group consisting of SEQ ID NO:27 and SEQ ID NO:28.

The present invention also provides a method for producing an antibody or an antibody fragment in a bacteria host cell, wherein the antibody or the antibody fragment is free of norleucine misincorporation, the method comprising expressing in the bacteria host cell a nucleic acid encoding the antibody or the antibody fragment, wherein the bacteria host cell comprises a mutant metA allele, a mutant metK allele, or a mutant metA allele and a mutant metK allele, thereby producing an antibody or an antibody fragment free of norleucine misincorporation. In some aspects, the method for producing an antibody or an antibody fragment in a bacteria host cell free of norleucine misincorporation according to the present invention comprises expressing in the bacteria host cell a nucleic acid encoding an antibody heavy chain polypeptide and a nucleic acid encoding an antibody light chain polypeptide. In some aspects, the antibody heavy chain polypeptide is an antibody Fab fragment heavy chain polypeptide, and the antibody light chain polypeptide is an antibody Fab fragment light chain polypeptide. In some embodiments, the mutant metA allele comprises a nucleic acid sequence selected from the group consisting of SEQ ID NO:23, SEQ ID NO:24, SEQ ID NO:25, and SEQ ID NO:26, and the mutant metK allele comprises a nucleic acid sequence selected from the group consisting of SEQ ID NO:27 and SEQ ID NO:28.

In some embodiments, the present invention provides a method for producing an anti-VEGF antibody or an anti-VEGF antibody fragment in a bacterial host cell, wherein the anti-VEGF antibody or the anti-VEGF antibody fragment is free of norleucine misincorporation, the method comprising expressing in the bacteria host cell a nucleic acid encoding the anti-VEGF antibody or the anti-VEGF antibody fragment, wherein the bacteria host cell comprises a mutant metA allele, a mutant metK allele, or a mutant metA allele and a mutant metK allele, thereby producing an anti-VEGF antibody or an anti-VEGF antibody fragment free of norleucine misincorporation. In some embodiments, the method comprises expressing in the bacteria host cell a nucleic acid encoding an anti-VEGF antibody heavy chain polypeptide or an anti-VEGF antibody fragment heavy chain polypeptide or fragment thereof and a nucleic acid encoding an anti-VEGF antibody light chain polypeptide or an anti-VEGF antibody fragment light chain polypeptide or fragment thereof. In some aspects, the anti-VEGF antibody heavy chain and the anti-VEGF antibody light chain are full-length heavy chain and light chain anti-VEGF antibody polypeptides. In other aspects, the anti-VEGF antibody heavy chain is an antibody Fab fragment heavy chain polypeptide, and the anti-VEGF antibody light chain is an antibody Fab fragment light chain polypeptide. In some embodiments, the anti-VEGF antibody heavy chain comprises the amino acid sequence of SEQ ID NO:47 and the anti-VEGF antibody light chain comprises the amino acid sequence of SEQ ID NO:46. In some embodiments, the nucleic acid encoding the amino acid sequence of SEQ ID NO:47 is the nucleic acid sequence of SEQ ID NO:34. In some embodiments, the nucleic acid sequence encoding the amino acid sequence of SEQ ID NO:46 is the nucleic acid sequence of SEQ ID NO:33 In some embodiments, the mutant metA allele comprises a nucleic acid sequence selected from the group consisting of SEQ ID NO:23, SEQ ID NO:24, SEQ ID NO:25, and SEQ ID NO:26. In some embodiments, the mutant metK allele comprises a nucleic acid sequence selected from the group consisting of SEQ ID NO:27 and SEQ ID NO 28.

The invention further provides an anti-VEGF antibody or anti-VEGF antibody fragment produced by any of the methods described herein, wherein the anti-VEGF antibody or anti-VEGF antibody fragment is free of norleucine misincorporation.

In some embodiments, the present invention provides a method for producing an anti-Factor D antibody or an anti-Factor D antibody fragment in a bacterial host cell, wherein the anti-Factor D antibody or the anti-Factor D antibody fragment is free of norleucine misincorporation, the method comprising expressing in the bacteria host cell a nucleic acid encoding the anti-Factor D antibody or the anti-Factor D antibody fragment, wherein the bacteria host cell comprises a mutant metA allele, a mutant metK allele, or a mutant metA allele and a mutant metK allele, thereby producing an anti-Factor D antibody or an anti-Factor D antibody fragment free of norleucine misincorporation. In some embodiments, the method comprises expressing in the bacteria host cell a nucleic acid encoding an anti-Factor D antibody heavy chain polypeptide or an anti-Factor antibody fragment heavy chain polypeptide or fragment thereof and a nucleic acid encoding an anti-Factor D antibody light chain polypeptide or an anti-Factor D antibody fragment light chain polypeptide or fragment thereof. In some aspects, the anti-Factor D antibody heavy chain and the anti-Factor D antibody light chain are full-length heavy chain and light chain anti-Factor D antibody polypeptides. In other aspects, the anti-Factor D antibody heavy chain is an antibody Fab fragment heavy chain polypeptide, and the anti-Factor D antibody light chain is an antibody Fab fragment light chain polypeptide. In some embodiments, the anti-Factor D antibody heavy chain comprises the amino acid sequence of SEQ ID NO:49 and the anti-Factor D antibody light chain comprises the amino acid sequence of SEQ ID NO:48. In some embodiments, the mutant metA allele comprises a nucleic acid sequence selected from the group consisting of SEQ ID NO:23, SEQ ID NO:24, SEQ ID NO:25, and SEQ ID NO:26. In some embodiments, the mutant metK allele comprises a nucleic acid sequence selected from the group consisting of SEQ ID NO:27 and SEQ ID NO:28.

The invention further provides an anti-Factor D antibody or anti-Factor D antibody fragment produced by any of the methods described herein, wherein the anti-Factor D antibody or anti-Factor D antibody fragment is free of norleucine misincorporation.

In some embodiments, the present invention provides a method for producing an anti-MET antibody or an anti-MET antibody fragment in a bacterial host cell, wherein the anti-MET antibody or the anti-MET antibody fragment is free of norleucine misincorporation, the method comprising expressing in the bacteria host cell a nucleic acid encoding the anti-MET antibody or the anti-MET antibody fragment, wherein the bacteria host cell comprises a mutant metA allele, a mutant metK allele, or a mutant metA allele and a mutant metK allele, thereby producing an anti-MET antibody or an anti-MET antibody fragment free of norleucine misincorporation. In some embodiments, the method comprises expressing in the bacteria host cell a nucleic acid encoding an anti-MET antibody heavy chain polypeptide or an anti-MET antibody fragment heavy chain polypeptide or fragment thereof and a nucleic acid encoding an anti-MET antibody light chain polypeptide or an anti-MET antibody fragment light chain polypeptide or fragment thereof. In some aspects, the anti-MET antibody heavy chain and the anti-MET antibody light chain are full-length heavy chain and light chain anti-MET antibody polypeptides. In other aspects, the anti-MET antibody heavy chain is an antibody Fab fragment heavy chain polypeptide, and the anti-MET antibody light chain is an antibody Fab fragment light chain polypeptide. In some embodiments, the anti-MET antibody heavy chain comprises the amino acid sequence of SEQ ID NO:51, the anti-MET antibody heavy chain fragment comprises the amino acid sequence of SEQ ID NO:52, and the anti-MET antibody light chain comprises the amino acid sequence of SEQ ID NO:50. In some embodiments, the mutant metA allele comprises a nucleic acid sequence selected from the group consisting of SEQ ID NO:23, SEQ ID NO:24, SEQ ID NO:25, and SEQ ID NO:26. In some embodiments, the mutant metK allele comprises a nucleic acid sequence selected from the group consisting of SEQ ID NO:27 and SEQ ID NO:28.

The invention further provides an anti-MET antibody or anti-MET antibody fragment produced by any of the methods described herein, wherein the anti-MET antibody or anti-MET antibody fragment is free of norleucine misincorporation.

In various aspects, a mutant microorganism comprising any one or more of the nucleic acid sequences provided by the present invention is bacteria; in other aspects, the microorganism is *E. coli*. The present invention specifically provides for the use of a mutant microorganism described herein for the production of heterologous (e.g., recombinant) polypeptides and heterologous (e.g., recombinant) proteins, wherein the misincorporation of norleucine into the heterologous polypeptides and heterologous proteins is reduced, substantially reduced, substantially eliminated, or prevented.

BRIEF DESCRIPTION OF THE DRAWINGS

FIG. 1 shows the nucleic acid sequence of metA(R27C) corresponding to SEQ ID NO:23.

FIG. 2 shows the nucleic acid sequence of metA(Y294C) corresponding to SEQ ID NO:24.

FIG. 3 shows the nucleic acid sequence of metA(I296S/P298L) corresponding to SEQ ID NO:25.

FIG. 4 shows the nucleic acid sequence of metA(Q64E) corresponding to SEQ ID NO:26.

FIG. 5 shows the nucleic acid sequence of metK(V185E) corresponding to SEQ ID NO:27.

FIG. 6 shows the nucleic acid sequence of metK (c1132del) corresponding to SEQ ID NO:28.

FIGS. 7A and 7B show the amino acid sequence and nucleic acid sequence of wild-type MetA corresponding to SEQ ID NO:29 and SEQ ID NO:31, respectively.

FIGS. 8A and 8B show the amino acid sequence and nucleic acid sequence of wild-type MetK corresponding to SEQ ID NO:30 and SEQ ID NO:32, respectively.

FIG. 12C shows growth trends for control host 60E4 with no feed (squares), for control host 60E4 with methionine feed (circles), and host 60E4 metA(Y294C) with no feed (triangles). Fermentations using all other mutants were performed with continuous water feed.

FIGS. 18A and 18B show the nucleic acid sequences of an anti-vascular endothelial growth factor (anti-VEGF) antibody Fab fragment light chain and heavy chain corresponding to SEQ ID NO:33 and SEQ ID NO:34, respectively.

FIGS. 21A and 21B show the amino acid sequences of an anti-vascular endothelial growth factor (anti-VEGF) antibody Fab fragment light chain and heavy chain corresponding to SEQ ID NO:46 and SEQ ID NO:47, respectively.

FIGS. 22A and 22B show the amino acid sequences of an anti-Factor D antibody Fab fragment light chain and heavy chain corresponding to SEQ ID NO:48 and SEQ ID NO:49, respectively.

FIGS. 23A, 23B, and 23C show the amino acid sequences of an anti-MET antibody light chain (SEQ ID NO:50), heavy chain (SEQ ID NO:51), and heavy chain fragment (SEQ ID NO:52).

DETAILED DESCRIPTION OF THE INVENTION

Figure 9:
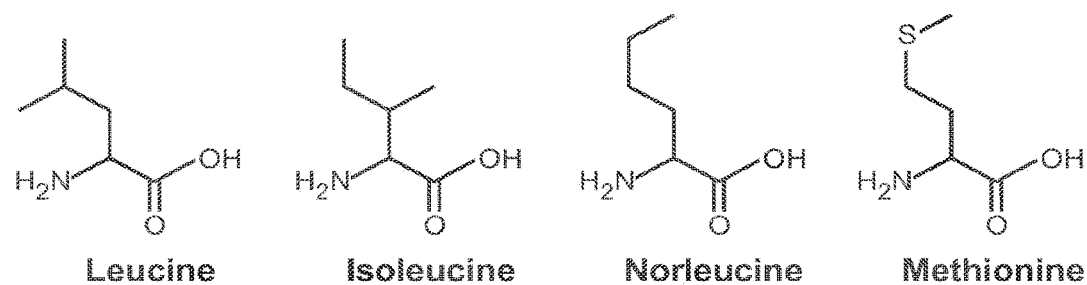
FIG. 9 shows the structure of norleucine and norleucine analogues. Norleucine is a structural analogue of methionine, where the sulfur (S) atom is replaced by a methylene group (i.e., —CH$_2$).
Figure 11:
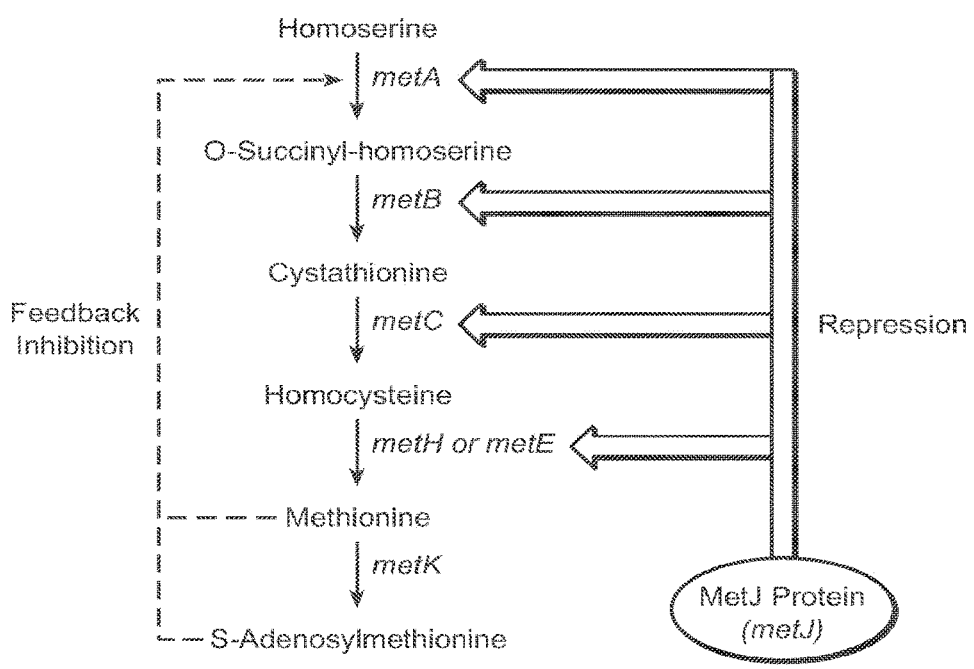
FIG. 11 shows methionine biosynthesis and regulation in *E. coli*. Dotted arrows indicate feedback inhibition and open arrows indicate repression. Methionine and S-adenosylmethionine (SAM) are feedback inhibitors of the enzyme MetA. The repressor MetJ and its co-repressor SAM inhibit the transcription of enzymes in the methionine regulon.
Figure 10:
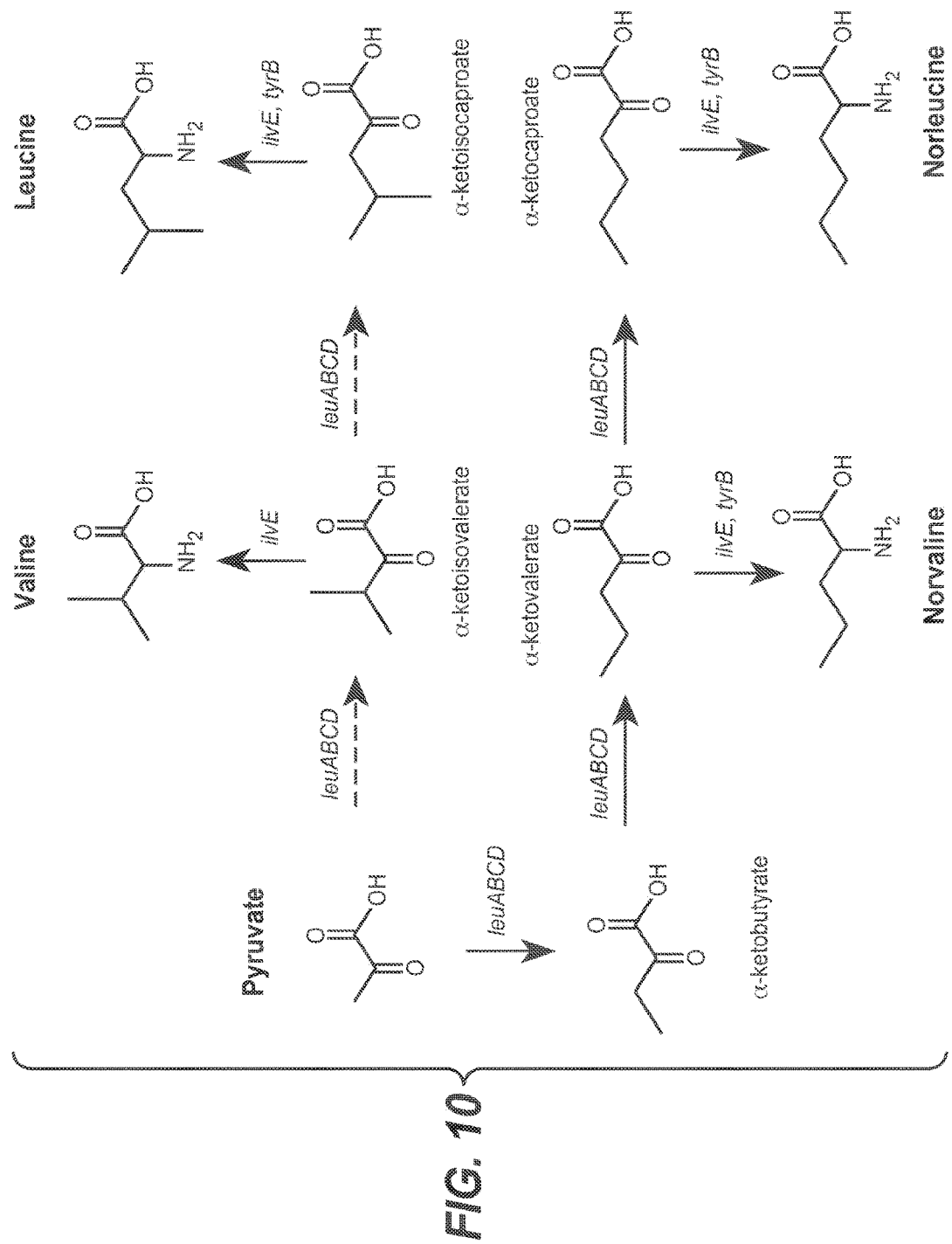
FIG. 10 shows a schematic of the norleucine biosynthetic pathway in *E. coli*. Dotted arrows indicate that multiple steps are involved. Pyruvate is converted to α-ketocaproate by three passes through the keto acid chain elongation process catalyzed by enzymes encoded by the leucine operon leuABCD. The intermediate α-ketocaproate is transaminated to norleucine by transaminases IlvE or TyrB.

The present invention provides, inter alia, methods and compositions for preventing misincorporation of norleucine into proteins and polypeptides, in particular during recombinant protein production in microorganisms. The present invention also provides microorganism host cells and nucleic acid molecules for use in the methods of the invention.

General Methods

The practice of the present invention will employ, unless otherwise indicated, conventional techniques of cell biology, cell culture, molecular biology (including recombinant techniques), microbiology, biochemistry, and immunology, which are known and available to one of skill in the art. Such techniques are described in the literature, such as, *Molecular Cloning: A laboratory Manual*, third edition (Sambrook et al., 2001) Cold Spring Harbor Press; *Oligonucleotide Synthesis* (P. Herdewijn, ed., 2004); *Animal Cell Culture* (R. I. Freshney, ed., 1987); *Methods in Enzymology* (Academic Press, Inc.); *Current Protocols in Molecular Biology* (F. M. Ausubel et al., eds., 1987); *PCR: The Polymerase Chain Reaction* (Mullis et al., eds., 1994); *Current Protocols in Immunology* (J. E. Coligan et al., eds., 1991); and *Short Protocols in Molecular Biology* (Wiley and Sons, 1999). Expression of antibody fragments and polypeptides in bacteria are described in, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.)

Unless defined otherwise, all technical and scientific terms used herein have the same meaning as is commonly understood by one of ordinary skill in the art to which the invention belongs.

Definitions

The terms "heterologous protein" or "heterologous polypeptide" refer to a protein or a polypeptide not naturally synthesized or produced by a cell or organism (e.g., a microorganism) of interest. For example, an *E. coli* cell may produce a human protein or a human polypeptide, and a human protein or a human polypeptide so produced is a heterologous protein or a heterologous polypeptide. Of particular interest in the context of the present invention are those heterologous proteins or heterologous polypeptides comprising methionine. A heterologous protein or a heterologous polypeptide as used herein also refers to a recombinant protein or a recombinant polypeptide.

The term "norleucine misincorporation" refers to the incorporation of a norleucine residue in a protein or polypeptide for which a methionine residue is encoded by the corresponding nucleic acid encoding the protein or polypeptide.

The terms "mutant allele" or "mutated allele" refer to an allele having a nucleic acid sequence which is different from or altered from the nucleic acid sequence of the wild-type allele (i.e., as naturally found within the cell or microorganism of interest).

The terms "mutant microorganism" or "mutated microorganism" refer to a microorganism which contains one or more mutant alleles or mutated alleles.

The phrase "substantially reduced" or "substantially different," as used herein, refers to a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., norleucine content in a protein or polypeptide).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extra-chromosomally or at a chromosomal location that is different from its natural chromosomal location.

"Isolated metA nucleic acid molecule" or "isolated metK nucleic acid molecule" refers to one or more nucleic acid molecules encoding MetA or MetK, respectively, including such nucleic acid molecule(s) in a single vector or separate vectors, and such nucleic acid molecule(s) present at one or more locations in a host cell. "Isolated metA nucleic acid molecule" or "isolated metK nucleic acid molecule" also refers to a mutant metA allele or a mutant met allele.

The phrase "protein or polypeptide free of norleucine misincorporation" refers to a protein or polypeptide which contains no detectable levels of norleucine residues.

As used herein, the singular form of "a", "an", and "the" includes the plural references unless indicated otherwise.

Reference to "about" a value or parameter herein refers to the usual error range for the respective value readily known to the skilled person in this technical field. Reference to "about" a value or parameter herein includes (and describes) aspects that are directed to that value or parameter, per se. For example, description referring to "about X" includes description of "X."

Methods for Preventing or Reducing Norleucine Misincorporation

The present invention relates, in part, to methods and compositions useful for preventing or reducing norleucine misincorporation into proteins and polypeptides, in particular during recombinant protein production in microorganisms.

Misincorporation of norleucine residues in place of methionine residues during recombinant protein production in *E. coli* has been previously described. One approach currently used to prevent or reduce norleucine misincorporation is by continuous or bolus feed of methionine to the culture medium during the fermentation process. Although this strategy is effective at reducing norleucine misincorporation, several operational disadvantages are associated with continuous or bolus feeding or addition of methionine during the fermentation process. For example, continuous or bolus feed to the culture increases the operational complexity and the overall cost of the fermentation process. In addition, methionine feed leads to undesirable dilution of the fermentation medium resulting in lower cell densities and possibly lower product yields.

To overcome these disadvantages, the present inventors have provided an alternative to continuous or bolus methionine feed in order to prevent or reduce norleucine misincorporation in heterologous protein or polypeptide production. In particular, the present invention provides microorganism (e.g., *E. coli*) host cells engineered to produce methionine to a degree or extent sufficient to prevent or reduce norleucine misincorporation during recombinant protein production, including recombinant protein production performed at high host cell densities. *E. coli* host cell mutants useful for large-scale methionine production were reported previously. (See, e.g., Chattopadhyay et al., (1991) J Gen Microbiol 137; 685-691; Nakamori et al., (1999) Appl Microbiol Biotechnol 52:179-185; Usuda and Kurahashi (2005) Appl Environ Microbiol 71:3228-3234; International Patent Application Publication No. WO2005/111202 2005; and United States Patent Application Publication No. US2009/0298135.) Many of these mutant *E. coli* strains contained mutations in three genes associated with the regulation of methionine biosynthesis: metJ, metA, and metK.

Transcriptional regulation of methionine biosynthesis in *E. coli* involves the enzyme MetJ (metJ gene product). MetJ is a transcriptional repressor which, when bound to its co-repressor S-adenosylmethionine (SAM), represses the transcription of genes in the methionine regulon, thus regulating the levels of methionine in the cell. (See, e.g., Marincs (2006) et al., Biochem J 396:227-234.) As previously reported, chemical mutagenesis of *E. coli* followed by selection for growth on ethionine (a toxic methionine analogue) led to the isolation of a serine to asparagine mutation at amino acid position 54 (S54N) in MetJ, which resulted in de-repression of methionine biosynthetic enzymes and increased methionine production. (See Nakamori et al., (1999) Appl Microbiol Biotechnol 52:179-185.) A complete disruption of the metJ gene also resulted in de-repression of enzymes involved in the methionine biosynthetic pathway and methionine overproduction. (See Usuda and Kurahashi (2005) Appl Environ Microbiol 71:3228-3234.)

Methionine biosynthesis in *E. coli* is also regulated by feedback inhibition (by methionine and SAM) of homoserine succinyltransferase (metA gene product), the enzyme involved in the first step of methionine biosynthesis. (See, e.g., Born and Blanchard (1999) Biochemistry 38:14416-14423.) Feedback resistant MetA (metA gene product) mutants in *E. coli* leading to deregulation of methionine biosynthesis were isolated previously by selecting for growth on the toxic methionine analogue α-methyl methionine. (See Usuda and Kurahashi (2005) Appl Environ Microbiol 71:3228-3234; and International Patent Application Publication No. WO2005/111202.)

The metK gene encodes for the enzyme S-adenosylmethionine synthase, which converts methionine to S-adenosylmethionine. (See Markham et al., (1980) J Biol Chem 255:9082-9092.) Partial loss-of-function MetK mutants resulting in low levels of SAM and hence de-repression of methionine biosynthetic enzymes (SAM is a co-repressor for MetJ) were previously isolated by selecting for growth on toxic methionine analogues, norleucine, and ethionine. (See Chattopadhyay et al., (1991) Gen Microbiol 137:685-691; Usuda and Kurahashi (2005) Appl Environ Microbiol 71:3228-3234; and International Patent Application Publication No. WO2005/111202.)

In the present invention, specific nucleic acid residues in the wild-type metA gene were mutated, resulting in the following amino acid substitutions in MetA (see FIG. 7A and SEQ ID NO:29 for wild-type MetA amino acid sequence): arginine to cysteine substitution at amino acid position 27 (R27C); glutamine to glutamic acid substitution at amino acid position 64 (Q64E); tyrosine to cysteine substitution at amino acid position 294 (Y294C); isoleucine to serine substitution at amino acid position 296 (I296S); and proline to leucine substitution at amino acid position 298 (P298L). *E. coli* host cells comprising one or more of these MetA amino acid substitutions produced methionine to a degree or extent sufficient to result in prevention of norleucine misincorporation in expressed heterologous proteins.

In some embodiments, the present invention provides various mutant metA alleles encoding the amino acid substitutions in MetA of R27C, Q64E, Y294C, I296S, and P298L (compared to the wild-type MetA amino acid sequence; FIG. 7 and SEQ ID NO:29). Such mutant metA alleles resulted in feedback resistant MetA enzyme. The mutant metA alleles were introduced into *E. coli* host cells (60E4) using an allele exchange method (see Materials and Methods below) to obtain mutant *E. coli* host cell strain 66H6 (60E4 metA(R27C)), 66H8 (60E4 metA(Y294C)), 6788 (60E4 metA(Q64E)), and 6789 (60E4 metA(I296S P298L)). The resulting mutant *E. coli* host cells obtained were evaluated for norleucine misincorporation during recombinant protein production performed without a continuous methionine feed. (See Example 4 below.)

All references to amino acid positions in MetA are made based on the homoserine succinyltransferase encoded by the metA gene of *E. coli* shown in FIGS. 7A and 7B, corresponding to SEQ ID NO:29 and SEQ ID NO:31. Reference to amino acid positions are made with the first amino acid methionine counting as amino acid position number 1. The relative positions of corresponding regions in homoserine succinyltransferase enzymes from other organisms can be identified by a person skilled in the art by, for example, simple sequence alignment.

In the present invention, a nucleic acid in the wild-type metK gene was mutated, resulting in the amino acid substitution in MetK of valine to glutamic acid at amino acid position 185 (V185E)). (See FIG. 8A and SEQ ID NO:30 for wild-type MetK amino acid sequence.) Additionally, a specific nucleic acid was deleted at cytosine base position 1132 in the metK gene (c1132del). *E. coli* host cells comprising one or more of these mutant metK alleles produced methionine to a degree or extent sufficient to result in prevention of norleucine misincorporation in expressed heterologous proteins.

In some embodiments, the present invention also provides various mutant metK alleles encoding the amino acid substitution V185E or a deletion of the cytosine base at position 1132 in the metK allele (c1132del). Such mutant metK alleles result in partial loss-of-function MetK enzymes. The mutant metK alleles were introduced into various *E. coli* host cells (66H8; 60E4 metA(Y294C), see above) using an allele exchange method (see Materials and Methods below) to obtain the *E. coli* host cell strains 67C2 (66H8 metK (V185E)) and 67C3 (66H8 metK(c1132del)), respectively. The resulting mutant *E. coli* host cells obtained were evaluated for norleucine misincorporation during recombinant protein production performed without a continuous methionine feed. (See Example 4 below.)

All references to amino acid positions in MetK are made based on the S-adenosylmethionine synthase encoded by the metK gene of *E. coli* shown in FIGS. 8A and 8B, corresponding to SEQ ID NO:30 and SEQ ID NO:32. Reference to amino acid positions are made with the first amino acid methionine counting as amino acid position number 1 The relative positions of corresponding regions in S-adenosylmethionine synthase enzymes from other organisms can be identified by a person skilled in the art by, for example, simple sequence alignment.

Nucleic Acid Molecules for metA and metK

By way of example, the present invention used isolated nucleic acid molecules comprising nucleic acid sequences of metA and metK that differ from nucleic acid sequences of wild-type metA and metK. The nucleic acid sequences of metA and metK provided by the present invention encode various amino acid substitutions to that encoded by wild-type metA (arginine at amino acid position 27 replaced with cysteine (R27C); glutamine at amino acid position 64 replaced with glutamic acid (Q64E); tyrosine at amino acid position 294 replaced with cysteine (Y294C); isoleucine at amino acid position 296 replaced with serine (I296S); proline at amino acid position 298 replaced with leucine (P298L); and isoleucine at amino acid position 296 replaced with serine (I296S) and proline at amino acid position 298 replaced with leucine (P298L)); and to that encoded by wild-type metK (valine at amino acid position 185 replaced with glutamic acid (V185E) and nucleic acid sequences comprising a deletion of the cytosine base at position 1132 (cdel1132del)). The use of any nucleic acid sequence encoding a metA allele or a metK allele which result in these amino acid substitutions is specifically contemplated herein for use in the methods of the present invention.

The present invention also provides isolated metA nucleic acid molecules encoding various altered MetA enzymes (i.e., encoding various mutant homoserine succinyltransferase enzymes). In some embodiments, the present invention provides an isolated nucleic acid molecule, wherein the nucleic acid molecule comprises a nucleic acid sequence selected from the group consisting of SEQ ID NO:23, SEQ ID NO:24, SEQ ID NO:25 and SEQ ID NO:26.

The present invention also provides isolated metK nucleic acid molecules encoding various altered MetK enzymes (i.e., encoding various mutant S-adenosylmethionine enzymes). In some embodiments, the present invention provides an isolated nucleic acid molecule, wherein the nucleic acid molecule comprises a nucleic acid sequence selected from the group consisting of SEQ ID NO:27 and SEQ ID NO:28.

The present invention also provides, by way of example, various combinations of mutant metA alleles and corresponding isolated nucleic acid molecules comprising nucleic acid sequences encoding the following amino acid substitutions in MetA: arginine at amino acid position 27 substituted with cysteine (R27C); glutamine at amino acid position 64 substituted with glutamic acid (Q64E); tyrosine at amino acid position 294 substituted with cysteine (Y294C); isoleucine at amino acid position 296 substituted with serine (I296S); proline at amino acid position 298 replaced with leucine (P298L); and isoleucine at amino acid position 296 substituted with serine (I296S) and proline at amino acid position 298 substituted with leucine (P298L). In some aspects, the mutant metA alleles provided by the present invention result in feedback-resistant (i.e., feedback-insensitive) MetA enzymes. Amino acid positions are in reference to wild-type MetA amino acid sequence as shown in FIG. 7A and SEQ ID NO:29.

Also provided by the present invention, by way of example, are various combinations of mutant metK alleles and corresponding isolated nucleic acid molecules comprising nucleic acid sequence encoding the following amino acid substitution in MetK: valine at amino acid position 185 substituted with glutamic acid (V185E). The present invention also provides nucleic acid sequences comprising a deletion of the cytosine base at position 1132 (c1132del) of the metK allele. In some aspects, the mutant metK alleles provided by the present invention result in partial loss-of-function MetK enzymes. Amino acid positions are in reference to wild-type MetK amino acid sequences as shown in FIG. 8A and SEQ ID NO:30.

Microorganisms for Use in the Present Methods

As described herein and by way of example, E. coli host cells were engineered for the bacteria to produce methionine to a degree or extent sufficient for the prevention or reduction of norleucine misincorporation during recombinant protein production, including recombinant protein production performed at high host cell densities. Accordingly, in some embodiments provided herein, the present invention provides mutant microorganism strains (i.e., mutant microorganism host cells) which produce methionine to a degree or extent sufficient to reduce or prevent norleucine misincorporation into proteins or polypeptides (e.g., to a degree or extent sufficient to reduce or prevent norleucine misincorporation into recombinant proteins or recombinant polypeptides, or to a degree or extent sufficient to reduce or prevent norleucine misincorporation into heterologous proteins or heterologous polypeptides).

Starting E. coli host cells suitable for use in the methods provided herein include, for example, (but are not limited to) E. coli W3110, E. coli 294, E. coli X1776, etc. These examples of E. coli host cells are illustrative rather than limiting. E. coli strain W3110 is a common host strain for recombinant DNA product fermentations. Mutant E. coli host cells of any of the above-mentioned E. coli host cell strains may also be employed as the starting host cells that are then further modified to contain the mutated metA and/or metK alleles described herein.

The present invention shows that use of E. coli host cells comprising various mutant alleles and combinations of mutant alleles for metA and metK in recombinant protein production was effective at preventing norleucine misincorporation into expressed recombinant proteins.
(See Example 4 below.)

The present invention provides a microorganism, wherein the microorganism produces methionine to a degree or extent sufficient to prevent or reduce norleucine misincorporation into proteins or polypeptides. In some aspects, the present invention provides a microorganism, wherein the microorganism is a feedback-insensitive homoserine succinyltransferase microorganism. In some embodiments, the present invention provides a microorganism comprising a mutant metA allele. In other embodiments, the present invention provides a microorganism comprising a mutant metA allele, wherein the mutant metA allele encodes a R27C amino acid substitution in MetA, a Q64E amino acid substitution in MetA, a Y294C amino acid substitution in MetA, an I296S amino acid substitution in MetA, or a P298L amino acid substitution in MetA. In some embodiments, the present invention provides a microorganism comprising a mutant metA allele encoding more than one amino acid substitution described above, including, for example, a mutant metA allele encoding a I296S amino acid substitution and a P298L amino acid substitution in MetA. In various aspects, the microorganism comprising any one or more of the nucleic acid sequences provided by the present invention is bacteria; in other aspects, the microorganism is E. coli. The present invention specifically provides for the use of microorganisms described herein for production of heterologous (e.g., recombinant) polypeptides and heterologous (e.g., recombinant) proteins, wherein misincorporation of norleucine into the heterologous polypeptides and heterologous proteins is reduced or prevented.

As described above, the present invention provides microorganisms comprising one or more mutant metA alleles. In some embodiments, the mutant metA alleles encoding a R27C amino acid substitution in MetA, encoding a Q64E amino acid substitution in MetA, encoding a Y294C amino acid substitution In MetA, or encoding a I296S amino acid substitution and a P298L amino acid substitution in MetA, are encoded by a nucleic acid sequence comprising SEQ ID NO:23 (R27C), SEQ ID NO:26 (Q64E), SEQ ID NO:24 (Y294C), or SEQ ID NO:25 (I296S and P298L), respectively. In other embodiments, the microorganisms provided by the present invention comprise mutant metA alleles encoded by a nucleic acid sequence comprising SEQ ID NO:23 (R27C), SEQ ID NO:26 (Q64E), SEQ ID NO:24 (Y294C), or SEQ ID NO:25 (I296S and P298L). In various aspects, a microorganism comprising any one or more of the nucleic acid sequences provided by the present invention is bacteria; in other aspects, the microorganism is E. coli. The present invention specifically provides for the use of microorganisms described herein for the production of heterologous (e.g., recombinant) polypeptides and heterologous (e.g., recombinant) proteins, wherein the misincorporation of norleucine into the heterologous polypeptides and heterologous proteins is reduced or prevented.

As stated above, the present invention provides methods for preventing or reducing norleucine incorporation into proteins and polypeptides expressed by a microorganism, wherein the microorganism is a microorganism which produces methionine to a degree or extent sufficient to prevent or reduce norleucine misincorporation into proteins or polypeptides. In some aspects, the present invention provides a microorganism, wherein the microorganism is a microorganism de-repressed for methionine production. In some embodiments, the present invention provides a microorganism comprising a mutant metK allele. In other embodiments, the present invention provides a microorganism comprising a mutant metK allele, wherein the mutant metK allele encodes a V185E amino acid substitution in MetK. In some embodiments, the present invention provides a microorganism comprising a mutant metK allele, wherein the mutant metK allele comprises a deletion of the nucleic acid cytosine at nucleic acid residue 1132 of the metK allele. In various aspects, a microorganism comprising any one or more of the nucleic acid sequences provided by the present invention is bacteria; in other aspects, the microorganism is E. coli. The present invention specifically provides for the use of the microorganisms described herein for the production of heterologous (e.g., recombinant) polypeptides and heterologous (e.g., recombinant) proteins, wherein the misincorporation of norleucine into the heterologous polypeptides and heterologous proteins is reduced or prevented.

As described above, the present invention provides microorganisms comprising one or more mutant metK alleles. In some embodiments, the mutant metK alleles encoding a V185E amino acid substitution in MetK or comprising a deletion of the nucleic acid cytosine at nucleic acid residue 1132 of the metK allele, are encoded by a nucleic acid sequence comprising SEQ ID NO:27 (V185E) or a nucleic acid sequence comprising SEQ ID NO:28 (c1132del), respectively. In other embodiments, the microorganisms provided by the present invention comprise mutant metK alleles encoded by a nucleic acid sequence comprising SEQ ID NO:27 (V185E) or SEQ ID NO:28 (c1132del). In various aspects, the microorganism comprising any one or more of the nucleic acid sequences provided by the present invention is bacteria; in other aspects, the microorganism is E. coli. The present invention specifically provides for the use of any microorganisms described herein for the production of heterologous (e.g., recombinant) polypeptides and heterologous (e.g., recombinant) proteins, wherein misincorporation of norleucine into the heterologous polypeptides and heterologous proteins is reduced or prevented.

The use of any nucleic acid sequence encoding metA or metK alleles which result in the amino acid substitutions described herein are specifically contemplated herein for use in the methods of the present invention.

In other embodiments, the present invention provides a microorganism comprising a mutant metA allele and a mutant metK allele. In some embodiments, a microorganism provided by the present invention is a microorganism comprising a mutant metA allele and a mutant metK allele, wherein the mutant metA allele encodes a Y294C amino acid substitution in MetA and the mutant metK allele encodes a V185E amino acid substitution in MetK. In some embodiments provided by the present invention, the microorganism is a microorganism comprising a mutant metA allele and a mutant metK allele, wherein the mutant metA allele encodes a Y294C amino acid substitution in MetA and the mutant metK allele comprises a deletion of the nucleic acid cytosine at nucleic acid residue 1132 of the metK allele. In various aspects, a microorganism comprising any one or more of the nucleic acid sequences provided by the present invention is bacteria; in other aspects, the microorganism is E. coli. The present invention specifically provides for the use of any microorganisms described herein for the production of heterologous (e.g., recombinant) polypeptides and heterologous (e.g., recombinant) proteins, wherein misincorporation of norleucine into the heterologous polypeptides and heterologous proteins is reduced or prevented.

Production of Microorganism Strains

The present invention provides methods for producing a microorganism (e.g., E. coli host cells), wherein the microorganism produces methionine to a degree or extent sufficient to reduce or prevent norleucine misincorporation into polypeptides and proteins. By way of example, E. coli host cells comprising mutant metA alleles and/or mutant metK alleles were generated using allele exchange methods as known in the art and as previously described. (See Metcalf et al., (1994) Gene 138:1-7; and Bass et al., (1996) J Bacteriol 178: 1154-61; see Materials and Methods section of the instant specification.) The present invention is not limited to the means by which E. coli host cells comprising mutant metA alleles and mutant metK alleles are produced. Various methods for introducing mutant alleles or otherwise producing microorganism strains (e.g., bacteria, E. coli) comprising mutant alleles are well-known to one skilled in the art.

Prevention or Reduction of Norleucine Misincorporation

Methods and compositions of the present invention can be applied to the production of heterologous or recombinant proteins or polypeptides, and can be used with both large and small scale protein or polypeptide production. Methods and compositions of the present invention are particularly useful for high density fermentation of microorganisms, such as, for example, E. coli host cells, for the production of recombinant proteins and polypeptides. The methods and compositions provided by the present invention are useful for recombinant production of proteins and polypeptides, in particular for recombinant production of proteins and polypeptides in which norleucine misincorporation is undesirable, such as, for example, in recombinant proteins and polypeptides for use in various research and therapeutic applications.

In some embodiments, the present invention provides methods for preventing or reducing norleucine misincorporation in a protein or polypeptide, the method comprising expressing the protein or polypeptide in a microorganism, wherein the microorganism is a feedback-resistant or feedback-insensitive homoserine succinyltransferase microorganism. In other embodiments, the present invention provides methods for reducing or preventing norleucine misincorporation in a protein or polypeptide, the method comprising expressing the protein or polypeptide in a microorganism, wherein the microorganism is a microorganism de-repressed for methionine production. In some embodiments, the feedback-resistant or feedback-insensitive homoserine succinyltransferase microorganism is a microorganism which comprises a mutant metA allele. In some embodiments, the microorganism de-repressed for methionine production is a microorganism which comprises a mutant metK allele. In other embodiments, the microorganism for use in preventing or reducing norleucine misincorporation comprises a mutant metA allele and a mutant metK allele.

In some embodiments, the present invention provides methods for reducing or preventing norleucine misincorporation in a protein or polypeptide, the method comprising expressing the protein or polypeptide in a microorganism, wherein the microorganism comprises a mutant metA allele, wherein the mutant metA allele comprises a nucleic acid sequence selected from the group consisting of SEQ ID NO:23, SEQ ID NO:24, SEQ ID NO:26, and SEQ ID NO:26. In other embodiments, the present invention provides methods for reducing or preventing norleucine misincorporation in a protein or polypeptide, the method comprising expressing the protein or polypeptide in a microorganism, wherein the microorganism comprises a mutant metA allele, wherein the mutant metA allele comprises a nucleic acid sequence encoding MetA, wherein the nucleic acid sequence encodes an amino acid substitution in MetA selected from the group consisting of R27C, Q64E, Y294C, I296S, and P298L. In other embodiments, the nucleic acid sequence encodes amino acid substitutions in MetA consisting of both I296S and P298L. Amino acid positions are in reference to wild-type MetA amino acid sequence as shown in FIG. 7A and SEQ ID NO:29.

In some embodiments, the present invention provides methods for reducing or preventing norleucine misincorporation in a protein or polypeptide, the method comprising expressing the protein or polypeptide in a microorganism, wherein the microorganism comprises a mutant metK allele, wherein the mutant metK allele comprises a nucleic acid sequence selected from the group consisting of SEQ ID NO:27 and SEQ ID NO:28. In some embodiments, the present invention provides methods for reducing or preventing norleucine misincorporation in a protein or polypeptide, the method comprising expressing the protein or polypeptide in a microorganism, wherein the microorganism comprises a mutant metK allele, wherein the mutant metK allele comprises a nucleic acid sequence encoding MetK, wherein the nucleic acid sequence encodes the amino acid substitution V185E in MetK. In other embodiments, the nucleic acid sequence comprises a deletion of the cytosine base at nucleic acid residue position 1132 in metK allele. Amino acid positions are in reference to wild-type MetK amino acid sequence as shown in FIG. 8A and SEQ ID NO:30.

In some embodiments, the present invention provides methods for reducing or preventing norleucine misincorporation in a protein or polypeptide, the method comprising expressing the protein or polypeptide in a microorganism, wherein the microorganism comprises a mutant metA allele and a mutant metK allele, and further wherein the mutant metA allele comprises the nucleic acid sequence of SEQ ID NO:24, and the mutant metK allele comprises the nucleic acid sequence of SEQ ID NO:27. In some embodiments, the present invention provides methods for reducing or preventing norleucine misincorporation in a protein or polypeptide, the method comprising expressing the protein or polypeptide in a microorganism, wherein the microorganism comprises a mutant metA allele and a mutant metK allele, wherein the mutant metA allele comprises the nucleic acid sequence of SEQ ID NO:24, and the mutant metK allele comprises the nucleic acid sequence of SEQ ID NO:28.

In some embodiments, the present invention provides methods for reducing or preventing norleucine misincorporation in a protein or polypeptide, the method comprising expressing the protein or polypeptide in a microorganism, wherein the microorganism comprises a mutant metA allele and a metK allele, wherein the mutant metA allele comprises a nucleic acid sequence encoding the amino acid substitution Y294C in MetA, and the mutant metK allele comprises a nucleic acid sequence encoding the amino acid substitution V185E in MetK. In some embodiments, the present invention provides methods for reducing or preventing norleucine misincorporation in a protein or polypeptide, the method comprising expressing the protein or polypeptide in a microorganism, wherein the microorganism comprises a mutant metA allele and a metK allele, wherein the mutant metA allele comprises a nucleic acid sequence encoding the amino acid substitution Y294C in MetA, and the mutant metK allele comprises a nucleic acid sequence comprising a deletion of the cytosine base at nucleic acid residue position 1132 in metK allele. Amino acid positions are in reference to wild-type MetA amino acid sequence as shown in FIG. 7A and SEQ ID NO:29 and in reference to wild-type MetK amino acid sequence as shown in FIG. 8A and SEQ ID NO:30.

In some aspects of the methods for reducing or preventing norleucine misincorporation into a protein or polypeptide by a microorganism provided herein, the microorganism is a bacteria, in particular an *E. coli*. In other aspects, the protein or polypeptide is a heterologous protein or a heterologous polypeptide, or a recombinant protein or a recombinant polypeptide. For example, the microorganism can comprise a nucleic acid encoding a protein or polypeptide heterologous to the microorganism; e.g., the microorganism is transformed with a nucleic acid encoding a protein or polypeptide heterologous to the microorganism, which can be, for example, DNA (e.g., cDNA or genomic DNA), as by use of a recombinant expression vector. In other aspects, the method further comprises culturing the microorganism under conditions suitable for expression of the protein or polypeptide. In some embodiments, the microorganism is grown in a culture medium, wherein the culture medium contains a low concentration of methionine. The protein or polypeptide can then be recovered, purified, etc; the recovery may be from, for example, the periplasm or culture medium of the microorganism. In some aspects, the culturing takes place in a fermentor, such as, for example, culturing under conditions of high cell-density fermentation.

A heterologous nucleic acid encoding a heterologous protein or polypeptide is suitably inserted into a replicable vector for expression in the microorganism under the control of a suitable promoter. Many vectors are available for this purpose, and selection of the appropriate vector will depend on, for example, the size of the nucleic acid to be inserted into the vector or the particular microorganism host cell to be transformed with the vector. Suitable vectors are well-known to one of ordinary skill in the art.

The methods and compositions provided by the present invention are particularly useful for production of recombinant proteins and polypeptides in which norleucine misincorporation is undesirable, such as, for example, in recombinant proteins and polypeptides for use in various therapeutic, medical, research, and diagnostic applications. For example, the methods and compositions of the present invention are applicable for recombinant production of therapeutic antibodies, such as, for example, polyclonal and monoclonal antibodies for medical and pharmaceutical use. Examples of polyclonal and monoclonal antibodies for medical and pharmaceutical use include, but are not limited to, anti-VEGF antibodies, anti-factor D antibodies, anti-hepatocyte growth factor receptor antibodies (e.g., anti-MET antibodies), etc.

The methods and compositions of the present invention are also useful for the production of antibody fragments. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments. Production of recombinant antibodies as provided by the present methods, compositions, and microorganisms, can be performed by expression of a nucleic acid encoding an antibody heavy chain polypeptide and expression of a nucleic acid encoding an antibody light chain polypeptide within a microorganism as described above (e.g., bacterial host cell, *E. coli*). In some aspects, the antibody heavy chain and the antibody light chain are full-length heavy chain and light chain antibody polypeptides. In other aspects, the antibody heavy chain is an antibody Fab fragment heavy chain, and the antibody light chain is an antibody Fab fragment light chain.

The methods and compositions of the present invention are also useful for the production of multi-specific antibodies, e.g., bispecific antibodies. Multi-specific antibodies are antibodies that have binding specificities for at least two different epitopes. Exemplary multi-specific antibodies may bind to two different epitopes of the protein, or may bind two different epitopes of two different proteins. Bispecific antibodies can be prepared as full-length antibodies or antibody fragments (e.g., F(ab')$_2$ bispecific antibodies). Techniques for making multi-specific antibodies include, but are not limited to, recombinant co-expression of two immunoglobulin heavy chain-light chain pairs having different specificities (see Milstein and Cuello, *Nature* 305: 537 (1983); International Application Publication No. WO 93/08829; Traunecker et al., *EMBO J.* 10: 3655 (1991)); and "knob-in-hole" engineering (see, e.g., U.S. Pat. No. 5,731,168).

Additionally, the methods and compositions of the present invention are useful for the production of other biomolecules for therapeutic and research applications, such as, for example, human growth hormone (somatropin), insulin, etc.

EXAMPLES

The following are examples of methods and compositions of the invention. It is understood that various other embodiments may be practiced, given the general description provided above.

Materials and Methods

Bacterial Strains, Plasmids and Growth Conditions

Bacterial strains used in the Examples described herein are derivatives of the *E. coli* strain W3110. (See Bachmann (1972) Bacteriol Rev 36:525-557.) Antibiotic selection was maintained for all markers at the following concentrations: carbenicillin (plasmid or chromosomal), 50 µg/ml; kanamycin (chromosomal), 30 µg/ml; tetracycline (plasmid or chromosomal), 10 µg/ml.

Strain and Plasmid Construction

Oligonucleotides used in the construction of plasmids and bacterial strains (i.e., *E. coli*) are listed in Table 1 below. Standard techniques were used for cloning, DNA analysis, PCR amplification, transformation, electroporation, and P1 transduction. Chromosomal alleles were moved by P1 transduction. The metJ::Kan$^R$ allele was derived from the bacterial strain JW3909-1, which was obtained from The *Coli* Genetic Stock Center (CGSC, Yale University). All allele replacements were confirmed by PCR analysis.

TABLE 1

| Primer name | Sequence (5'-3')$^a$ | |
|---|---|---|
| SacI-metAflank-F | CACACGAGCTCCTCATTTTGCTCATTAACGTTGG | SEQ ID NO: 1 |
| SalI-metAflank-R | CACACGTCGACGCGAATGGAAGCTG | SEQ ID NO: 2 |
| SacI-metKflank-F | CACACGAGCTCGTATGCAAAGCAGAGATGC | SEQ ID NO: 3 |
| SalI-metKflank-R | CACACGTCGACCGTCATTGCCTTGTTTG | SEQ ID NO: 4 |
| metAflankmid-F | GTTCTGATCCTTAACCTGATGCCGAAGAAG | SEQ ID NO: 5 |
| metAflankmid-R | CCAGCGTTTGCGCATCATATTCGG | SEQ ID NO: 6 |
| metKflankmid-F | GGCAAAACACCTTTTTACGTCCGAGTCC | SEQ ID NO: 7 |
| metKflankmid-R | GAACTCACGTACCAGCAGGGTCAGTTG | SEQ ID NO: 8 |
| pS1080-P | CCAGTCACGACGTTGTAAAACGACGG | SEQ ID NO: 9 |
| pS1080-T | AGTGAACGGCAGGTATATGTGATGG | SEQ ID NO: 10 |
| QC-metAR27C-F | GTGATGACAACTTCTtGTGCGTCTGGTCAGG | SEQ ID NO: 11 |
| QC-metAR27C-R | CCTGACCAGACGCACaAGAAGTTGTCATCAC | SEQ ID NO: 12 |
| QC-metAQ64E-F | CAAACTCACCTTTGgAGGTCGATATTCAGC | SEQ ID NO: 13 |
| QC-metAQ64E-R | GCTGAATATCGACCTcCAAAGGTGAGTTTG | SEQ ID NO: 14 |
| QC-metAY294C-F | GCTCAACTATTACGTCTgCCAGATCACGCCATACG | SEQ ID NO: 15 |
| QC-metAY294C-R | CGTATGGCGTGATCTGGcAGACGTAATAGTTGAGC | SEQ ID NO: 16 |
| QC-metAI296SP298L-F | CGTCTACCAGAgCACGCtATACGATCTACG | SEQ ID NO: 17 |
| QC-metAI296SP298L-R | CGTAGATCGTATaGCGTGcTCTGGTAGACG | SEQ ID NO: 18 |
| QC-metKV185E-F | ATCGATGCTGTCGaGCTTTCCACTCAG | SEQ ID NO: 19 |
| QC-metKV185E-R | CTGAGTGGAAAGCtCGACAGCATCGAT | SEQ ID NO: 20 |

TABLE 1-continued

| Primer name | Sequence (5'-3')[a] | |
|---|---|---|
| QC-metKc1132del-F | GCGCAGCTGCTGGCGATGCTGCCG | SEQ ID NO: 21 |
| QC-metKc1132del-R | CGGCAGCATCGCCAGCAGCTGCGC | SEQ ID NO: 22 |

[a]Underlined nucleic acid residues introduce amino acid mutations. Lowercase nucleic acid residues indicate residues different from the wild-type nucleic acid sequence.

The metA gene was PCR amplified from bacterial strain W3110 (Bachmann (1972) Bacterial Rev 36:525-557) using primers SacI-metAflank-F and SalI-metAflank-R, digested with SacI and SalI, and ligated into SacI and SalI digested plasmid pS1080 to obtain plasmid pS1080-metAflank. Plasmids pS1080-metAflank(R27C), pS1080-metAflank(Q64E), pS1080-metAflank(Y294C), and pS1080-metAflank(I296SP298L) were constructed by mutagenizing plasmid pS1080-metAflank using a QuikChange kit (Stratagene) and the following sets of primers: (QC-metAR27C-F;QC-metAR27C-R), (QC-metAQ64E-F;QC-metAQ64E-R), (QC-metAY294C-F;QC-metA Y294C-R) and (QC-metAI296SP298L-F;QC-metAI296SP298L-R), respectively.

The metK gene was PCR amplified from bacterial strain W3110 using primers SacI-metKflank-F and SalI-metKflank-R, digested with SacI and SalI, and ligated into SacI and SalI digested plasmid pS1080 to obtain plasmid pS1080-metKflank. Plasmids pS1080-metKflank(V185E) and pS1080-metKflank(c1132del) were constructed by mutagenizing plasmid pS1080-metKflank using a QuikChange kit (Stratagene) and the following set of primers: (QC-metKV185E-F;QC-metKV185E-R), and (QC-metKc1132del-F;QC-metKc1132del-R), respectively.

Allele exchange was carried out using the methods previously described. (See Metcalf et al., (1994) Gene 138:1-7; and Bass et al., (1996) J Bacteriol 178: 1154-61.)

As stated above, allele exchange was conducted using the protocol described by Metcalf et al. (supra) as modified by Bass et al (supra). Cointegrates were transferred into 60E4 host cell background or 66H8 host cell background. Following sucrose counter-selection, sucrose-resistant colonies were screened for carbenicillin sensitivity by replica streaking on LB agar and LB agar plates containing carbenicillin. Carbenicillin-sensitive colonies were subsequently isolated and allele exchange was confirmed by PCR amplification of the entire metA or metK reading frame followed by DNA sequencing. The suicide plasmid vector pS1080 contains the conditional R6Kγ origin and carbenicillin resistance selectable marker, as well as a counter-selectable sacB gene, which confers sucrose sensitivity.

Bacteria strains and plasmids used in the experiments described herein are listed in Table 2 below.

TABLE 2

| Strain or | Genotype or description | Ref. or |
|---|---|---|
| W3110 | F⁻ lambda⁻ IN(rrnD-rrnE)1 rph-1 | Laboratory |
| JW3909-1 | (ΔaraD-araB)567 ΔlacZ4787(::rrnB-3) λ⁻rph-1 | CGSC |
| 60E4 | W3110 ΔfhuA (ΔtonA) Δptr ΔompT ΔdegP ΔphoA | Laboratory |
| 66G6 | 60E4 ΔmetJ725::kan^R | This study |
| 66H6 | 60E4 metA(R27C) | This study |
| 66H8 | 60E4 metA(Y294C) | This study |
| 67B8 | 60E4 metA(I296SP298L) | This study |
| 67B9 | 60E4 metA(Q64E) | This study |
| 67C2 | 60E4 metA(Y294C) metK(V185E) | This study |
| 67C3 | 60E4 metA(Y294C) metK(c1132del) | This study |
| 66F8 | W3110 ΔfhuA (ΔtonA) ΔphoA ilvG2096 (IlvG⁺; Valʳ) | Laboratory |
| 67C5 | 66F8 metA(Y294C) | This study |
| 64B4 | W3110 ΔfhuA (ΔtonA) ΔphoA ilvG2096 (IlvG⁺; Valʳ) | Laboratory |
| 67C4 | 64B4 metA(Y294C) | This study |
| pS1080 | Counter-selectable allele-exchange suicide vector, | Laboratory |
| pS1080-metA | MetA in pS1080 | This study |
| pS1080-metK | MetK in pS1080 | This study |
| pS1080- | MetA with R27C mutation cloned in pS1080 | This study |
| pS1080- | MetA with Q64E mutation cloned in pS1080 | This study |
| pS1080- | MetA with Y294C mutation cloned in pS1080 | This study |
| pS1080-metA(I296SP29 | MetA with I296S and P298L mutation cloned in pS1080 | This study |
| pS1080- | MetK with V185E mutation cloned in pS1080 | This study |
| pS1080- | MetK with cytosine deletion at position 1132 cloned | This study |

Fermentation

The E. coli host strain 60E4 was transformed with a pBR322-based expression plasmid containing polynucleic acid encoding a light chain and a heavy chain of an anti-VEGF antibody antigen binding (Fab) fragment (SEQ ID NO:33 and SEQ ID NO:34, respectively). (See anti-VEGF antibody Y0317 in International Application Publication No. WO1998/45331; International Application Publication No. WO2002/40697 (Example 2, describing fermentation of anti-VEGF antibody Y0317); and Chen et al., (1999) J Mol Biol 293:865-881, anti-VEGF antibody Y0317, each of which is incorporated herein in its entirety by reference.)

The E. coli host strain 66F8 was transformed with an expression plasmid containing polynucleic acid encoding a light chain and a heavy chain of an anti-Factor D antibody antigen binding (Fab) fragment, corresponding to the amino acid sequence of SEQ ID NO:48 and SEQ ID) NO:49, respectively. (See anti-Factor D antibody number 238-1 in International Application Publication No. WO2009/134711 and anti-Factor D antibody number 111 in International Application Publication No. WO2008/055206, each of which is incorporated herein in its entirety by reference.)

The *E. coli* host strain 64B4 was transformed with an expression plasmid containing polynucleic acid encoding a light chain, a heavy chain, and a heavy chain fragment of an anti-MET antibody corresponding to the amino acid sequence of SEQ ID NO:50, SEQ ID NO:51, and SEQ ID NO:52, respectively).

Expression of the recombinant heavy chain and light chain Fab fragment polypeptides was controlled by the phoA promoter with induction occurring upon the depletion of inorganic phosphate in the medium. (See Laird et al., (2005) Protein Expr Purif 39:237-246.) The heavy chain and light chain Fab fragment polypeptides were directed for exportation to the *E. coli* periplasm by a STII-signal sequence, where the product was assembled. High cell density fermentations at the 10 L working volume (W V) were carried out as described previously. (See Simmons et al., (2002) J Immunol Methods 263:133-147.) At a cell density of approximately 200 $OD_{550}$, a continuous 3% methionine or water feed was initiated and fed through the remainder of the fermentation process.

Three different fermentation processes were examined using host cell 60E4 (fermentation process AF1), host cell 66F8 (fermentation process AF2), and host cell 64134 (fermentation process AF3). (See Example 5 and Table 4 below.)

Purification

After fermentations were completed, whole cell broth was cooled to <15° C. in the fermenter and the cooled broth was processed for protein purification. One volume of the cooled broth was mixed with 0.06 volumes of $MgSO_4$ (60 mM final concentration) and titrated to pH 3.8 with citric acid (1 M). Cells were then disrupted using a microfluidizer at approximately 12,000 psi (Microfluidics, Redwood Shores, Calif.) and the disrupted cells were incubated at 35° C. for 3 hours with continuous shaking. The homogenate was diluted 3-fold with cold purified water and the diluted homogenate was centrifuged at 6,000×g using a fixed angle rotor at 4° C. for 20 minutes. The supernatant was filtered using 0.22 μm filters and titrated to pH 7.5 with 1.5 M Tris base.

The recombinant Fab protein was purified using Protein G affinity chromatography as follows. Poly-prep chromatography columns (Bio Rad) were packed with Protein G Sepharose 4 Fast Flow resin (GE Healthcare) and equilibrated with at least 5 column volumes of PBS, pH 7.2. Filtered supernatant was loaded into the Protein G packed column, washed twice with PBS, and eluted with 50 mM citric acid. The final Fab protein pool was titrated to pH 7 with 1.5 M Tris base and analyzed for norleucine content as described below. This corresponds to purification for fermentation process AF1.

Three different recombinant protein product purification processes were used, each specific to fermentation process AF1 (for host cell 60E4), AF2 (for host cell 66F8), or AF3 (for host cell 64B4). (See Example 7 and Table 6 below.)

Amino Acid Analysis

To determine intracellular methionine levels, whole cell broth samples containing $87.6 \times 10^9$ cells were pelleted at 17,000×g for 5 minutes at 4° C., washed once in PBS, and then resuspended in extraction buffer (10 mM Tris, 5 mM EDTA, 5 mM iodoacetamide (IAM), 0.2 mg/ml lysozyme, pH 6.8). Cells were then lysed by two cycles of sonication, and then centrifuged for 20 min at 13,500 rpm to remove cell debris. The supernatants were transferred to 0.2 μm microcentrifuge tube filters (Bio Rad) and centrifuged at 17,000×g for 5 minutes at 4° C. The filtrates were diluted and the amino acids were analyzed as previously described (Feeney et al., (2013) Biotechnology and Bioengineering, 110:1087-1097). For determining extracellular methionine levels, supernatant samples prepared from whole cell broth collected during fermentation after centrifugation for 3 min at 14,000×rpm were diluted and the amino acids analyzed as described below. (See Feeney et al., (2013) Biotechnology and Bioengineering, 110:1087-1097.)

Amino acid concentrations were analyzed using a reversed-phase HPLC method. Samples containing amino acids were treated with 6-aminoquinolyl-N-hydroxysuccinimidyl carbamate to produce highly fluorescent derivatives. (See Cohen and Michaud (1993) Anal Biochem 211:279-287.) HPLC assays used detected the following amino acids with a detection limit of 0.01 mM: histidine, asparagine, serine, glutamine, arginine, glycine, aspartate, glutamate, threonine, alanine, proline, ornithine, cysteine, lysine, tyrosine, methionine, valine, isoleucine, leucine, phenylalanine and tryptophan.

Phosphate Levels

Phosphate levels were measured using COBAS Integra 400 (Roche Diagnostics) according to methods previously published. (See Taussky and Shorr (1953) J Biol Chem 202:675-685.)

Titer Measurements

Whole cell broth samples were diluted 6-fold with extraction buffer (10 mM Tris, 5 mM EDTA, 5 mM IAM, 0.2 mg/ml lysozyme, pH 6.8) and incubated for 10 minutes on ice. After two rounds of sonication, the samples were centrifuged at 17,000×g for 20 minutes at 4° C. Product titer was determined from supernatants using HPLC.

Integrated $OD_{550}$ Measurements

Integrated $OD_{550}$ was determined by using trapezoidal integration using the following formula:

$$iOD_{550} = \sum_{i=j}^{i=k} (t_i - t_{i-1}) \frac{(OD_{550,i} + OD_{550,i-1})}{2}$$

where, j=index of the first measurement performed at or after 24 hours of culture time; k=total number of $OD_{550}$ measurements performed, $t_i$=elapsed culture time in hours at measurement i; $OD_{550,i}$=$OD_{550}$ at measurement i.

Norleucine Analysis

For analysis of norleucine content, purified recombinant protein samples were subjected to trypsin digestion based on a method previously described (See Yu et al., (2009) Anal Chem 81:9282-9290.) Peptide map analysis was performed using a reversed-phase HPLC and online liquid chromatography tandem mass spectrometry (LC/MS) as previously described. (See Yu et al., (2009) Anal Chem 81:9282-9290; and Yu et al., (2011) Anal Chem 83:5912-5919.) High resolution mass determination was performed with an LTQ-Orbitrap XL instrument (Thermo Scientific, San Jose, US) using a full-MS survey scan with resolution set at 60,000 at m/z 400, followed by ion trap MS2 scans for ions of interest. For determination of the relative level of norleucine within the polypeptides, extracted ion chromatograms were generated for both methionine-containing and norleucine-containing peptides using the most abundant charge state with an extraction window of monoisotopic m/z±10 ppm. Relative amount of norleucine-containing species relative to that of methionine-containing species were calculated using the respective integrated peak areas.

Western Blots

Whole cell broth samples obtained during the fermentation were diluted 6-fold with extraction buffer (10 mM Tris, 5 mM EDTA, 5 mM IAM, 0.2 mg/ml lysozyme, pH 6.8) and incubated for 10 minutes on ice. After two rounds of sonication, samples were centrifuged at 17,000×g for 25 minutes at 4° C. Samples were loaded on 4-12% Tris-Glycine gels under non-reducing conditions. Protein was transferred to nitrocellulose membranes using an iBlot Blotting System (Invitrogen). Membranes were blocked with 0.5% Gelatin in NET buffer (150 mM NaCl, 5 mM EDTA, 50 mM Tris, 0.05% TritonX-100) for 30 minutes, followed by incubation in a 1:300,000 dilution of peroxidase conjugated goat IgG fraction to human IgG Fab (MP Biomedical) in the blocking buffer. After washing 3 times with NET buffer, the blots were visualized on X-ray film using Western Lightning ECL Substrate (PerkinElmer) after a 5 second exposure.

Example 1. Norleucine Misincorporation During *E. coli* Fermentation

As described above, norleucine misincorporation often occurs during recombinant protein production in *E. coli*. The extent of norleucine misincorporation during recombinant protein production depends on several factors, such as, for example, the nature of the recombinant protein, the fermentation process used, and the contents of the fermentation medium. (See, e.g., Bogosian et al., (1989) Biol Chem 264:531-539.)

To examine norleucine misincorporation in a recombinant protein expression fermentation process, the following study was performed. The *E. coli* host strain 60E4 was transformed with a plasmid containing nucleic acid sequences encoding a light chain and a heavy chain of an Fab antibody fragment (SEQ ID NO:31 and SEQ ID NO:32, respectively) and used in the following fermentation studies using a water feed or methionine feed according to methods described above. The expressed recombinant proteins were then analyzed for norleucine content using methods described above.

As shown in Table 3 below, approximately 5-10% norleucine misincorporation was observed in each of the recombinant polypeptides expressed in the *E. coli* host cell 60E4 in the absence of a continuous methionine feed (i.e., a water feed). As expected, in the presence of a continuous methionine feed, norleucine was not detected (ND) in either expressed recombinant polypeptide.

TABLE 3

| Strain | Feed | Norleucine in peptide 1 (%) | Norleucine in peptide 2 (%) |
| --- | --- | --- | --- |
| 60E4 | Met | ND | ND |
| 60E4 | Water | 5.1 ± 0.7 | 10 ± 1.2 |
| 60E4 | No feed | | |
| 66H6 | Water | ND | ND |
| 66H8 | Water | ND | ND |
| 66H8 | No feed | ND | ND |
| 67B8 | Water | ND | ND |
| 67B9 | Water | ND | ND |
| 67C2 | Water | ND | ND |
| 67C3 | Water | ND | ND |

These results confirmed that norleucine misincorporation occurred in recombinant protein production in bacteria in the absence of a methionine feed.

Example 2. Construction of Methionine Biosynthetic Pathway Mutant *E. coli* Host Cells As stated above, continuous feeding of methionine during recombinant protein fermentation is often used to prevent norleucine misincorporation. As shown above in Example 1, continuous methionine feed ensured that sufficient methionine was available for the host cell, thus reducing or preventing norleucine misincorporation during recombinant protein production. To examine the effect of using an *E. coli* host cell containing mutant metA and/or metK alleles on norleucine misincorporation, instead of using a continuous methionine feed, the following studies were performed.

In the present studies, metA alleles containing the mutations R27C, Q64E, Y294C, I296S, and P298L, which result in feedback-resistant MetA, were introduced into 60E4 host cells using an allele exchange method (see Materials and Methods above) to obtain bacterial host cell strains 66H6 (60E4 metA(R27C)), 66H8 (60E4 metA(Y294C)), 6788 (60E4 metA(Q64E)), and 67B9 (60E4 metA(I296S P298L)), respectively (See Tables 2 and 3 above.)

The metK alleles containing the mutations V185E and c1132del (deletion of the cytosine base at position 1132 in the metK gene), which result in partial loss of function MetK enzymes, were introduced into 66H8 (60E4 metA(Y294C)) host cells using an allele exchange method (see Materials and Methods above) to obtain bacterial host cell strains 67C2 (66H8 metK(V185E)) and 67C3 (66H8 metK (c1132del)), respectively. (See Tables 2 and 3 above.)

These *E. coli* host cells were evaluated for norleucine misincorporation during recombinant protein production in a fermentation process performed without a continuous methionine feed. (See Example 3 below.)

Example 3. Fermentation Results

Small-scale fermentations (10 L) without a continuous methionine feed were executed utilizing the methionine biosynthetic pathway mutant bacterial strains constructed in this study. (See Table 1.) The methionine feed was either replaced with water feed or no feed was used during the fermentation process in these experiments. Three 10 L fermentations were performed using the control host cell strain 60E4 as follows: 1) a continuous methionine feed, 2) a continuous water feed, and 3) no feed.

Figure 12A:
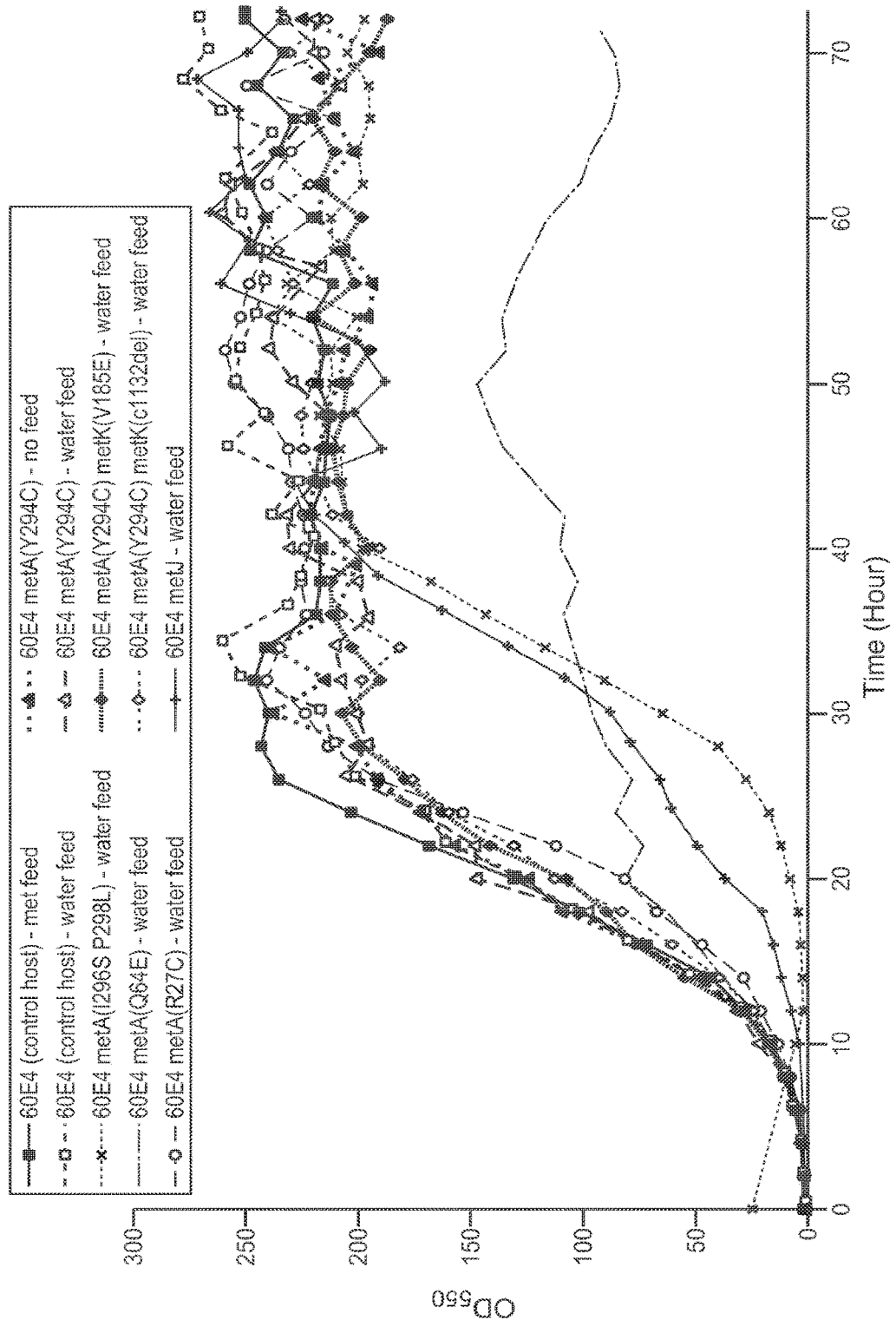
FIGS. 12A, 12B, and 12C set forth growth trends, as measured by OD$_{550}$ (FIG. 12A) and iOD$_{550}$ (FIG. 12B) of 10 L *E. coli* fermentations. The control host (60E4) fermentation was executed with a continuous methionine (■) or continuous water feed (□) (FIG. 12A). The 60E4 metA (Y294C) host fermentation was performed with continuous water feed (Δ) or no feed (▲) (FIG. 12A).
Figure 12B:
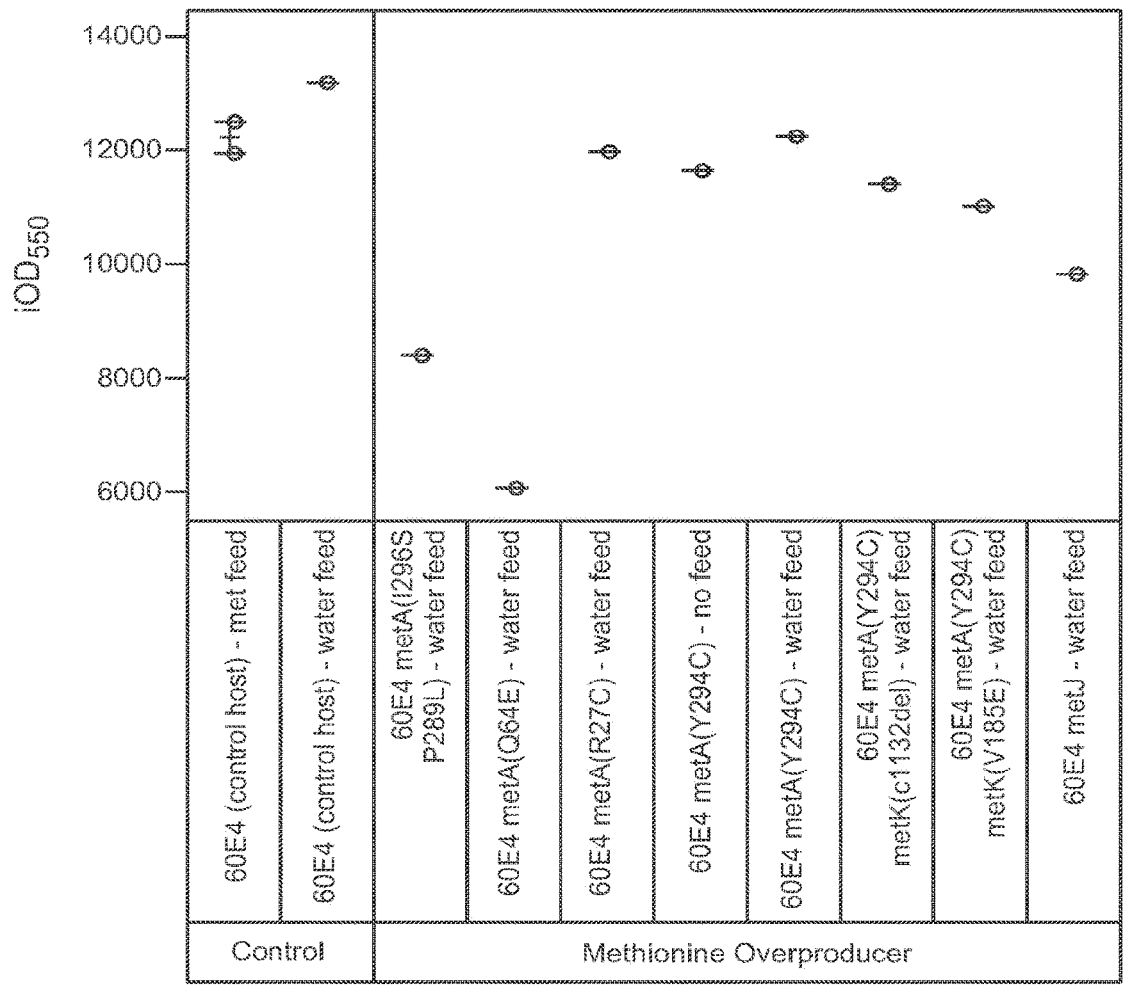

Fermentation trends for cell growth, as monitored by $OD_{550}$, are shown in FIG. 12A. Irrespective of the nature of the feed (methionine, water, or no feed), the growth of the methionine biosynthetic pathway mutant bacteria host cells 60E4 metA(R27C), 60E4 metA(Y294C), 60E4 metA (Y294C) metK(V185E), and 60E4 metA(Y294C) metK (c1132del) was comparable to that observed in control host cells during the growth phase of the fermentation (5-28 hours). However, double mutant host cells 60E4 metA (Y294C) metK(V185E), and 60E4 metA(Y294C) metK (c1132del) had lower $iOD_{550}$ (area under the growth curve from 24 hours until the end of fermentation) compared to that observed in control host cell fermentations. (See FIG. 12B.) Fermentations performed with water feed using host cells 60E4 and 60E4 metA(Y294C) had slightly higher $iOD_{550}$ compared to that observed in control host cell fermentation performed with a methionine feed and 60E4 metA(Y294C) host cell fermentation performed with no feed, respectively. The mutant cells 60E4 ΔmetJ::kan$^R$ and 60E4 metA(I296S P298L) had longer adaptation phases and as a result had lower $iOD_{550}$ compared to that observed in control host cell fermentations. (See FIGS. 12A and 12B.) The mutant host cell 60E4 metA(Q64E) grew poorly in the fermentor, reaching a maximum $OD_{550}$ of 150, which is approximately 30-40% lower compared to the maximum $OD_{550}$ observed in fermentations using other mutant host cells. (See FIG. 12A.) After 20 hours, growth of mutant host cell 60E4 metA(Q64E) reached saturation and as a result, the fermentation using this mutant host cell had the lowest iOD$_{550}$. (See FIGS. 12A and 12B.)

Figure 12C:
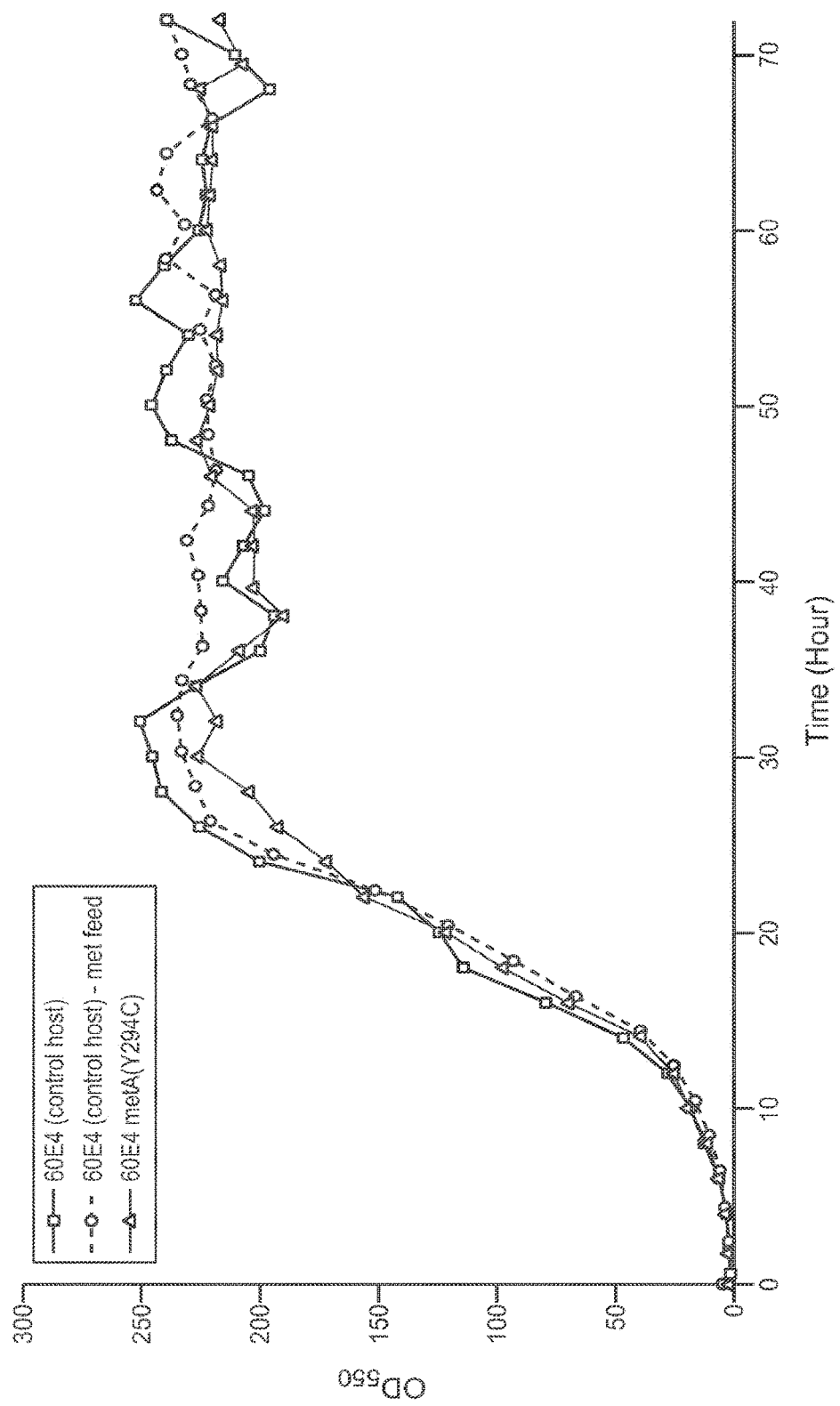

The presence or absence of a methionine feed during the fermentation did not affect growth of the 60E4 host cells. (See FIG. 12C.)

Figure 13A:
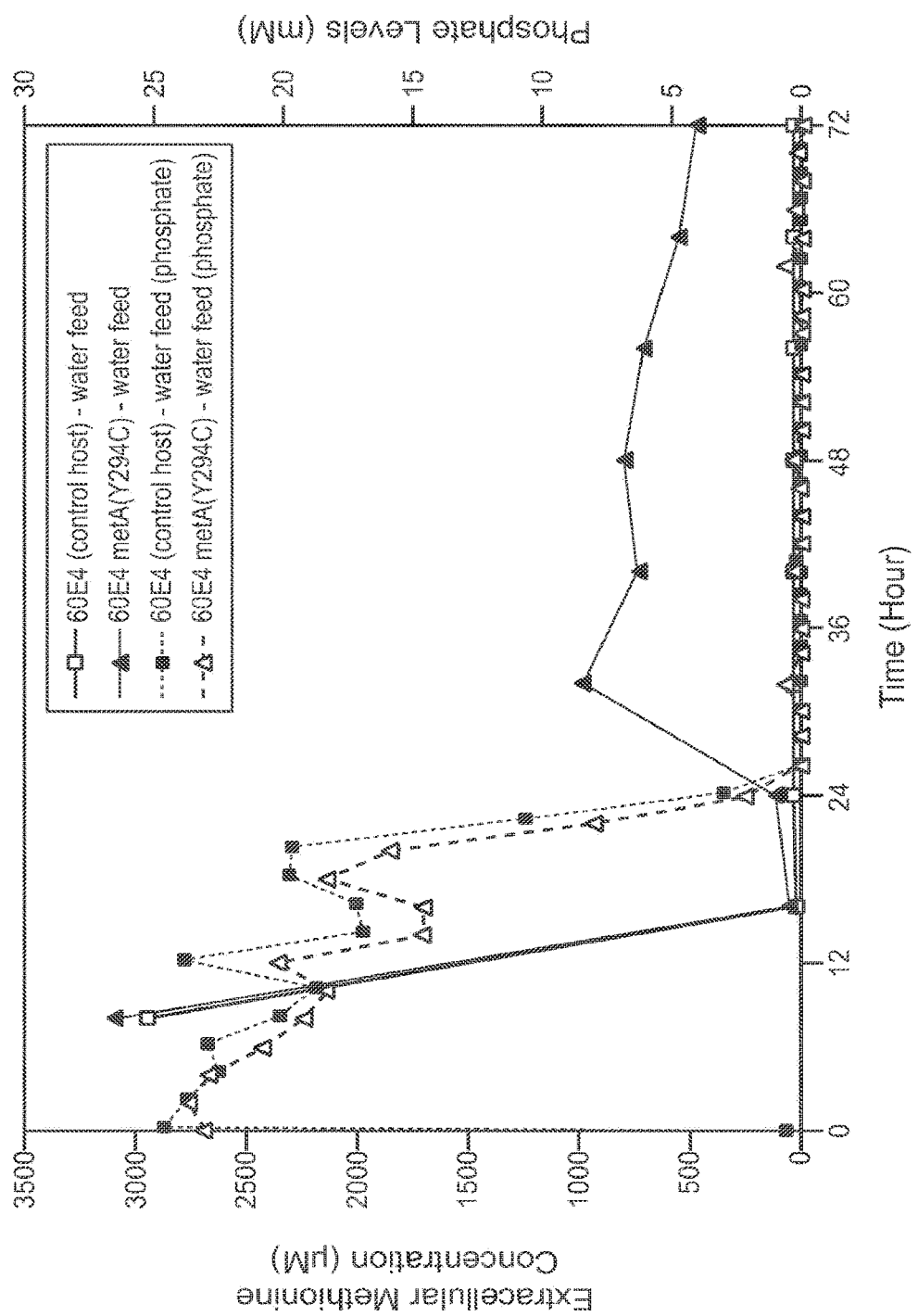
FIGS. 13A and 13B show extracellular (FIG. 13A) and intracellular (FIG. 13B) methionine levels for the control host (□) and 60E4 metA(Y294C) (Δ) host cell fermentations performed with continuous water feed. Phosphate levels in the extracellular medium are also shown in dotted line plots (FIG. 13A) and (FIG. 13B) for control host cell (□) and 60E4 metA host cell (Y294C) (Δ) fermentations performed with continuous water feed.
Figure 13B:
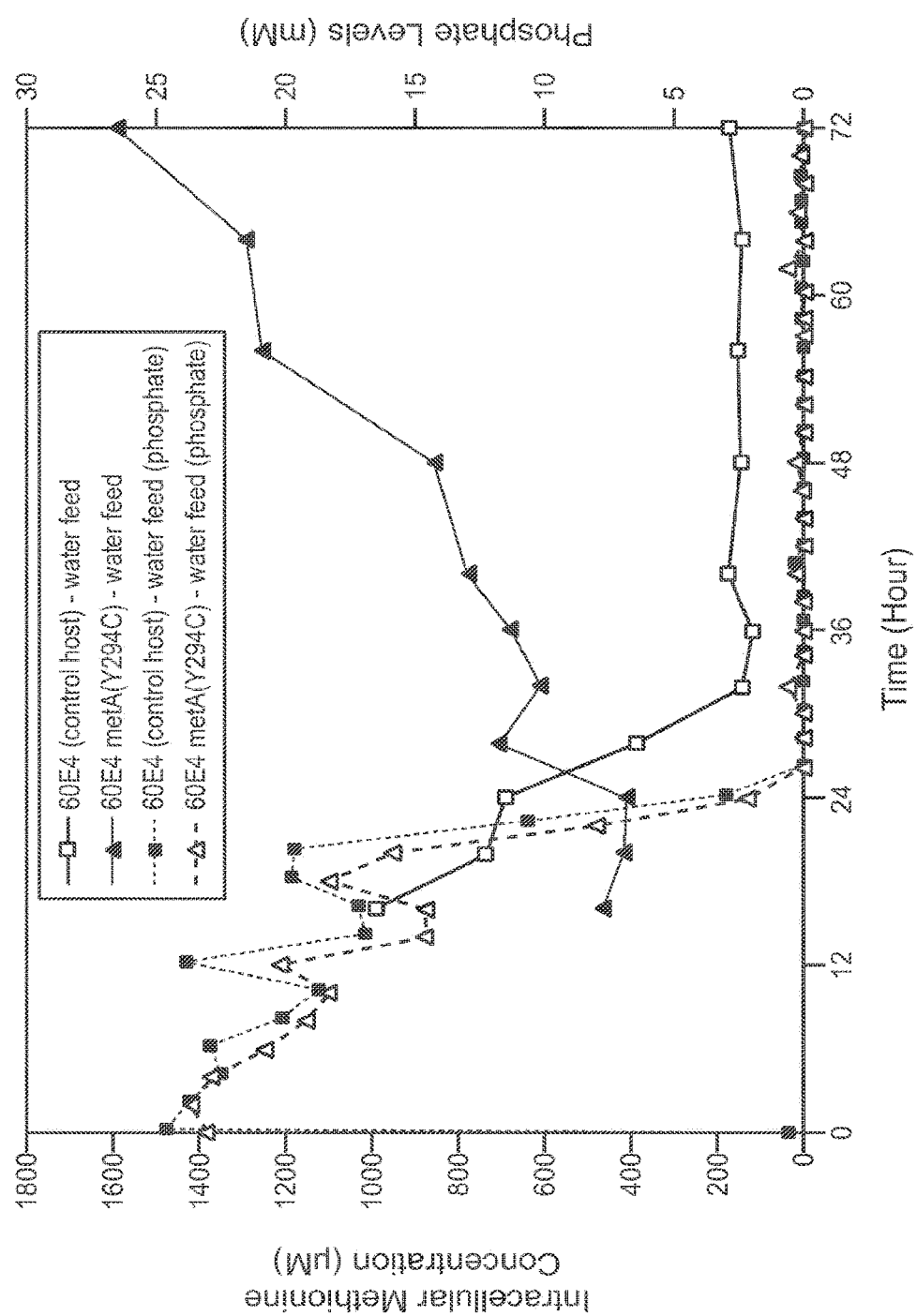
Figure 14A:
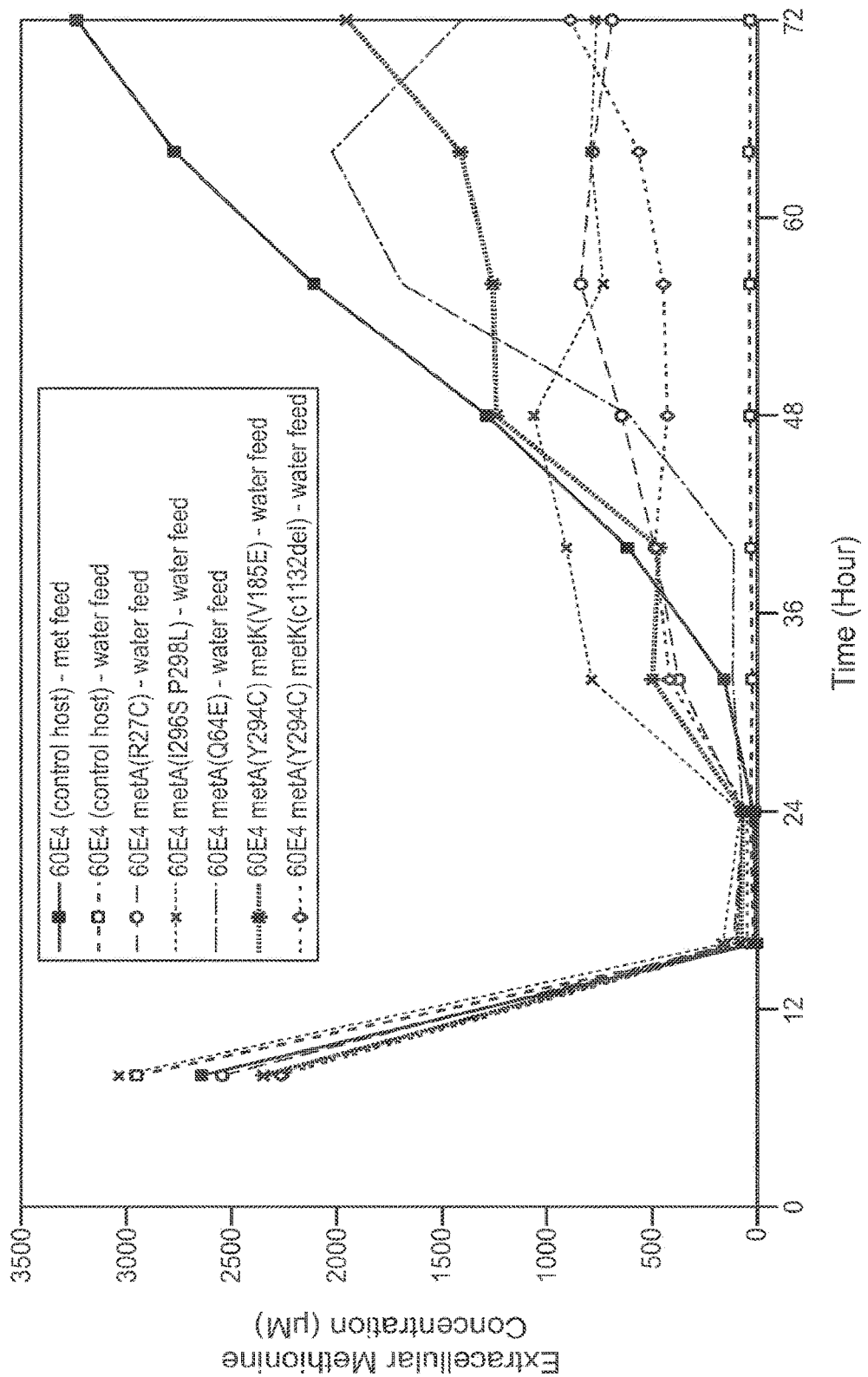
FIGS. 14A and 14B show extracellular (FIG. 14A) and intracellular (FIG. 14B) methionine levels for mutant host cell strains of the present invention. Extracellular and intracellular methionine levels are also shown for two control host cell fermentations performed with continuous methionine (■) or continuous water feed (□), respectively.
Figure 14B:
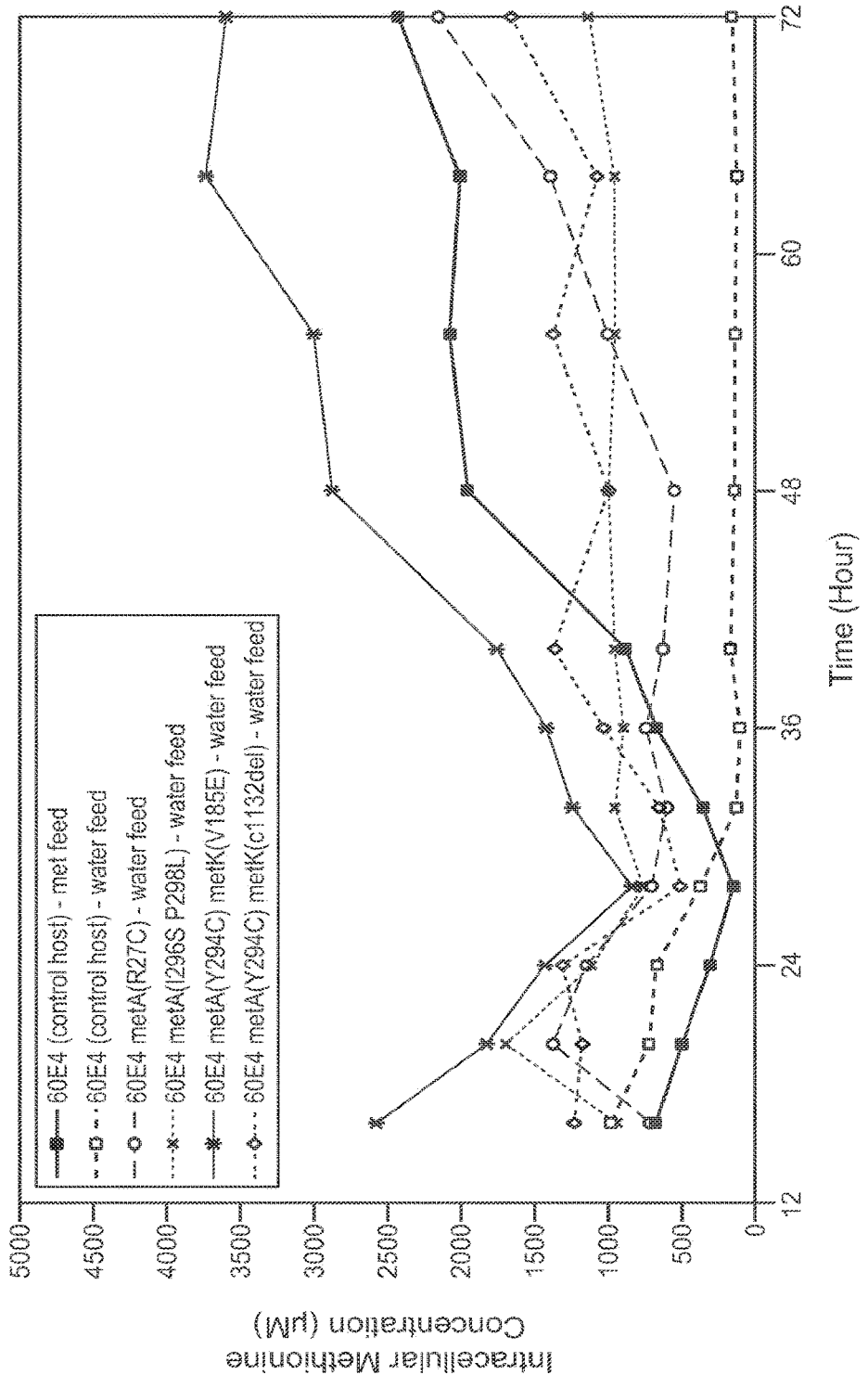

Fermentations using the methionine biosynthetic pathway mutants accumulated higher levels of methionine both in vivo (i.e., intracellular) and in the extracellular medium compared to that observed in control host cell fermentation. (See FIGS. 13A, 13B, 14A, and 14B.) At the beginning of the fermentation process, there is excess methionine (>3 mM) in the fermentation medium. As the cells begin to grow, they uptake methionine for protein synthesis, methyl donor role, and other functions. As a result, the extracellular methionine concentration gradually decreases as the cells continue to grow and the extracellular methionine levels reach less than detectable levels (<10 µM) at approximately hour 16, (See FIGS. 13A and 14A.)

At hour 16, the intracellular methionine concentrations vary from 0.5-2.5 mM (concentration is based on cell volume) among different hosts. (See FIGS. 13B and 14B.) At such high intracellular methionine concentrations, wild-type MetA would be strongly inhibited; however, feedback resistant MetA mutants may only be weakly inhibited and thus allowing the mutant host cells to produce methionine via the biosynthetic pathway. (See Usuda and Kurahashi (2005) Appl Environ Microbiol 71:3228-3234.) However, the intracellular methionine levels continued to decrease until about hour 28, at which point cell growth was considerably slowed down. It is possible that during the bacterial growth phase (5-28 hours) of the fermentations, the rate at which the methionine is utilized for protein synthesis and other cellular functions may exceed the rate at which methionine is synthesized in viva. This may explain the gradual decrease in intracellular methionine levels until the end of growth phase.

During the recombinant protein production phase of the fermentation (28 hours until the end of the fermentation), the methionine overproducing host cells continue to synthesize methionine in vivo and the intracellular methionine levels continued increasing during this phase of the fermentation process. (See FIGS. 13B and 14B.) These results suggested that during the recombinant protein production phase of the fermentation, the rate of methionine biosynthesis exceeded the rate at which methionine was utilized for various intracellular functions.

During control host cell fermentation performed with a continuous water feed, both the extracellular and intracellular methionine levels continued to decrease, reaching levels less than the limit of detection of the assay (10 µM) at about 16 hours for extracellular methionine and at about 24 hours for intracellular methionine. For a control host fermentation performed with a continuous methionine feed, the feed ensures that there is excess methionine in the cell after approximately 26 hours, the time point at which the feed is initiated. During the production phase of fermentation, the double mutant host cell 60E4 metA(Y294C) metK (V185E) accumulated more intracellular methionine compared to that observed in control host cell fermentation performed with a continuous methionine feed.

Longer adaptation phase of host cells 60E4 metA(I296S P298L) and 60E4 ΔmetJ::kan$^R$ and poor growth of host cell 60E4 metA(Q64E) compared to that observed in control host cells could potentially be due to high levels of homocysteine accumulation, a toxic intermediate in the methionine biosynthetic pathway. (See Roe et al., (2002) Microbiology 148:2215-2222; See FIG. 12A.) It was demonstrated previously that homocysteine inhibits the enzyme involved in the first step of isoleucine biosynthetic pathway, threonine deaminase, causing growth inhibition. (See Tuite et al., (2005) J Bacteriol 187:4362-4371.) This was examined by measuring the intracellular isoleucine levels in the mutant host cells. The analysis showed that the intracellular isoleucine levels were comparable to that observed in control host cells during fermentation (data not shown). The possibility of homocysteine having other toxic effects on cell growth cannot be completely ruled out. At this time, however, these differences in growth among the mutants are not fully understood.

Figure 15:
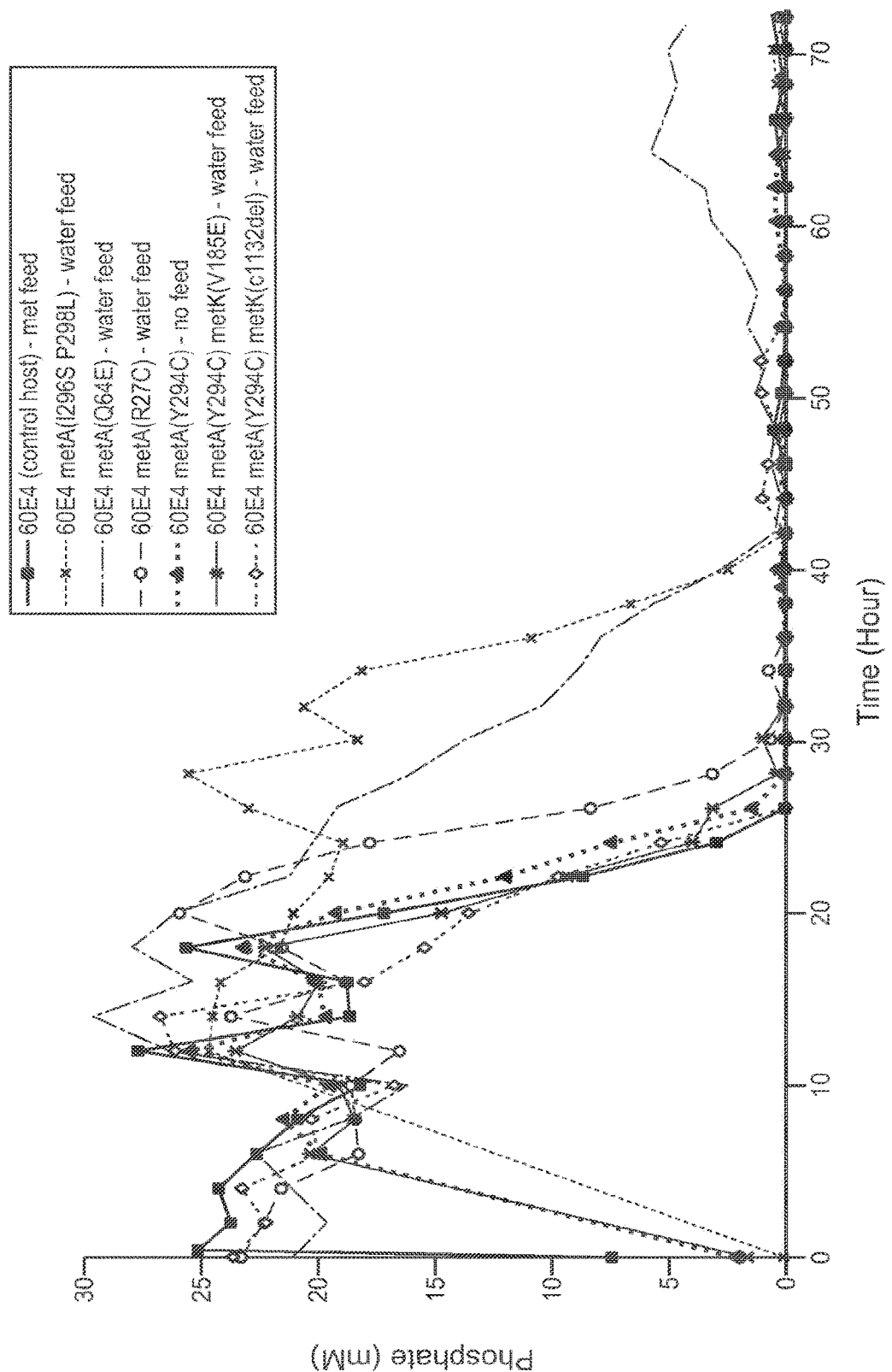
FIG. 15 shows extracellular phosphate levels during fermentations.
Figure 16A:
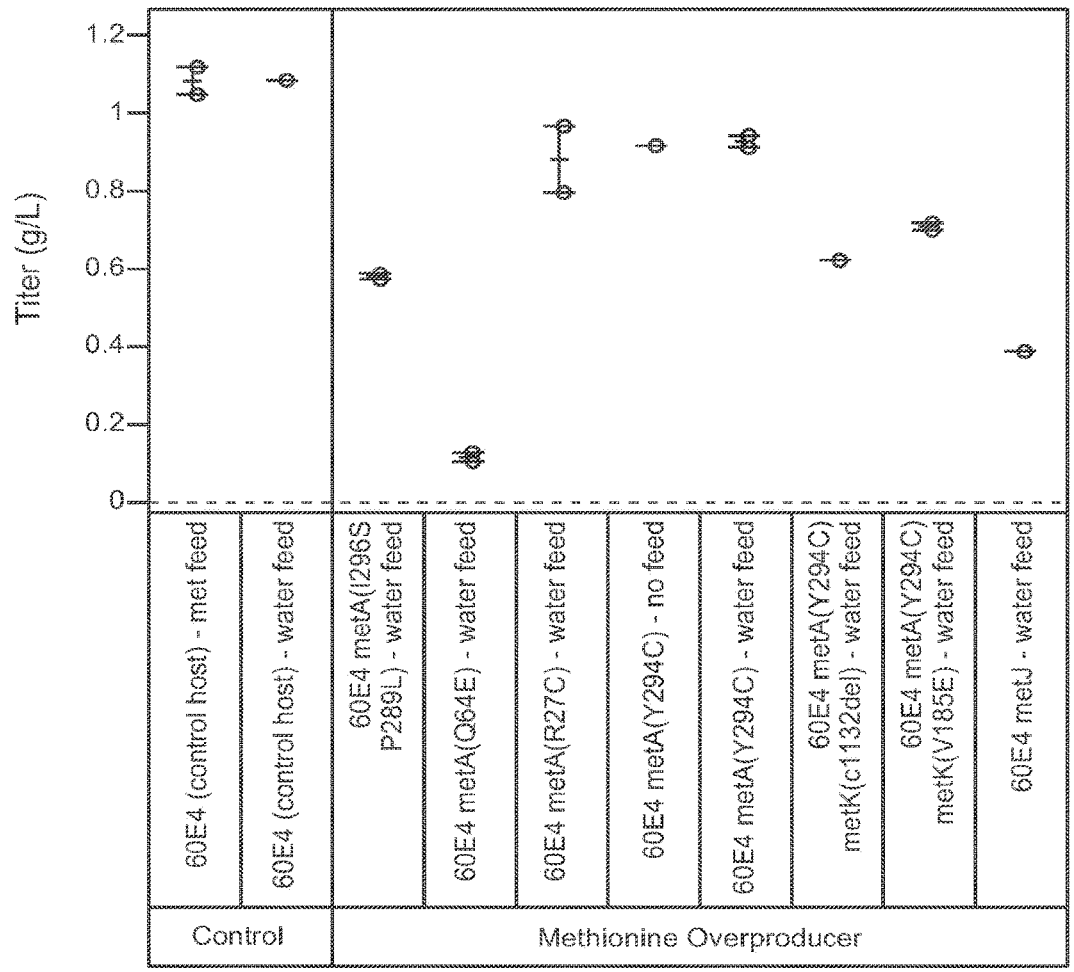
FIGS. 16A and 16B show end of run titer (FIG. 16A) and time course titer (FIG. 16B) of *E. coli* host cell fermentations. The control host cell (60E4) fermentation was performed with a continuous methionine (■) or continuous water feed (□). The 60E4 metA host cell (Y294C) fermentation was performed with a continuous water feed (Δ) or no feed (▲). Fermentations using all other mutant host cells were performed with continuous water feed.
Figure 16B:
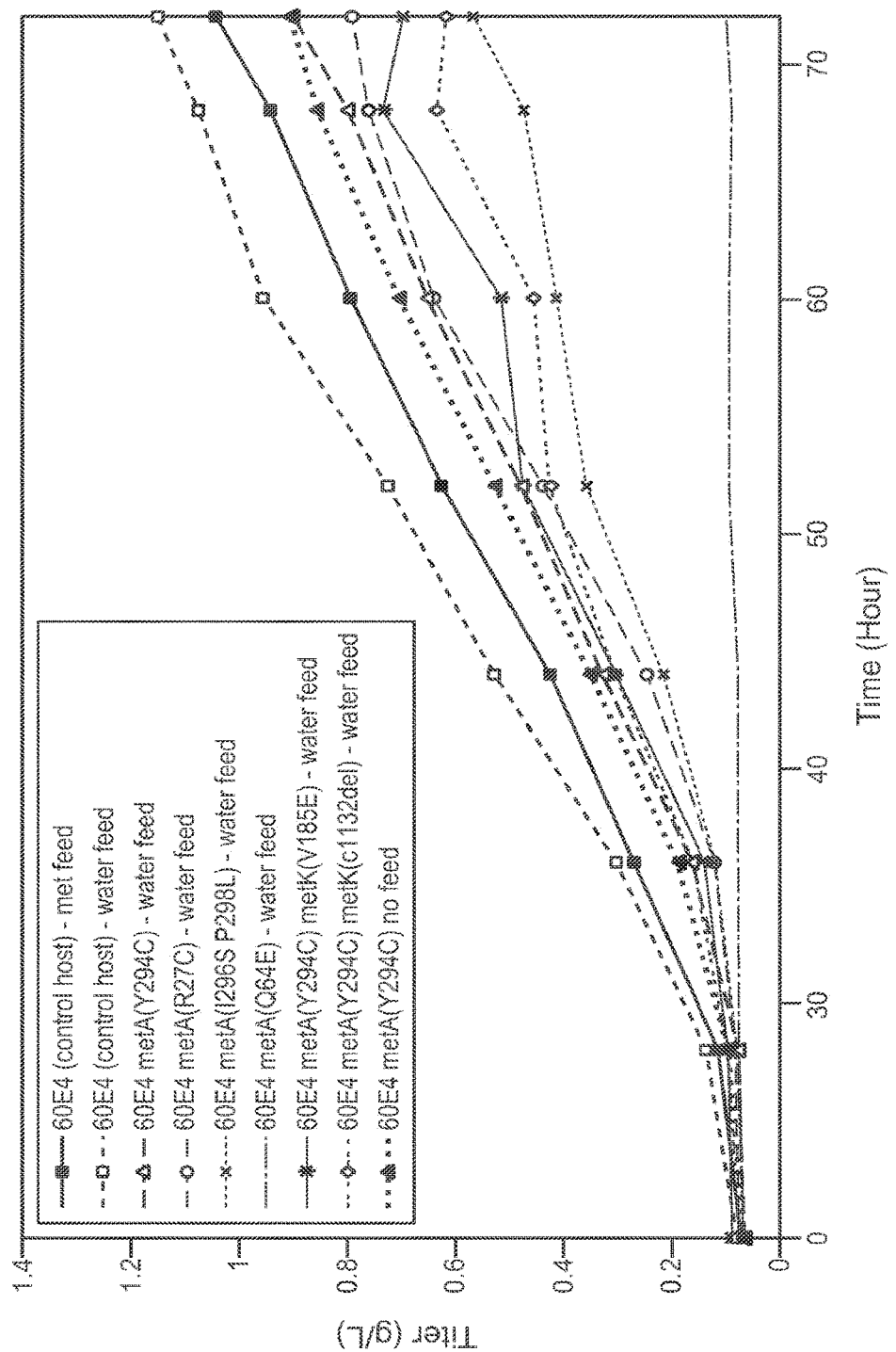
Figure 17B:
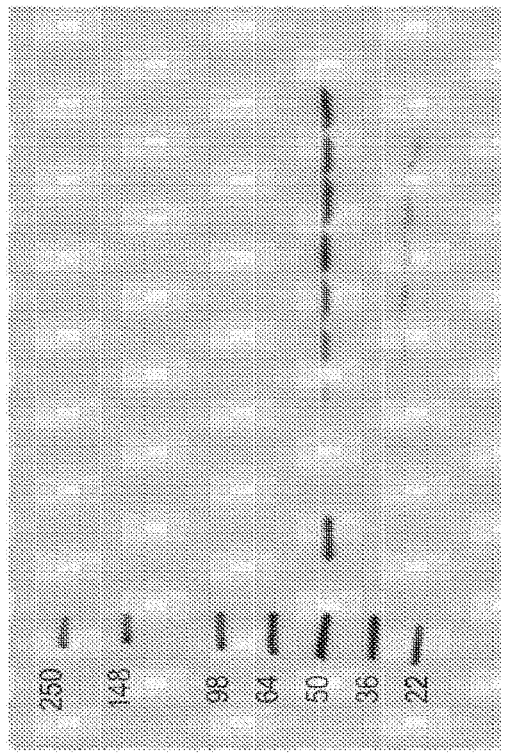
FIGS. 17A and 17B set forth results of western blots performed on whole cell broth samples obtained during the 60E4 host cell (control host cell) and the 60E4 metA host cell (Y294C) fermentations, respectively.
Figure 17A:
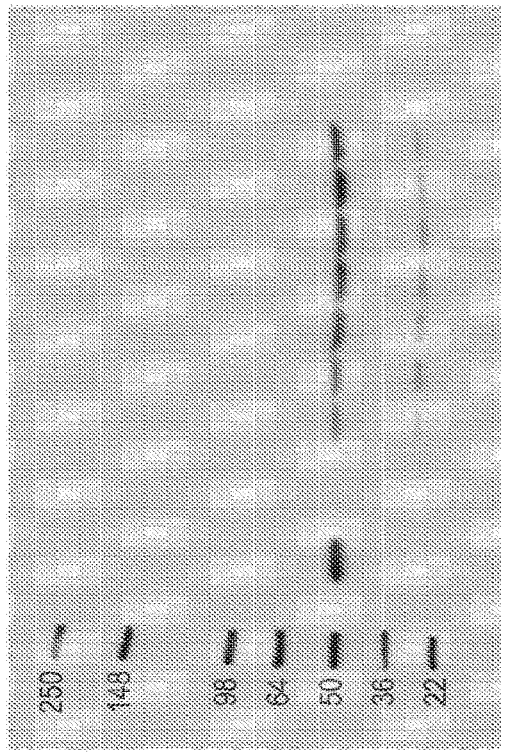

Time course for protein product titers and western blot data are shown in FIGS. 16A, 16B, and 17. The fermentation inoculated from host cell 60E4 metA(Q64E) produced less product that that observed in other host cells. Except for a brief period between 45-50 hours, phosphate levels never depleted during the 60E4 metA(Q64E) host fermentation (FIG. 15); thus, recombinant protein synthesis was low. The extended adaptation phase of the mutant host cells 60E4 metA(I296S P298L) and 60E4 ΔmetJ::kan$^R$ resulted in phosphate depletion after hour 40 which is about 12 hours later than as usually observed; hence, fermentations using these host cells had lower protein product titers compared to that observed in other mutant host cells that depleted phosphate earlier. (See FIGS. 12A, 15 and 16A.) Fermentations using the host cells 60E4 metA(R27C) and 60E4 metA(Y294C) produced the highest protein product titers among all the mutant host cells examined.

Fermentations using the metA metK double mutant host cells, 60E4 metA(Y294C) metK(V185E) and 60E4 metA (Y294C) metK(c1132del), produced somewhat low protein product titers in spite of having comparable growth to control host cells. These double mutant host cells have a mutation in the metK gene that results in a partial loss of function MetK. The product of MetK is s-adenosylmethionine (SAM), a methyl donor for many reactions in bacterial cells. It is not known, however, why decreased SAM levels would affect protein product titers. A continuous feed during the fermentation process could result in dilution of the culture medium that could possibly result in lower cell densities and possibly lower product titers. The growth and titers of host cell 60E4 metA(Y294C) fermentation without any feed was comparable to that observed in fermentations using the same host cell performed with a continuous water feed.

Example 4. Norleucine Misincorporation

As described above, norleucine misincorporation in proteins due to the levels of methionine in the cell are low enough that norleucine can compete for methionine residues in the charging of methionyl tRNA during protein synthesis. As shown in Example 1 above, control host cell fermentation performed without a methionine feed resulted in high levels of norleucine misincorporation in the recombinant protein (Table 3). Low intracellular methionine levels during the production phase of control host cell fermentation performed without a methionine feed indicated that norleucine residues could be competing for methionine residues in the recombinant protein. However, high levels of extracellular and intracellular methionine were observed during the production phase of the mutant host cell fermentations. (See FIGS. 13B and 14B.) As a result of elevated intracellular methionine levels, norleucine misincorporation is expected to be minimal or eliminated in using such host cell fermentations.

Trypsin digestion of the recombinant protein yielded 2 methionine containing peptides: peptide 1: LSCAASGYDFTHYGM$^{34}$NWVR (SEQ ID NO:35); and peptide 2: STAYLQM$^{83}$NSLR (SEQ ID NO:36). Peptide map analysis indicated that the recombinant protein pools purified from the mutant host cell fermentations contained less than detectable levels of norleucine misincorporation, while the control host cell fermentation performed without a methionine feed accumulated high levels of norleucine in both methionine containing peptides. (See Table 3.) These results showed that use of *E. coli* host cell strains of the present invention resulted in the reduction or prevention of norleucine incorporation into heterologous (e.g., recombinant) polypeptides.

Example 5. Additional Bacteria Host Cells

In addition to experiments performed using host cell 60E4 or host cells derived from 60E4, two other bacteria host cells were developed and examined for growth, norleucine misincorporation, and recombinant protein production as follows.

Bacteria host cells 66F8 and 64B4 (as well as bacteria host cell 60E4) are described above in Table 2. As shown in Table 2, there are several differences in the genotype of host cells 60E4 compared to host cells 66F8 and 64B4 (which share a similar genotype).

Three different fermentation processes were examined using host cell 60E4 (fermentation process AF1), host cell 66F8 (fermentation process AF2), and host cell 64B4 (fermentation process AF3). Table 4 below shows the differences in various fermentation parameters (pH, agitation, culture duration, and feed start time) of each of the fermentation processes (AF1, AF2, and AF3) examined.

TABLE 4

|  | AF1 | AF2 | AF3 |
|---|---|---|---|
| Control host | 60E4 | 66F8 | 64B4 |
| pH | 7.0 | 7.0 | 7.3 |
| Agitation (rpm) | 850[a] | 650 | 650 |
| Culture duration (hours) | 72 | 50 | 72 |
| Feed (met or water) start timing (OD$_{550}$) | 200 | 150 | 150 |

Figure 19A:
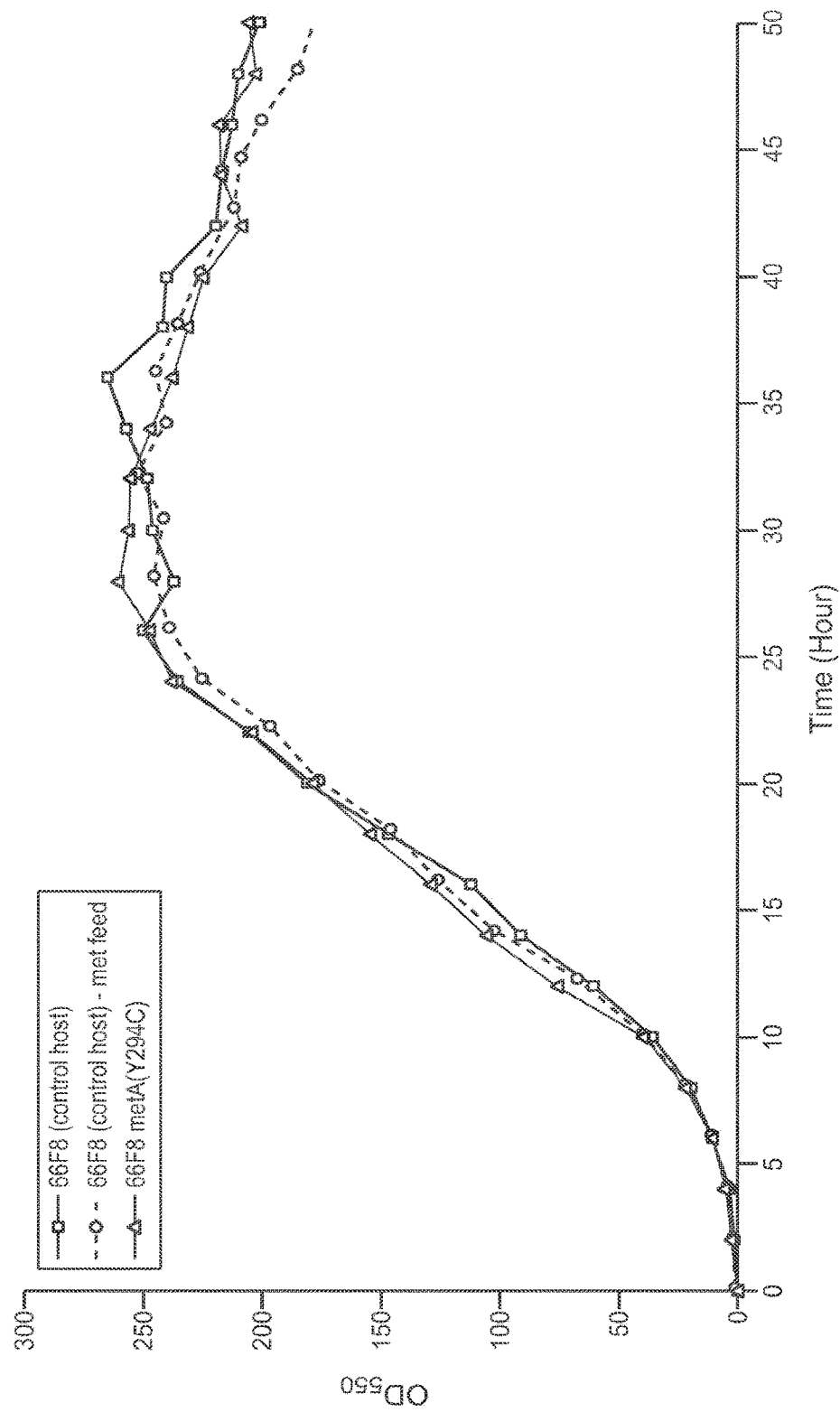
FIGS. 19A and 19B set forth growth trends of 10 L *E. coli* fermentations, as measured by OD$_{550}$. The control hosts (66F8 or 64B4) fermentation processes AF2 or AF3, respectively, were executed with no feed (squares) or a continuous methionine feed (circles). The 66F8 metA(Y294C) and the 64B4 metA(Y294C) host fermentations were performed with no feed (triangles).
Figure 19B:
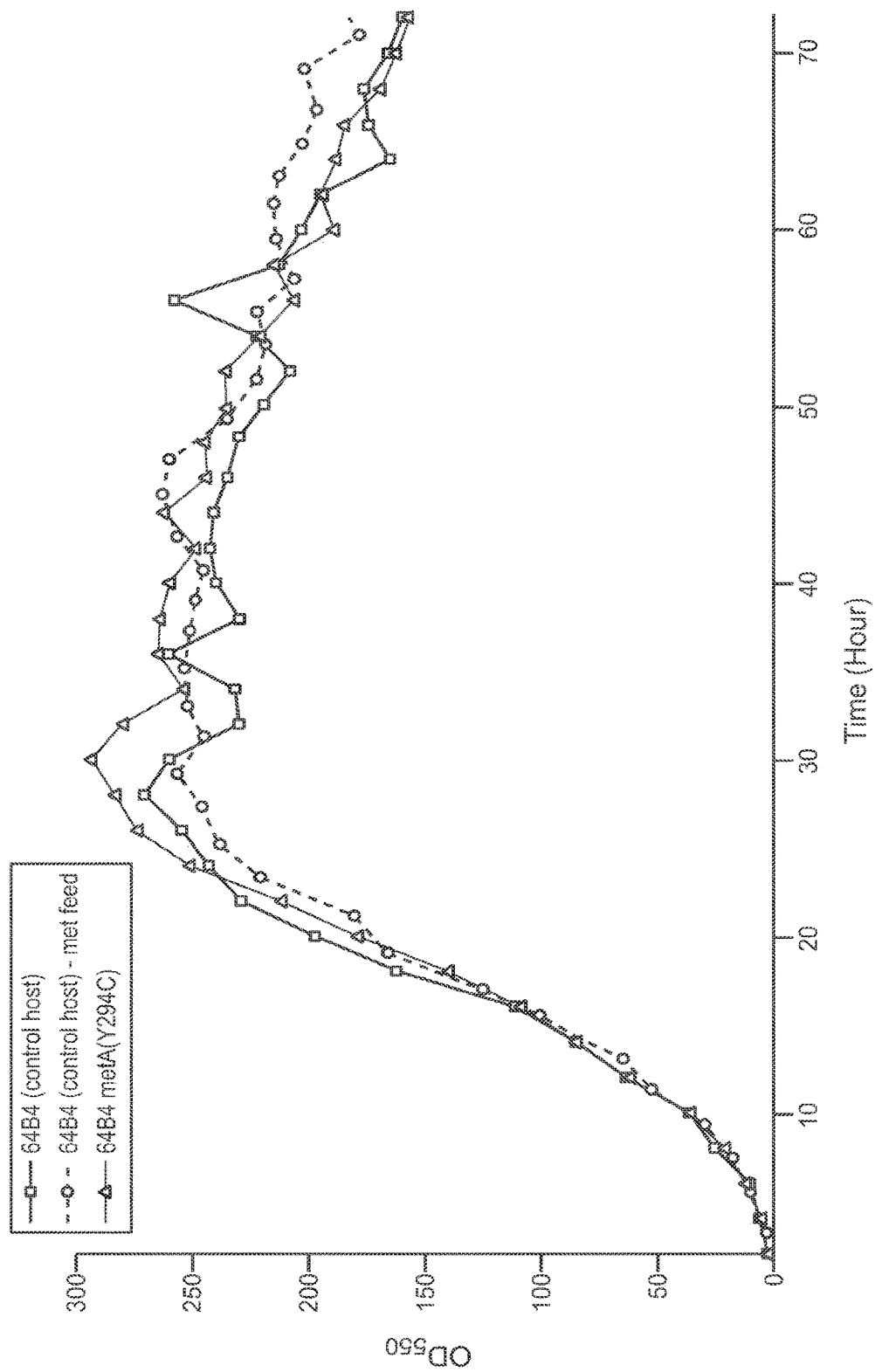

[a]After the cells reach an OD$_{550}$ of 200, agitation is reduced to 800 and then stepwise by 100 mm every 2 hours until 500 mm is reached The metA(Y294C) allele was introduced into the host cells 66F8 and 6484 using methods as described above in Example 1 for host cell 60E4. Fermentations performed using the 66F8 metA(Y294C) and the 64B4 metA(Y294C), using fermentation process AF2 and AF3, respectively, showed host cell growth comparable to that observed with their parent host cells. (See FIGS. 19A and 19B; and Table 5 below.)

Example 6. Comparison of *E. coli* Host Cell Growth Rates and Recombinant Protein Product Yields Growth rates and recombinant protein product yields were examined in each of the *E. coli* host strains 60E4 metA (Y294C), 66F8 metA(Y294C), and 6484 metA(Y294C) using fermentation process AF1, AF2, AF3, respectively 10 L fermentations were performed as described above in Example 3 for host cells of strain 60E4, using fermentation process modifications as outlined above in Table 4 for each fermentation process.

Growth rates and recombinant protein product yields observed for the various host cells of strain 60E4 are discussed in detail above in Example 3.

Figure 20A:
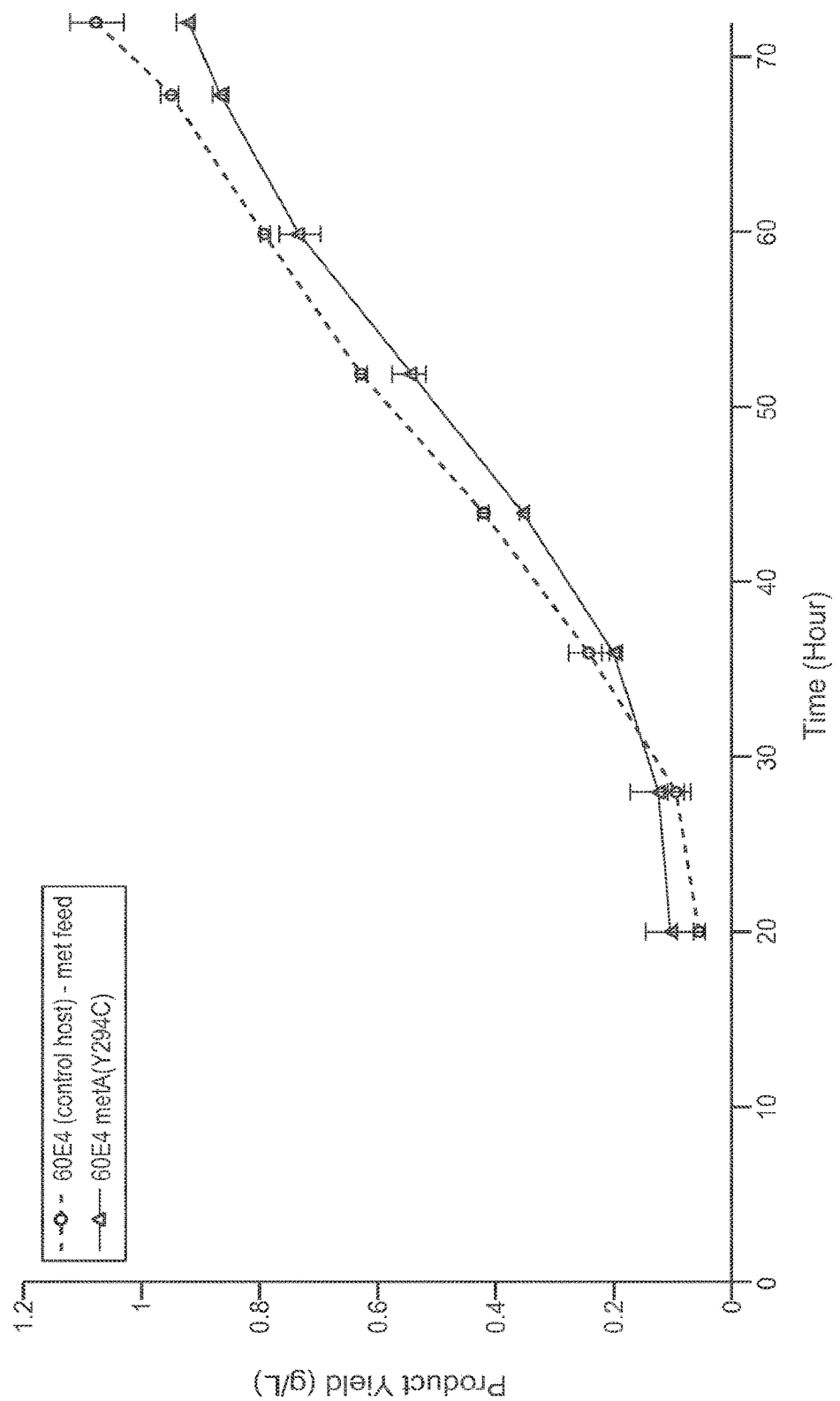
FIGS. 20A, 20B, and 20C set forth recombinant protein product yields using host strains 60E4 (control host) and 60E4 metA(Y294C), 66F8 (control host) and 66F8 metA (Y294C), and 64B4 (control host) and 64B4 metA(Y294C), respectively.
Figure 20B:
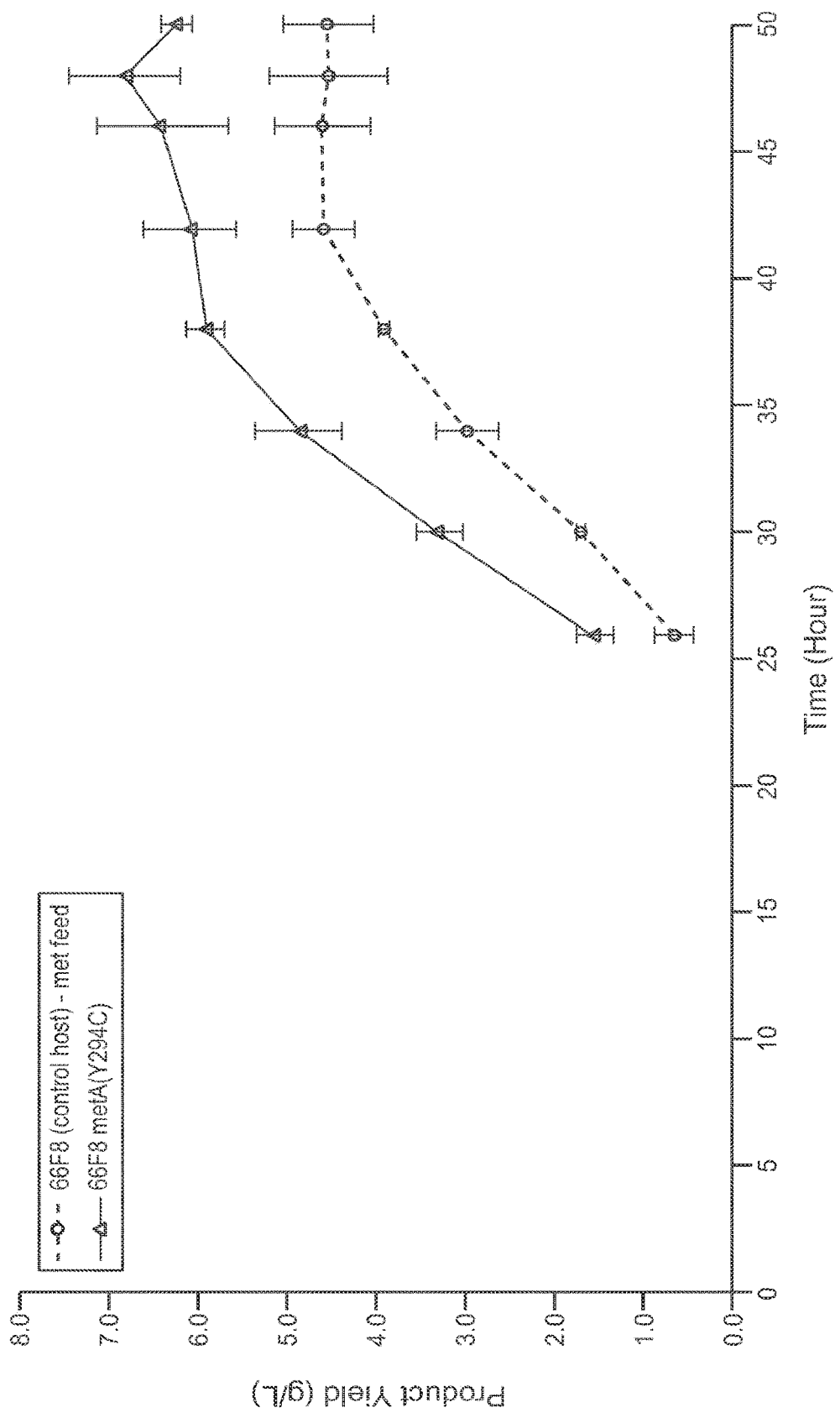
Figure 20C:
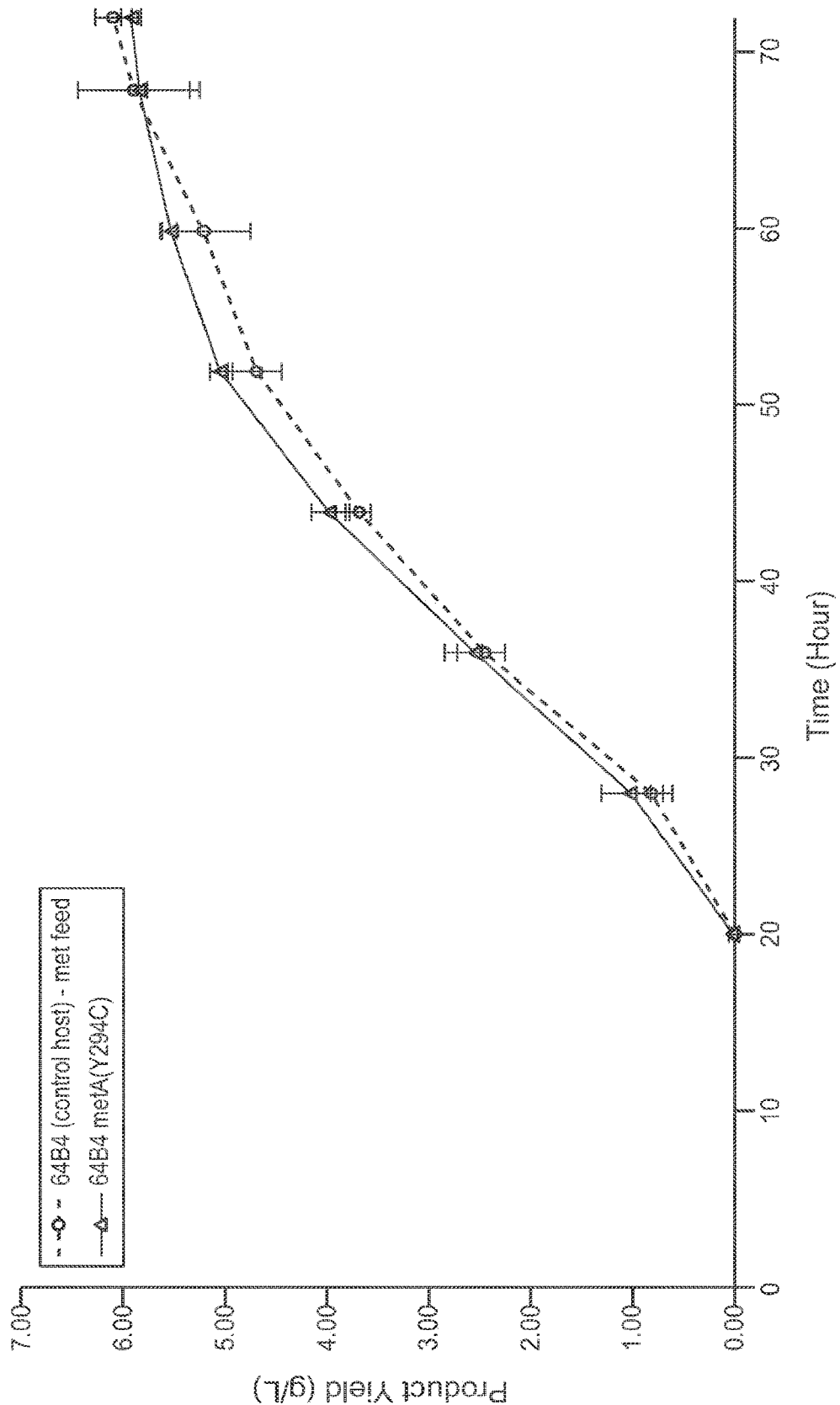

As shown in FIGS. 20A, 20B, and 20C, recombinant protein product yields obtained using host strains 60E4 metA(Y294C), 66F8 metA(Y294C), and 64B4 metA (Y294C) was comparable to that observed using host strains 60E4, 66F8, and 64B84. (See also Table 5 below.) The presence or absence of methionine feed did not affect recombinant protein yields obtained from the 60E4 host cell fermentation.

TABLE 5

| Host | Feed | Process | Growth rate, $\mu$ (hr$^{-1}$)[a] | Product yield (g/L)[b] |
|---|---|---|---|---|
| 60E4 (control host) | met | AF1 | 0.325 ± 0.02 | 1.077 ± 0.047 |
| 60E4 (control host) | water | AF1 | 0.343 | 1.152 |
| 60E4 (control host) | none | AF1 | 0.358 ± 0.15 | 1.098 |
| 60E4 metJ | water | AF1 | 0.232 | 0.486 |
| 60E4 metA(R27C) | water | AF1 | 0.332 | 0.792 |
| 60E4 metA(Y294C) | water | AF1 | 0.333 | 0.906 |
| 60E4 metA(Y294C) | none | AF1 | 0.377 ± 0.023 | 0.924 ± 0.017 |
| 60E4 metA(Q64E) | water | AF1 | 0.294 | 0.102 |
| 60E4 metA(I296S P298L) | water | AF1 | 0.278 | 0.57 |
| 60E4 metA(Y294C) metK (V185E) | water | AF1 | 0.356 | 0.696 |
| 60E4 metA(Y294C) metK (V185E) | water | AF1 | 0.301 | 0.618 |
| 60E4 metA(Y294C) | none[c] | AF1 | 0.314 | 0.936 |
| 66F8 (control host) | met | AF2 | 0.459 ± 0.025 | 4.5 ± 0.5 |
| 66F8 metA(Y294C) | none | AF2 | 0.381 ± 0.03 | 6.7 ± 0.2 |
| 64B4 (control host) | met | AF3 | 0.406 ± 0.037 | 5.1 ± 0.2 |
| 64B4 metA(Y294C) | none | AF3 | 0.361 ± 0.01 | 5.4 ± 0.1 |

[a]For the 60E4 metJ and 60E4 metA metA(I296S P298L) hosts, the time between 6-14 hours and 14-22 hours respectively was used to calculate $\mu$. For all other hosts, 2-10 hours was used to calculate $\mu$. The values of $\mu$ shown are the average of n = 2 runs.
[b]The values shown are the average of n = 2 runs.

Example 7. Comparison of Norleucine Misincorporation

Three different recombinant protein product purification processes were used, each specific to fermentation process AF1 (for host cell 60E4), AF2 (for host cell 66F8), and AF3 (for host cell 6484). Table 6 below shows the differences in the various purification processes used for each of the fermentation processes (i.e., AF1, AF2, and AF3) examined.

TABLE 6

|  | AF1 | AF2 | AF3 |
|---|---|---|---|
| Flocculant[a] | MgSO$_4$ (50 mM) | MgSO$_4$ (50 mM) | Polyethyleneimine |
| Homogenate hold | 3 hours at 35° C. | 21 hours at 30° C. | 12 hours at 30° C. |
| Affinity resin | Protein G | Protein G | MabSelect Sure |
| Elution buffer | Citric acid | Citric acid | Glycine phosphate |

[a]Final concentrations are indicated for the flocculant

Norleucine quantification was performed using LC-MS analysis on tryptic peptides for each of the recombinant protein products as described above.

Trypsin digestion of the recombinant protein produced by the 60E4 host yielded 2 methionine-containing peptides (Table 7). Trypsin digestion of the recombinant protein produced by the 66F8 host yielded 3 methionine-containing peptides (Table 8). Trypsin digestion of the recombinant protein produced by the 64B84 host yielded 6 methionine-containing S5 peptides (Table 9).

TABLE 7

| Tryptic peptides | SEQ ID NO: | 60E4 met feed | 60E4 | 60E4 metA(Y294C) |
|---|---|---|---|---|
| STAYLQMNSLR | 36 | ND | 10 ± 1.2 | ND |
| LSCAASGYDFTHYGMNWVR | 35 | ND | 5.1 ± 0.7 | ND |

TABLE 8

| Tryptic peptides | SEQ ID NO: | 66F8 met feed | 66F8 | 66F8 metA(Y294C) |
|---|---|---|---|---|
| ASGYTFTNYG<u>M</u>NWVR | 37 | ND | 2.1 ± 0.4 | ND |
| QAPGQGLEW<u>M</u>GWINTYTGETTYADDFK | 38 | ND | 0.7 ± 0.2 | ND |
| VTITCITSTDIDDD<u>M</u>NWYQQKPGK | 39 | ND | 1 ± 0.3 | ND |

TABLE 9

| Tryptic peptides | SEQ ID NO: | 64B4 met feed | 64B4 | 64B4 metA(Y294C) |
|---|---|---|---|---|
| GLEWVG<u>M</u>IDPSNSDTR | 40 | ND | 1.3 ± 0.3 | ND |
| NTAYLQ<u>M</u>NSLR | 41 | ND | 1.3 ± 0.3 | ND |
| DTL<u>M</u>ISR | 42 | ND | 2.4 ± 0.4 | ND |
| EE<u>M</u>TK | 43 | ND | 2.2 ± 0.5 | ND |
| WQQGNVFSCSV<u>M</u>HEALHNHYTQK | 44 | ND | 1.5 ± 0.4 | ND |
| DIQ<u>M</u>TQSPSSLSASVGDR | 45 | ND | 1.3 ± 0.2 | ND |

Recombinant protein purified from the AF1 fermentation process performed without a methionine feed using the 60E4 host accumulated 5.1% and 10% norleucine at the two methionine residues in the protein (Table 7). No norleucine was detected in the recombinant protein purified from the AF1 fermentations performed without a methionine feed using the hosts 60E4 metA(Y294C) (Table 7), 60E4 metA (R27C), 60E4 metK(294C) metK(V85E), and 60E4 metA (Y294C) metK(c1132del) (data not shown).

When the 60E4 metA(Y294C) host fermentation was supplemented with norleucine (0.15 mM final concentration) in the fermentation medium, no norleucine was observed in the recombinant protein, indicating that the bacterial host cells of the present invention make enough methionine in the cell to prevent norleucine misincorporation during recombinant protein synthesis.

About 2.7%, 0.7%, and 1% norleucine misincorporation was observed in the three methionine-containing tryptic peptides obtained from the recombinant protein produced using AF2 fermentation process performed without methionine feed using the 66F8 host. (See Table 8.) Similarly there was about 1.3%, 1.3%, 2.4%, 2.2%, 1.5%, and 1.3% norleucine misincorporation in the six methionine-containing tryptic peptides obtained from the recombinant protein produced using AF3 process performed without met feed using the 64B4 host. (See Table 9.) However, no norleucine was detected in the recombinant proteins purified from AF2 and AF3 fermentation processes using the 66F8 metA(Y294C) host and 64B4 metA(Y294C) hosts, respectively. (See Tables 8 and 9 above.)

The tryptic peptide map analyses indicated that the recombinant protein pools purified from the mutant host cell fermentations contained less than detectable levels of norleucine misincorporation, while the control host cell fermentation performed without a methionine feed accumulated high levels of norleucine in the methionine-containing peptides. These results showed that use of *E. coli* host cell strains of the present invention resulted in the reduction or prevention of norleucine incorporation into heterologous (e.g., recombinant) polypeptides.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method for reducing norleucine misincorporation into a protein or a polypeptide, the method comprising expressing the protein or the polypeptide in a microorganism, wherein the microorganism comprises a mutant metA allele, wherein the mutant metA allele comprises a nucleic acid sequence selected from the group consisting of SEQ ID NO:23, SEQ ID NO:24, SEQ ID NO:25, and SEQ ID NO:26.

2. A method for reducing norleucine misincorporation into a protein or a polypeptide, the method comprising expressing the protein or the polypeptide in a microorganism, wherein the microorganism comprises a mutant metK allele, wherein the mutant metK allele comprises a nucleic acid sequence selected from the group consisting of SEQ ID NO:27 and SEQ ID NO:28.

3. A method for reducing norleucine misincorporation into a protein or a polypeptide, the method comprising expressing the protein or the polypeptide in a microorganism, wherein the microorganism comprises a mutant metA allele and a mutant metK allele, wherein the mutant metA allele comprises a nucleic acid sequence selected from the group consisting of SEQ ID NO:23, SEQ ID NO:24, SEQ ID NO:25, and SEQ ID NO:26, and further wherein the mutant metK allele comprises a nucleic acid sequence selected from the group consisting of SEQ ID NO:27and SEQ ID NO:28.

4. The method of claim 1, wherein the microorganism is a bacteria.

5. The method of claim 4, wherein the bacteria is *E. coli*.

6. A method for producing a protein or a polypeptide in an *E. coli* host cell, wherein the protein or the polypeptide contains no detectable levels of norleucine residues, the method comprising expressing in the *E. coli* host cell a nucleic acid encoding the protein or the polypeptide under culture conditions suitable to allow for expression of the protein or the polypeptide, wherein the *E. coli* host cell comprises a mutant metA allele, wherein the mutant metA allele encodes for MetA having an amino acid sequence encoded by a nucleic acid sequence selected from the group consisting of SEQ ID NO:23, SEQ ID NO:24, SEQ ID NO:25, and SEQ ID NO:26.

7. A method for producing a protein or a polypeptide in an *E. coli* host cell, wherein the protein or the polypeptide contains no detectable levels of norleucine residues, the method comprising expressing in the *E. coli* host cell a nucleic acid encoding the protein or the polypeptide under culture conditions suitable to allow for expression of the protein or the polypeptide, wherein the *E. coli* host cell comprises a mutant metK allele, wherein the mutant metK allele encodes for MetK having an amino acid sequence encoded by a nucleic acid sequence selected from the group consisting of SEQ ID NO:27 and SEQ ID NO:28.

8. The method of claim 6, wherein the protein or the polypeptide is an antibody or an antibody fragment.

9. The method of claim 8, wherein the antibody or the antibody fragment is an anti-VEGF antibody or an anti-VEGF antibody fragment.

10. The method of claim 6, wherein the protein or the polypeptide is an antibody or an antibody fragment selected from the group consisting of an anti-VEGF antibody or an anti-VEGF antibody fragment, and wherein the nucleic acid encoding the anti-VEGF antibody or the anti-VEGF antibody fragment is selected from the group consisting of a nucleic acid encoding the amino acid sequence of SEQ ID NO:46 and a nucleic acid encoding the amino acid sequence of SEQ ID NO:47.

11. The method of claim 6, wherein the protein or the polypeptide is an antibody or an antibody fragment selected from the group consisting of an anti-VEGF antibody or an anti-VEGF antibody fragment, and wherein the nucleic acid encoding the anti-VEGF antibody or the anti-VEGF antibody fragment is selected from the group consisting of a nucleic acid sequence comprising SEQ ID NO: 33 and a nucleic acid sequence comprising SEQ ID NO:34.

12. The method of claim 8, wherein the antibody or the antibody fragment is an anti-Factor D antibody or an anti-Factor D antibody fragment.

13. The method of claim 6, wherein the protein or the polypeptide is an antibody or an antibody fragment selected from the group consisting of an anti-Factor D antibody and an anti-Factor D antibody fragment, and wherein the nucleic acid encoding the anti-Factor D antibody or the anti-Factor D antibody fragment is selected from the group consisting of a nucleic acid encoding the amino acid sequence of SEQ ID NO:48 and a nucleic acid encoding the amino acid sequence of SEQ ID NO:49.

14. The method of claim 8, wherein the antibody or the antibody fragment is an anti-MET antibody or an anti-MET antibody fragment.

15. The method of claim 6, wherein the protein or the polypeptide is an antibody or an antibody fragment selected from the group consisting of an anti-MET antibody and an anti-MET antibody fragment, and wherein the nucleic acid encoding the anti-MET antibody or the anti-MET antibody fragment is selected from the group consisting of a nucleic acid encoding the amino acid sequence of SEQ ID NO: 50, a nucleic acid encoding the amino acid sequence of SEQ ID NO: 51, and a nucleic acid encoding the amino acid sequence of SEQ ID NO:52.

16. The method of claim 6, wherein expressing the protein or the polypeptide in the *E. coli* host cell is performed in the absence of exogenously added methionine to the culture medium or without a methionine feed.

17. The method of claim 2, wherein the microorganism is a bacteria.

18. The method of claim 17, wherein the bacteria is *E. coli*.

19. The method of claim 3, wherein the microorganism is a bacteria.

20. The method of claim 19, wherein the bacteria is *E. coli*.

21. The method of claim 7, wherein the protein or the polypeptide is an antibody or an antibody fragment.

22. The method of claim 21, wherein the antibody or the antibody fragment is an anti-VEGF antibody or an anti-VEGF antibody fragment.

23. The method of claim 21, wherein the antibody or the antibody fragment is an anti-Factor D antibody or an anti-Factor D antibody fragment.

24. The method of claim 21, wherein the antibody or the antibody fragment is an anti-MET antibody or an anti-MET antibody fragment.

25. The method of claim 7, wherein the protein or the polypeptide is an antibody or an antibody fragment selected from the group consisting of an anti-VEGF antibody or an anti-VEGF antibody fragment, and wherein the nucleic acid encoding the anti-VEGF antibody or the anti-VEGF antibody fragment is selected from the group consisting of a nucleic acid encoding the amino acid sequence of SEQ ID NO:46 and a nucleic acid encoding the amino acid sequence of SEQ ID NO:47.

26. The method of claim 7, wherein the protein or the polypeptide is an antibody or an antibody fragment selected from the group consisting of an anti-VEGF antibody or an anti-VEGF antibody fragment, and wherein the nucleic acid encoding the anti-VEGF antibody or the anti-VEGF antibody fragment is selected from the group consisting of a nucleic acid sequence comprising SEQ ID NO: 33 and a nucleic acid sequence comprising SEQ ID NO: 34.

27. The method of claim 7, wherein the protein or the polypeptide is an antibody or an antibody fragment selected from the group consisting of an anti-Factor D antibody and an anti-Factor D antibody fragment, and wherein the nucleic acid encoding the anti-Factor D antibody or the anti-Factor D antibody fragment is selected from the group consisting of a nucleic acid encoding the amino acid sequence of SEQ ID NO:48 and a nucleic acid encoding the amino acid sequence of SEQ ID NO:49.

28. The method of claim 7, wherein the protein or the polypeptide is an antibody or an antibody fragment selected from the group consisting of an anti-MET antibody and an anti-MET antibody fragment, and wherein the nucleic acid encoding the anti-MET antibody or the anti-MET antibody fragment is selected from the group consisting of a nucleic acid encoding the amino acid sequence of SEQ ID NO: 50, a nucleic acid encoding the amino acid sequence of SEQ ID NO: 51, and a nucleic acid encoding the amino acid sequence of SEQ ID NO:52.

29. The method of claim 7, wherein expressing the protein or the polypeptide in the *E. coli* host cell is performed in the absence of exogenously added methionine to the culture medium or without a methionine feed.

* * * * *

SEQUENCE LISTING

<160> NUMBER OF SEQ ID NOS: 52

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cacacgagct cctcattttg ctcattaacg ttgg                                    34

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cacacgtcga cgcgaatgga agctg                                    25

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cacacgagct cgtatgcaaa gcagagatgc                               30

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cacacgtcga ccgtcattgc cttgtttg                                 28

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gttctgatcc ttaacctgat gccgaagaag                               30

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccagcgtttg cgcatcatat tcgg                                     24

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggcaaaacac cttttacgt ccgagtcc                                  28

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 8
gaactcacgt accagcaggg tcagttg                                          27

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccagtcacga cgttgtaaaa cgacgg                                           26

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agtgaacggc aggtatatgt gatgg                                            25

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtgatgacaa cttcttgtgc gtctggtcag g                                     31

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cctgaccaga cgcacaagaa gttgtcatca c                                     31

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
caaactcacc tttggaggtc gatattcagc                                       30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
```
gctgaatatc gacctccaaa ggtgagtttg                                           30

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gctcaactat tacgtctgcc agatcacgcc atacg                                     35

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cgtatggcgt gatctggcag acgtaatagt tgagc                                     35

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgtctaccag agcacgctat acgatctacg                                           30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cgtagatcgt atagcgtgct ctggtagacg                                           30

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atcgatgctg tcgagctttc cactcag                                              27

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

```
ctgagtggaa agctcgacag catcgat                                              27

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gcgcagctgc tggcgatgct gccg                                                 24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cggcagcatc gccagcagct gcgc                                                 24

<210> SEQ ID NO 23
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
atgccgattc gtgtgccgga cgagctaccc gccgtcaatt tcttgcgtga agaaaacgtc          60
tttgtgatga caacttcttg tgcgtctggt caggaaattc gtccacttaa ggttctgatc        120
cttaacctga tgccgaagaa gattgaaact gaaaatcagt ttctgcgcct gctttcaaac        180
tcacctttgc aggtcgatat tcagctgttg cgcatcgatt cccgtgaatc gcgcaacacg        240
cccgcagagc atctgaacaa cttctactgt aactttgaag atattcagga tcagaacttt        300
gacggtttga ttgtaactgg tgcgccgctg ggcctggtgg agtttaatga tgtcgcttac        360
tggccgcaga tcaaacaggt gctggagtgg tcgaaagatc acgtcacctc gacgctgttt        420
gtctgctggg cggtacaggc cgcgctcaat atcctctacg cattcctaa gcaaactcgc         480 accgaaaaac tctctggcgt ttacgagcat catattctcc atcctcatgc gcttctgacg        540
cgtggctttg atgattcatt cctggcaccg cattcgcgct atgctgactt tccggcagcg        600
ttgattcgtg attacaccga tctggaaatt ctggcagaga cggaagaagg ggatgcatat        660
ctgtttgcca gtaaagataa gcgcattgcc tttgtgacgg ccatcccga atatgatgcg         720 caaacgctgg cgcaggaatt tttccgcgat gtggaagccg gactagaccc ggatgtaccg        780
tataactatt tcccgcacaa tgatccgcaa aatacaccgc gagcgagctg gcgtagtcac        840
ggtaatttac tgtttaccaa ctggctcaac tattacgtct accagatcac gccatacgat        900
ctacggcaca tgaatccaac gctggattaa                                          930

<210> SEQ ID NO 24
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 24

```
atgccgattc gtgtgccgga cgagctaccc gccgtcaatt tcttgcgtga agaaaacgtc      60
tttgtgatga caacttctcg tgcgtctggt caggaaattc gtccacttaa ggttctgatc     120
cttaacctga tgccgaagaa gattgaaact gaaaatcagt ttctgcgcct gctttcaaac     180
tcacctttgc aggtcgatat tcagctgttg cgcatcgatt cccgtgaatc gcgcaacacg     240
cccgcagagc atctgaacaa cttctactgt aactttgaag atattcagga tcagaacttt     300
gacggtttga ttgtaactgg tgcgccgctg ggcctggtgg agtttaatga tgtcgcttac     360
tggccgcaga tcaaacaggt gctggagtgg tcgaaagatc acgtcacctc gacgctgttt     420
gtctgctggg cggtacaggc cgcgctcaat atcctctacg gcattcctaa gcaaactcgc     480
accgaaaaac tctctggcgt ttacgagcat catattctcc atcctcatgc gcttctgacg     540
cgtggctttg atgattcatt cctggcaccg cattcgcgct atgctgactt tccggcagcg     600
ttgattcgtg attacaccga tctggaaatt ctggcagaga cggaagaagg ggatgcatat     660
ctgtttgcca gtaaagataa gcgcattgcc tttgtgacgg ccatcccga atatgatgcg      720 caaacgctgg cgcaggaatt tttccgcgat gtggaagccg gactagaccc ggatgtaccg     780
tataactatt tcccgcacaa tgatccgcaa aatacaccgc gagcgagctg cgtagtcac      840 ggtaatttac tgtttaccaa ctggctcaac tattacgtct gccagatcac gccatacgat     900
ctacggcaca tgaatccaac gctggattaa                                      930
```

<210> SEQ ID NO 25
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
atgccgattc gtgtgccgga cgagctaccc gccgtcaatt tcttgcgtga agaaaacgtc      60
tttgtgatga caacttctcg tgcgtctggt caggaaattc gtccacttaa ggttctgatc     120
cttaacctga tgccgaagaa gattgaaact gaaaatcagt ttctgcgcct gctttcaaac     180
tcacctttgc aggtcgatat tcagctgttg cgcatcgatt cccgtgaatc gcgcaacacg     240
cccgcagagc atctgaacaa cttctactgt aactttgaag atattcagga tcagaacttt     300
gacggtttga ttgtaactgg tgcgccgctg ggcctggtgg agtttaatga tgtcgcttac     360
tggccgcaga tcaaacaggt gctggagtgg tcgaaagatc acgtcacctc gacgctgttt     420
gtctgctggg cggtacaggc cgcgctcaat atcctctacg gcattcctaa gcaaactcgc     480
accgaaaaac tctctggcgt ttacgagcat catattctcc atcctcatgc gcttctgacg     540
cgtggctttg atgattcatt cctggcaccg cattcgcgct atgctgactt tccggcagcg     600
ttgattcgtg attacaccga tctggaaatt ctggcagaga cggaagaagg ggatgcatat     660
ctgtttgcca gtaaagataa gcgcattgcc tttgtgacgg ccatcccga atatgatgcg      720 caaacgctgg cgcaggaatt tttccgcgat gtggaagccg gactagaccc ggatgtaccg     780
tataactatt tcccgcacaa tgatccgcaa aatacaccgc gagcgagctg cgtagtcac      840 ggtaatttac tgtttaccaa ctggctcaac tattacgtct accagagcac gctatacgat     900
ctacggcaca tgaatccaac gctggattaa                                      930
```

```
<210> SEQ ID NO 26
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
atgccgattc gtgtgccgga cgagctaccc gccgtcaatt tcttgcgtga agaaaacgtc      60
tttgtgatga caacttctcg tgcgtctggt caggaaattc gtccacttaa ggttctgatc     120
cttaacctga tgccgaagaa gattgaaact gaaaatcagt ttctgcgcct gctttcaaac     180
tcacctttgg aggtcgatat tcagctgttg cgcatcgatt cccgtgaatc gcgcaacacg     240
cccgcagagc atctgaacaa cttctactgt aactttgaag atattcagga tcagaacttt     300
gacggtttga ttgtaactgg tgcgccgctg ggcctggtgg agtttaatga tgtcgcttac     360
tggccgcaga tcaaacaggt gctggagtgg tcgaaagatc acgtcacctc gacgctgttt     420
gtctgctggg cggtacaggc cgcgctcaat atcctctacg gcattcctaa gcaaactcgc     480
accgaaaaac tctctggcgt ttacgagcat catattctcc atcctcatgc gcttctgacg     540
cgtggctttg atgattcatt cctggcaccg cattcgcgct atgctgactt ccggcagcg     600 ttgattcgtg attacaccga tctggaaatt ctggcagaga cggaagaagg ggatgcatat     660
ctgtttgcca gtaaagataa gcgcattgcc tttgtgacgg gccatcccga atatgatgcg     720
caaacgctgg cgcaggaatt tttccgcgat gtggaagccg actagaccc ggatgtaccg      780 tataactatt tcccgcacaa tgatccgcaa aatacaccgc gagcgagctg gcgtagtcac     840
ggtaatttac tgtttaccaa ctggctcaac tattacgtct accagatcac gccatacgat     900
ctacggcaca tgaatccaac gctggattaa                                      930

<210> SEQ ID NO 27
<211> LENGTH: 1155
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
atggcaaaac cctttttac gtccgagtcc gtctctgaag ggcatcctga caaaattgct       60
gaccaaattt ctgatgccgt tttagacgcg atcctcgaac aggatccgaa agcacgcgtt     120
gcttgcgaaa cctacgtaaa aaccggcatg gtttttagttg gcggcgaaat caccaccagc    180
gcctgggtag acatcgaaga gatcacccgt aacaccgttc gcgaaattgg ctatgtgcat    240
tccgacatgg gctttgacgc taactcctgt gcggttctga gcgctatcgg caaacagtct    300
cctgacatca accagggcgt tgaccgtgcc gatccgctgg aacagggcgc gggtgaccag    360
ggtctgatgt ttggctacgc aactaatgaa accgacgtgc tgatgccagc acctatcacc    420
tatgcacacc gtctggtaca gcgtcaggct gaagtgcgta aaaacggcac tctgccgtgg    480
ctgcgcccgg acgcgaaaag ccaggtgact tttcagtatg acgacggcaa aatcgttggt    540
atcgatgctg tcgagctttc cactcagcac tctgaagaga tcgaccagaa atcgctgcaa    600
gaagcggtaa tggaagagat catcaagcca attctgcccg ctgaatggct gacttctgcc    660
accaaattct tcatcaaccc gaccggtcgt ttcgttatcg gtgcccaat gggtgactgc     720 ggtctgactg gtcgtaaaat tatcgttgat acctacggcg gcatggcgcg tcacggtggc    780
```

```
ggtgcattct ctggtaaaga tccatcaaaa gtggaccgtt ccgcagccta cgcagcacgt      840
tatgtcgcga aaacatcgt  tgctgctggc ctggccgatc gttgtgaaat tcaggtttcc      900
tacgcaatcg gcgtggctga accgacctcc atcatggtag aaactttcgg tactgagaaa      960
gtgccttctg aacaactgac cctgctggta cgtgagttct tcgacctgcg cccatacggt     1020
ctgattcaga tgctggatct gctgcacccg atctacaaag aaaccgcagc atacggtcac     1080
tttggtcgtg aacatttccc gtgggaaaaa accgacaaag cgcagctgct gcgcgatgct     1140
gccggtctga agtaa                                                      1155

<210> SEQ ID NO 28
<211> LENGTH: 1154
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
atggcaaaac accttttac  gtccgagtcc gtctctgaag gcatcctga  caaaattgct       60 gaccaaattt ctgatgccgt tttagacgcg atcctcgaac aggatccgaa agcacgcgtt      120
gcttgcgaaa cctacgtaaa aaccggcatg gttttagttg gcggcgaaat caccaccagc      180
gcctgggtag acatcgaaga gatcacccgt aacaccgttc gcgaaattgg ctatgtgcat      240
tccgacatgg gctttgacgc taactcctgt gcggttctga gcgctatcgg caaacagtct      300
cctgacatca accagggcgt tgaccgtgcc gatccgctgg aacagggcgc gggtgaccag      360
ggtctgatgt ttggctacgc aactaatgaa accgacgtgc tgatgccagc acctatcacc      420
tatgcacacc gtctggtaca gcgtcaggct gaagtgcgta aaaacggcac tctgccgtgg      480
ctgcgcccgg acgcgaaaag ccaggtgact tttcagtatg acgacggcaa aatcgttggt      540
atcgatgctg tcgtgctttc cactcagcac tctgaagaga tcgaccagaa atcgctgcaa      600
gaagcggtaa tggaagagat catcaagcca attctgcccg ctgaatggct gacttctgcc      660
accaaattct tcatcaaccc gaccggtcgt tcgttatcg  gtggcccaat gggtgactgc      720
ggtctgactg tcgtaaaat  tatcgttgat acctacggcg gcatggcgcg tcacggtggc      780
ggtgcattct ctggtaaaga tccatcaaaa gtggaccgtt ccgcagccta cgcagcacgt      840
tatgtcgcga aaacatcgt  tgctgctggc ctggccgatc gttgtgaaat tcaggtttcc      900
tacgcaatcg gcgtggctga accgacctcc atcatggtag aaactttcgg tactgagaaa      960
gtgccttctg aacaactgac cctgctggta cgtgagttct tcgacctgcg cccatacggt     1020
ctgattcaga tgctggatct gctgcacccg atctacaaag aaaccgcagc atacggtcac     1080
tttggtcgtg aacatttccc gtgggaaaaa accgacaaag cgcagctgct ggcgatgctg     1140
ccggtctgaa gtaa                                                       1154

<210> SEQ ID NO 29
<211> LENGTH: 308
<212> TYPE: PRT
<213> ORGANISM: Escherichia coli

<400> SEQUENCE: 29

Met Pro Ile Arg Val Pro Asp Glu Leu Pro Ala Val Asn Phe Leu Arg
 1               5                  10                  15

Glu Glu Asn Val Phe Val Met Thr Thr Ser Arg Ala Ser Gly Gln Glu
            20                  25                  30
```

```
Ile Arg Pro Leu Lys Val Leu Ile Leu Asn Leu Met Pro Lys Lys Ile
         35                  40                  45

Glu Thr Glu Asn Gln Phe Leu Arg Leu Ser Asn Ser Pro Leu Gln
 50                      55                  60

Val Asp Ile Gln Leu Leu Arg Ile Asp Ser Arg Glu Ser Arg Asn Thr
 65                  70                  75                  80

Pro Ala Glu His Leu Asn Asn Phe Tyr Cys Asn Phe Glu Asp Ile Gln
                 85                  90                  95

Asp Gln Asn Phe Asp Gly Leu Ile Val Thr Gly Ala Pro Leu Gly Leu
             100                 105                 110

Val Glu Phe Asn Asp Val Ala Tyr Trp Pro Gln Ile Lys Gln Val Leu
         115                 120                 125

Glu Trp Ser Lys Asp His Val Thr Ser Thr Leu Phe Val Cys Trp Ala
 130                 135                 140

Val Gln Ala Ala Leu Asn Ile Leu Tyr Gly Ile Pro Lys Gln Thr Arg
 145                 150                 155                 160

Thr Glu Lys Leu Ser Gly Val Tyr Glu His His Ile Leu His Pro His
                 165                 170                 175

Ala Leu Leu Thr Arg Gly Phe Asp Asp Ser Phe Leu Ala His Ser Arg
             180                 185                 190

Tyr Ala Asp Phe Pro Ala Ala Leu Ile Arg Asp Tyr Thr Asp Leu Glu
         195                 200                 205

Ile Leu Ala Glu Thr Glu Glu Gly Asp Ala Tyr Leu Phe Ala Ser Lys
 210                 215                 220

Asp Lys Arg Ile Ala Phe Val Thr Gly His Pro Glu Tyr Asp Ala Gln
225                 230                 235                 240

Thr Leu Ala Gln Glu Phe Phe Arg Asp Val Glu Ala Gly Leu Asp Pro
                 245                 250                 255

Asp Val Pro Tyr Asn Tyr Phe Pro His Asn Asp Pro Gln Asn Thr Pro
             260                 265                 270

Arg Ala Ser Trp Arg Ser His Gly Asn Leu Leu Phe Thr Asn Trp Leu
         275                 280                 285

Asn Tyr Tyr Val Tyr Gln Ile Thr Pro Tyr Asp Leu Arg His Met Asn
 290                 295                 300

Pro Thr Leu Asp
305

<210> SEQ ID NO 30
<211> LENGTH: 384
<212> TYPE: PRT
<213> ORGANISM: Escherichia coli

<400> SEQUENCE: 30

Met Ala Lys His Leu Phe Thr Ser Glu Ser Val Ser Glu Gly His Pro
 1               5                  10                  15

Asp Lys Ile Ala Asp Gln Ile Ser Asp Ala Val Leu Asp Ala Ile Leu
             20                  25                  30

Glu Gln Asp Pro Lys Ala Arg Val Ala Cys Glu Thr Tyr Val Lys Thr
         35                  40                  45

Gly Met Val Leu Val Gly Gly Glu Ile Thr Thr Ser Ala Trp Val Asp
 50                  55                  60

Ile Glu Glu Ile Thr Arg Asn Thr Val Arg Glu Ile Gly Tyr Val His
 65                  70                  75                  80

Ser Asp Met Gly Phe Asp Ala Asn Ser Cys Ala Val Leu Ser Ala Ile
                 85                  90                  95
```

Gly Lys Gln Ser Pro Asp Ile Asn Gln Gly Val Asp Arg Ala Asp Pro
                100                 105                 110

Leu Glu Gln Gly Ala Gly Asp Gln Gly Leu Met Phe Gly Tyr Ala Thr
            115                 120                 125

Asn Glu Thr Asp Val Leu Met Pro Ala Pro Ile Thr Tyr Ala His Arg
        130                 135                 140

Leu Val Gln Arg Gln Ala Glu Val Arg Lys Asn Gly Thr Leu Pro Trp
145                 150                 155                 160

Leu Arg Pro Asp Ala Lys Ser Gln Val Thr Phe Gln Tyr Asp Asp Gly
                165                 170                 175

Lys Ile Val Gly Ile Asp Ala Val Val Leu Ser Thr Gln His Ser Glu
            180                 185                 190

Glu Ile Asp Gln Lys Ser Leu Gln Glu Ala Val Met Glu Ile Ile
        195                 200                 205

Lys Pro Ile Leu Pro Ala Glu Trp Leu Thr Ser Ala Thr Lys Phe Phe
210                 215                 220

Ile Asn Pro Thr Gly Arg Phe Val Ile Gly Pro Met Gly Asp Cys
225                 230                 235                 240

Gly Leu Thr Gly Arg Lys Ile Ile Val Asp Thr Tyr Gly Gly Met Ala
                245                 250                 255

Arg His Gly Gly Gly Ala Phe Ser Gly Lys Asp Pro Ser Lys Val Asp
            260                 265                 270

Arg Ser Ala Ala Tyr Ala Ala Arg Tyr Val Ala Lys Asn Ile Val Ala
        275                 280                 285

Ala Gly Leu Ala Asp Arg Cys Glu Ile Gln Val Ser Tyr Ala Ile Gly
            290                 295                 300

Val Ala Glu Pro Thr Ser Ile Met Val Glu Thr Phe Gly Thr Glu Lys
305                 310                 315                 320

Val Pro Ser Glu Gln Leu Thr Leu Leu Val Arg Glu Phe Phe Asp Leu
                325                 330                 335

Arg Pro Tyr Gly Leu Ile Gln Met Leu Asp Leu Leu His Pro Ile Tyr
            340                 345                 350

Lys Glu Thr Ala Ala Tyr Gly His Phe Gly Arg Glu His Phe Pro Trp
        355                 360                 365

Glu Lys Thr Asp Lys Ala Gln Leu Leu Arg Asp Ala Ala Gly Leu Lys
    370                 375                 380

<210> SEQ ID NO 31
<211> LENGTH: 930
<212> TYPE: DNA
<213> ORGANISM: Escherichia coli

<400> SEQUENCE: 31
atgccgattc gtgtgccgga cgagctaccc gccgtcaatt tcttgcgtga agaaaacgtc    60
tttgtgatga caacttcttg tgcgtctggt caggaaattc gtccacttaa ggttctgatc   120
cttaacctga tgccgaagaa gattgaaact gaaaatcagt ttctgcgcct gctttcaaac   180
tcacctttgc aggtcgatat tcagctgttg cgcatcgatt cccgtgaatc gcgcaacacg   240
cccgcagagc atctgaacaa cttctactgt aactttgaag atattcagga tcagaacttt   300
gacggtttga ttgtaactgg tgcgccgctg ggcctggtgg agtttaatga tgtcgcttac   360
tggccgcaga tcaaacaggt gctggagtgg tcgaaagatc acgtcacctc gacgctgttt   420
gtctgctggg cggtacaggc cgcgctcaat atcctctacg gcattcctaa gcaaactcgc   480

```
accgaaaaac tctctggcgt ttacgagcat catattctcc atcctcatgc gcttctgacg        540
cgtggctttg atgattcatt cctggcaccg cattcgcgct atgctgactt tccggcagcg        600
ttgattcgtg attacaccga tctggaaatt ctggcagaga cggaagaagg ggatgcatat        660
ctgtttgcca gtaaagataa gcgcattgcc tttgtgacgg ccatcccga atatgatgcg         720 caaacgctgg cgcaggaatt tttccgcgat gtggaagccg actagaccc ggatgtaccg         780 tataactatt tcccgcacaa tgatccgcaa aatacaccgc gagcgagctg gcgtagtcac        840
ggtaatttac tgtttaccaa ctggctcaac tattacgtct accagatcac gccatacgat        900
ctacggcaca tgaatccaac gctggattaa                                         930

<210> SEQ ID NO 32
<211> LENGTH: 1155
<212> TYPE: DNA
<213> ORGANISM: Escherichia coli

<400> SEQUENCE: 32
atggcaaaac ccttttttac gtccgagtcc gtctctgaag gcatcctga caaaattgct         60 gaccaaattt ctgatgccgt tttagacgcg atcctcgaac aggatccgaa agcacgcgtt        120
gcttgcgaaa cctacgtaaa aaccggcatg gttttagttg gcggcgaaat caccaccagc       180
gcctgggtag acatcgaaga gatcacccgt aacaccgttc gcgaaattgg ctatgtgcat       240
tccgacatgg gctttgacgc taactcctgt gcggttctga gcgctatcgg caaacagtct      300
cctgacatca accagggcgt tgaccgtgcc gatccgctgg aacagggcgc gggtgaccag       360
ggtctgatgt ttggctacgc aactaatgaa accgacgtgc tgatgccagc acctatcacc       420
tatgcacacc gtctggtaca gcgtcaggct gaagtgcgta aaaacggcac tctgccgtgg       480
ctgcgcccgg acgcgaaaag ccaggtgact tttcagtatg acgacggcaa atcgttggt        540 atcgatgctg tcgtgctttc cactcagcac tctgaagaga tcgaccagaa atcgctgcaa       600
gaagcggtaa tggaagagat catcaagcca attctgcccg ctgaatggct gacttctgcc      660
accaaattct tcatcaaccc gaccggtcgt ttcgttatcg gtggcccaat gggtgactgc      720
ggtctgactg tcgtaaaaat tatcgttgat acctacggcg gcatggcgcg tcacggtggc      780
ggtgcattct ctggtaaaga tccatcaaaa gtggaccgtt ccgcagccta cgcagcacgt      840
tatgtcgcga aaacatcgt tgctgctggc ctggccgatc gttgtgaaat tcaggtttcc      900
tacgcaatcg gcgtggctga accgacctcc atcatggtag aaactttcgg tactgagaaa      960
gtgccttctg aacaactgac cctgctggta cgtgagttct tcgacctgcg cccatacggt       1020
ctgattcaga tgctggatct gctgcacccg atctacaaag aaaccgcagc atacggtcac      1080
tttggtcgtg aacatttccc gtgggaaaaa accgacaaag cgcagctgct gcgcgatgct      1140
gccggtctga agtaa                                                        1155

<210> SEQ ID NO 33
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
gatatccagt tgacccagtc cccgagctcc ctgtccgcct ctgtgggcga tagggtcacc       60
atcacctgca gcgcaagtca ggatattagc aactatttaa actggtatca acagaaacca      120
```

```
ggaaaagctc cgaaagtact gatttacttc acctcctctc tccactctgg agtcccttct      180
cgcttctctg gatccggttc tgggacggat ttcactctga ccatcagcag tctgcagcca      240
gaagacttcg caacttatta ctgtcaacag tatagcaccg tgccgtggac gtttggacag      300
ggtaccaagg tggagatcaa acgaactgtg gctgcaccat ctgtcttcat cttcccgcca      360
tctgatgagc agttgaaatc tggaactgct tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga aaacacaaa gtctacgcct gcgaagtcac ccatcagggc      600
ctgagctcgc ccgtcacaaa gagcttcaac aggggagagt gt      642
```

```
<210> SEQ ID NO 34
<211> LENGTH: 693
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
```

```
gaggttcagc tggtggagtc tggcggtggc ctggtgcagc caggggggctc actccgtttg      60 tcctgtgcag cttctggcta cgacttcacg cactacggta tgaactgggt ccgtcaggcc      120
ccgggtaagg gcctggaatg ggttggatgg attaacacct ataccggtga accgacctat      180
gctgcggatt tcaaacgtcg tttcactttt tctttagaca cctccaaaag cacagcatac      240
ctgcagatga acagcctgcg cgctgaggac actgccgtct attactgtgc aaagtacccg      300
tactattatg ggacgagcca ctggtatttc gacgtctggg gtcaaggaac cctggtcacc      360
gtctcctcgg cctccaccaa gggcccatcg gtcttccccc tggcaccctc ctccaagagc      420
acctctgggg gcacagcggc cctgggctgc ctggtcaagg actacttccc cgaaccggtg      480
acggtgtcgt ggaactcagg cgccctgacc agcggcgtgc acaccttccc ggctgtccta      540
cagtcctcag gactctactc cctcagcagc gtggtgaccg tgccctccag cagcttgggc      600
acccagacct acatctgcaa cgtgaatcac aagcccagca caccaaggt cgacaagaaa      660 gttgagccca atcttgtgac aaaaactcac ctc      693
```

```
<210> SEQ ID NO 35
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Ser Cys Ala Ala Ser Gly Tyr Asp Phe Thr His Tyr Gly Met Asn
1               5                   10                  15

Trp Val Arg
```

```
<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36
```

Ser Thr Ala Tyr Leu Gln Met Asn Ser Leu Arg
1               5                   10

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Ser Gly Tyr Thr Phe Thr Asn Tyr Gly Met Asn Trp Val Arg
1               5                   10                  15

<210> SEQ ID NO 38
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Ala Pro Gly Gln Gly Leu Glu Trp Met Gly Trp Ile Asn Thr Tyr
1               5                   10                  15

Thr Gly Glu Thr Thr Tyr Ala Asp Asp Phe Lys
            20                  25

<210> SEQ ID NO 39
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Val Thr Ile Thr Cys Ile Thr Ser Thr Asp Ile Asp Asp Met Asn
1               5                   10                  15

Trp Tyr Gln Gln Lys Pro Gly Lys
            20

<210> SEQ ID NO 40
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Leu Glu Trp Val Gly Met Ile Asp Pro Ser Asn Ser Asp Thr Arg
1               5                   10                  15

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asn Thr Ala Tyr Leu Gln Met Asn Ser Leu Arg
1               5                   10

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp Thr Leu Met Ile Ser Arg
1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Glu Glu Met Thr Lys
1               5

<210> SEQ ID NO 44
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Trp Gln Gln Gly Asn Val Phe Ser Cys Ser Val Met His Glu Ala Leu
1               5                   10                  15

His Asn His Tyr Thr Gln Lys
            20

<210> SEQ ID NO 45
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asp Ile Gln Met Thr Gln Ser Pro Ser Ser Leu Ser Ala Ser Val Gly
1               5                   10                  15

Asp Arg

<210> SEQ ID NO 46
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

```
Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
 50                      55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                     135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 47
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
 50                      55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175
```

```
Pro Ala Val Leu Gln Ser Ser Gly Leu Tyr Ser Leu Ser Ser Val Val
            180                 185                 190

Thr Val Pro Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Leu
225                 230

<210> SEQ ID NO 48
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Ile Gln Val Thr Gln Ser Pro Ser Ser Leu Ser Ala Ser Val Gly
1               5                   10                  15

Asp Arg Val Thr Ile Thr Cys Ile Thr Ser Thr Asp Ile Asp Asp Asp
            20                  25                  30

Met Asn Trp Tyr Gln Gln Lys Pro Gly Lys Val Pro Lys Leu Leu Ile
        35                  40                  45

Ser Gly Gly Asn Thr Leu Arg Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Ser Asp Ser Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 49
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Gln Ser Gly Pro Glu Leu Lys Lys Pro Gly Ala
1               5                   10                  15
```

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
 50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr
210                 215                 220

<210> SEQ ID NO 50
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
            20                  25                  30

Ser Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu

```
145                 150                 155                 160
Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 51
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Gln Ala Pro Gly Lys Gly Leu Glu Trp Val
        35                  40                  45

Gly Met Ile Asp Pro Ser Asn Ser Asp Thr Arg Phe Asn Pro Asn Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Ser
            355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 52
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190
```

-continued

```
Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
        210                 215                 220

Pro Gly Lys
225
```